(12) United States Patent
Masuyama et al.

(10) Patent No.: US 8,900,790 B2
(45) Date of Patent: Dec. 2, 2014

(54) PHOTORESIST COMPOSITION

(75) Inventors: Tatsuro Masuyama, Toyonaka (JP); Mitsuhiro Hata, Delmar, NY (US)

(73) Assignee: Sumitomo Chemical Company, Limited, Tokyo (JP)

( * ) Notice: Subject to any disclaimer, the term of this patent is extended or adjusted under 35 U.S.C. 154(b) by 237 days.

(21) Appl. No.: 12/880,852

(22) Filed: Sep. 13, 2010

(65) Prior Publication Data

US 2011/0065040 A1    Mar. 17, 2011

(30) Foreign Application Priority Data

Sep. 16, 2009 (JP) .................... 2009-214255
Mar. 15, 2010 (JP) .................... 2010-057481

(51) Int. Cl.
| | | |
|---|---|---|
| *G03F 7/004* | (2006.01) | |
| *C07C 271/22* | (2006.01) | |
| *G03F 7/039* | (2006.01) | |
| *G03F 7/20* | (2006.01) | |
| *C07D 207/16* | (2006.01) | |

(52) U.S. Cl.
CPC ............ *C07C 271/22* (2013.01); *G03F 7/0392* (2013.01); *G03F 7/20* (2013.01); *C07D 207/16* (2013.01); *G03F 7/0045* (2013.01); *G03F 7/0046* (2013.01); *G03F 7/0397* (2013.01)
USPC .......................... 430/270.1; 430/322; 430/326

(58) Field of Classification Search
None
See application file for complete search history.

(56) References Cited

U.S. PATENT DOCUMENTS

| | | | |
|---|---|---|---|
| 6,399,272 | B1 | 6/2002 | Lee et al. |
| 2001/0023050 | A1 | 9/2001 | Numata et al. |
| 2003/0194639 | A1 | 10/2003 | Miya et al. |
| 2006/0194982 | A1 | 8/2006 | Harada et al. |
| 2007/0122750 | A1* | 5/2007 | Yamaguchi et al. .......... 430/311 |
| 2008/0153032 | A1* | 6/2008 | Rahman et al. ............ 430/281.1 |

FOREIGN PATENT DOCUMENTS

| | | | |
|---|---|---|---|
| JP | 01140144 | A * | 6/1989 |
| JP | 6-148887 | A | 5/1994 |
| JP | 7-333851 | A | 12/1995 |
| JP | 2001-166476 | A | 6/2001 |
| JP | 2001166476 | A * | 6/2001 |
| JP | 2006321770 | A * | 11/2006 |
| JP | 2009-199021 | A | 9/2009 |

OTHER PUBLICATIONS

Machine translation JP 2001-166476. Jun. 22, 2001.*
Machine translation 2006-321770. Nov. 30, 2006.*
Written translation JP 01-140144. Jun. 1, 1989.*
The Notice of Reasons for the Rejection, dated Jul. 22, 2014, issued in the corresponding Japanese Patent Application No. 2010-204073.

* cited by examiner

*Primary Examiner* — Anca Eoff
*Assistant Examiner* — Alyssa L Cepluch
(74) *Attorney, Agent, or Firm* — Birch, Stewart, Kolasch & Birch LLP

(57) ABSTRACT

A photoresist composition comprising a resin, an acid generator and a compound represented by the formula (I):

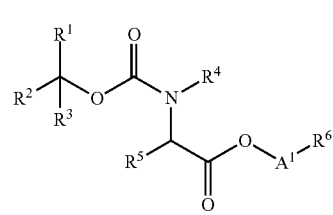

(I)

wherein $R^1$ represents a C2-C12 alkyl group which can have one or more hydroxyl groups, etc., $R^2$ and $R^3$ each independently represent a hydrogen atom, etc., $R^4$, $R^5$ and $R^6$ each independently represent a hydrogen atom, etc., $A^1$ represents a single bond or a C1-C2 alkylene group in which one or more $—CH_2—$ can be replaced by $—O—$.

5 Claims, No Drawings

PHOTORESIST COMPOSITION

This nonprovisional application claims priority under 35 U.S.C. §119(a) on Patent Application No. 2009-214255 filed in JAPAN on Sep. 16, 2009, and on Patent Application No. 2010-057481 filed in JAPAN on Mar. 15, 2010, the entire contents of which are hereby incorporated by reference.

FIELD OF THE INVENTION

The present invention relates to a photoresist composition.

BACKGROUND OF THE INVENTION

A photoresist composition used for semiconductor microfabrication employing a lithography process contains an acid generator comprising a compound generating an acid by irradiation.

US 2006/0194982 A1 discloses a photoresist composition comprising a resin having an acid-labile group, being insoluble or poorly soluble in an aqueous alkali solution but becoming soluble in an aqueous alkali solution by the action of an acid, an acid generator and 2,6-diisopropylaniline.

JP 2009-199021 A1 discloses a photoresist composition comprising a compound represented by the following formula:

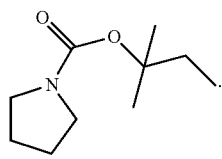

SUMMARY OF THE INVENTION

The present invention is to provide a photoresist composition.

The present invention relates to the followings:
<1> A photoresist composition comprising a resin, an acid generator and a compound represented by the formula (I):

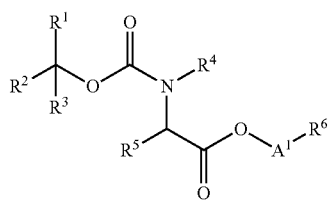

wherein $R^1$ represents a C2-C12 alkyl group which can have one or more hydroxyl groups or a C7-C12 aralkyl group which can have one or more hydroxyl groups, and one or more —CH$_2$— in the alkyl and aralkyl groups can be replaced by —O— or —CO—,
$R^2$ and $R^3$ each independently represent a hydrogen atom or a C1-C12 alkyl group which can have one or more hydroxyl groups, and one or more —CH$_2$— in the alkyl group can be replaced by —O— or —CO—, and $R^1$ and $R^2$ can be bonded each other to form a C3-C36 ring together with the carbon atom to which $R^1$ and $R^2$ are bonded, and the ring can have one or more hydroxyl groups and one or more —CH$_2$— in the ring can be replaced by —O— or —CO—,
$R^4$, $R^5$ and $R^6$ each independently represent a hydrogen atom, a C1-C6 alkyl group, a C3-C12 saturated cyclic hydrocarbon group, a C6-C12 aromatic hydrocarbon group or a C5-C9 heteroaromatic group, and $R^4$ and $R^5$ can be bonded each other to form a C5-C6 heterocycle together with —CH—N— to which $R^4$ and $R^5$ are bonded, and the alkyl group can have one or more substituents selected from the group consisting of —OH, —SH, —NH$_2$, a C3-C12 saturated cyclic hydrocarbon group, a C6-C12 aromatic hydrocarbon group or a C5-C9 heteroaromatic group, and one or more —CH$_2$— in the alkyl group can be replaced by —O—, —S—, —CO—, —C(=NH) or —NH—, and the saturated cyclic hydrocarbon group, the aromatic hydrocarbon group and the heteroaromatic group can have one or more substituents selected from the group consisting of —OH, —CO—$R^7$, —O—CO—$R^7$ and —CO—O—$R^7$ in which $R^7$ represents a C1-C6 alkyl group, and
$A^1$ represents a single bond or a C1-C2 alkylene group in which one or more —CH$_2$— can be replaced by —O—;
<2> The photoresist composition according to <1>, wherein $R^1$ is an ethyl group and $R^2$ and $R^3$ are methyl groups in the formula (I);
<3> The photoresist composition according to <1> or <2>, wherein $R^4$ is a hydrogen atom in the formula (I);
<4> The photoresist composition according to any one of <1> to <3>, wherein the resin has an acid-labile group and is insoluble or poorly soluble in an aqueous alkali solution but becomes soluble in an aqueous alkali solution by the action of an acid;
<5> A process for producing a photoresist pattern comprising the following steps (1) to (5):
(1) a step of applying the photoresist composition according to any one of <1> to <4> on a substrate,
(2) a step of forming a photoresist film by conducting drying,
(3) a step of exposing the photoresist film to radiation,
(4) a step of baking the exposed photoresist film, and
(5) a step of developing the baked photoresist film with an alkaline developer, thereby forming a photoresist pattern;
<6> A compound represented by the formula (I-A):

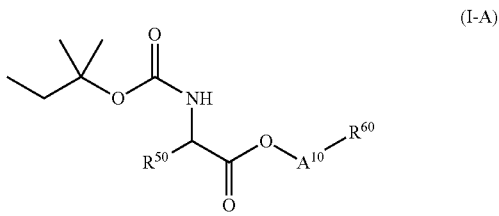

wherein $A^{10}$ represents a methylene group, $R^{50}$ represents a C1-C6 alkyl group and $R^{60}$ represents a phenyl group or a phenyl group having —COOR$^{70}$ in which $R^{70}$ represents a C1-C6 alkyl group;
<7> A compound represented by the formula (I-12), (I-20) or (I-110):

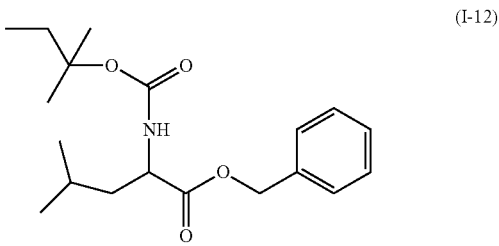

-continued

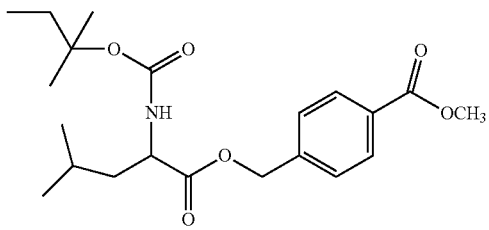

(I-20)

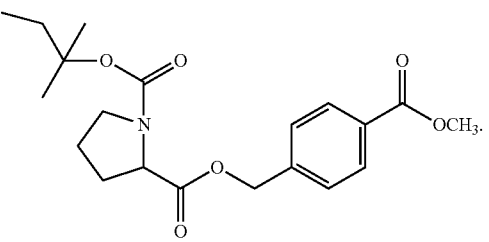

(I-110)

DESCRIPTION OF PREFERRED EMBODIMENTS

The photoresist composition of the present invention comprises a resin, an acid generator and a compound represented by the formula (I):

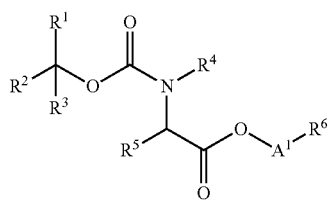

(I)

wherein represents a C2-C12 alkyl group which can have one or more hydroxyl groups or a C7-C12 aralkyl group which can have one or more hydroxyl groups, and one or more —$CH_2$— in the alkyl and aralkyl groups can be replaced by —O— or —CO—,
$R^2$ and $R^3$ each independently represent a hydrogen atom or a C1-C12 alkyl group which can have one or more hydroxyl groups, and one or more —$CH_2$— in the alkyl group can be replaced by —O— or —CO—, and $R^1$ and $R^2$ can be bonded each other to form a C3-C36 ring together with the carbon atom to which $R^1$ and $R^2$ are bonded, and the ring can have one or more hydroxyl groups and one or more —$CH_2$— in the ring can be replaced by —O— or —CO—,
$R^4$, $R^5$ and $R^6$ each independently represent a hydrogen atom, a C1-C6 alkyl group, a C3-C12 saturated cyclic hydrocarbon group, a C6-C12 aromatic hydrocarbon group or a C5-C9 heteroaromatic group, and $R^4$ and $R^5$ can be bonded each other to form a C5-C6 heterocycle together with —CH—N— to which $R^4$ and $R^5$ are bonded, and the alkyl group can have one or more substituents selected from the group consisting of —OH, —SH, —$NH_2$, a C3-C12 saturated cyclic hydrocarbon group, a C6-C12 aromatic hydrocarbon group or a C5-C9 heteroaromatic group, and one or more —$CH_2$— in the alkyl group can be replaced by —O—, —S—, —CO—, —C(=NH) or —NH—, and the saturated cyclic hydrocarbon group, the aromatic hydrocarbon group and the heteroaromatic group can have one or more substituents selected from the group consisting of —OH, —CO—$R^7$, —O—CO—$R^7$ and —CO—O—$R^7$ in which $R^7$ represents a C1-C6 alkyl group, and
$A^1$ represents a single bond or a C1-C2 alkylene group in which one or more —$CH_2$— can be replaced by —O— (hereinafter, simply referred to as Compound (I)).

Compound (I) acts as a quencher in the photoresist composition of the present invention. Performance deterioration caused by inactivation of acid which occurs due to post exposure delay can be diminished by adding Compound (I) as a quencher.

Compound (I) consists of a group represented by the formula (IA):

(IA)

wherein $R^1$, $R^2$ and $R^3$ are the same as defined above (hereinafter, simply referred to as Group (IA)), and a group represented by the formula (IB):

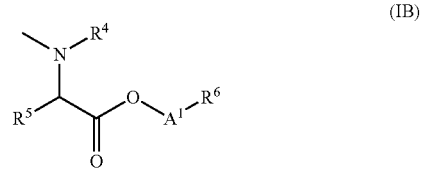

(IB)

wherein $R^4$, $R^5$, $R^6$ and $A^1$ are the same as defined above (hereinafter, simply referred to as Group (IB)).

Group (IA) will be illustrated.

Examples of the C1-C12 alkyl group include a methyl group, an ethyl group, a propyl group, an isopropyl group, a butyl group, a tert-butyl group, a pentyl group, an isopentyl group, a tert-pentyl group, a neopentyl group, a 1-methylbutyl group, a 2-methylbutyl group, a 1,2-dimethylpropyl group, a 1-ethylpropyl group, a hexyl group, a 1-methylpentyl group, a heptyl group, an octyl group, a nonyl group, a decyl group, an undecyl group, a dodecyl group, an ethylpentyl group, a methylhexyl group, an ethylhexyl group, a propylhexyl group and a 1,1-dimethylhexyl group. Examples of the C2-C12 alkyl group include the same as described in examples of the C1-C12 alkyl group other than a methyl group.

Examples of the C7-C12 aralkyl group include the followings.

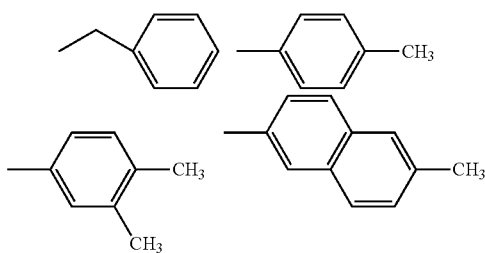

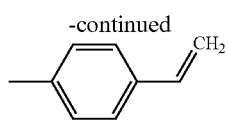

Examples of the C3-C36 ring formed by bonding $R^1$ and $R^2$ each other together with the carbon atom to which $R^1$ and $R^2$ are bonded include a C3-C36 saturated hydrocarbon ring and a C3-C36 aromatic ring, and specific examples thereof include the followings.

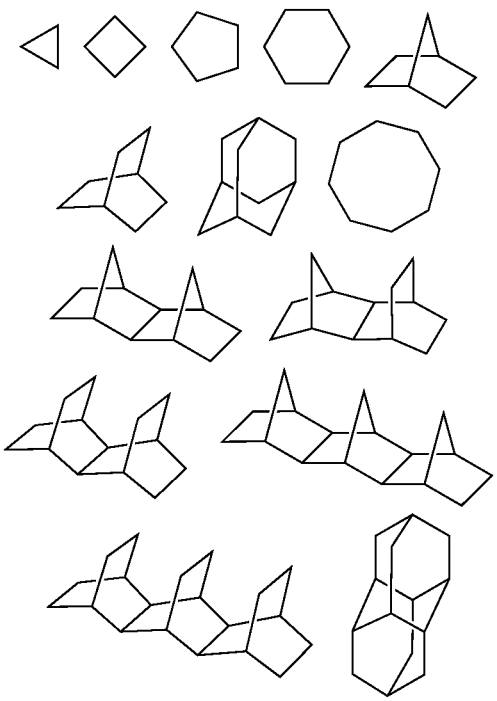

wherein the ring can have one or more hydroxyl groups and one or more —$CH_2$— in the ring can be replaced by —O— or —CO—.

Examples of the ring having one or more hydroxyl groups and the ring in which one or more —$CH_2$— are replaced by —O— or —CO— include the followings.

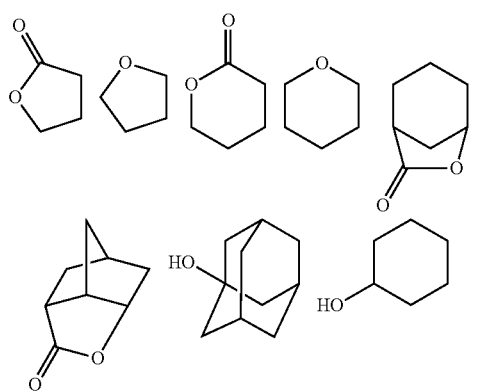

Examples of the group represented by the formula (IA) include the groups represented by the formulae (IA-1) to (IA-29):

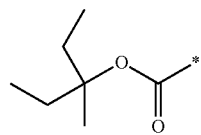
(IA-1)

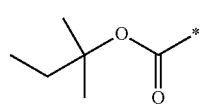
(IA-2)

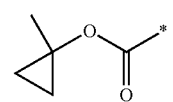
(IA-3)

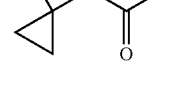
(IA-4)

(IA-5)

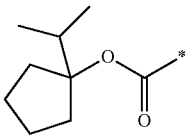
(IA-6)

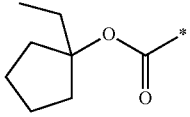
(IA-7)

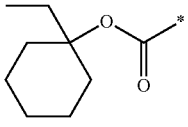
(IA-8)

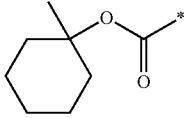
(IA-9)

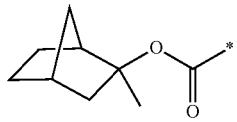
(IA-10)

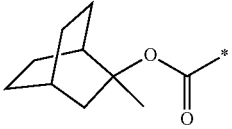
(IA-11)

-continued

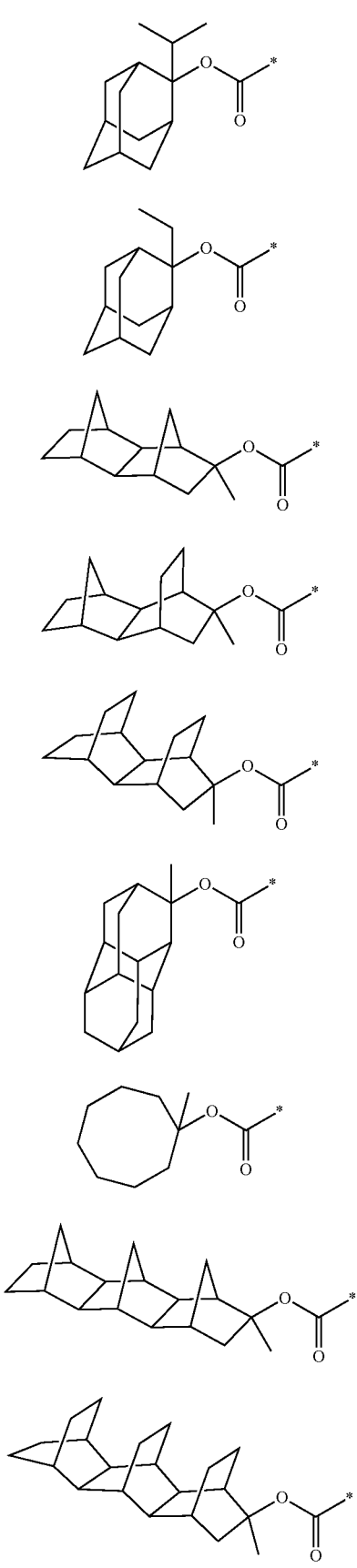

(IA-12)
(IA-13)
(IA-14)
(IA-15)
(IA-16)
(IA-17)
(IA-18)
(IA-19)
(IA-20)

-continued

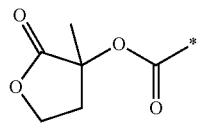
(IA-21)

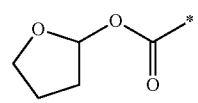
(IA-22)

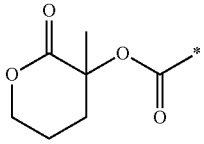
(IA-23)

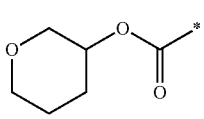
(IA-24)

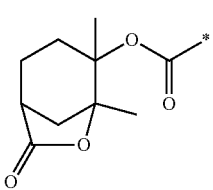
(IA-25)

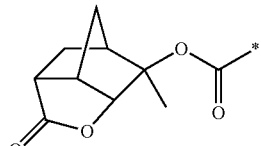
(IA-26)

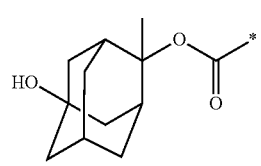
(IA-27)

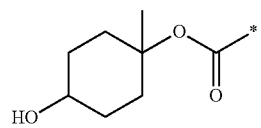
(IA-28)

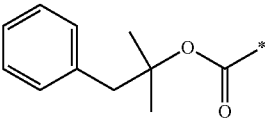
(IA-29)

wherein * represents a binding position to —$NR^4$—.

Among them, preferred is the group represented by the formula (IA-2).

Group (IB) will be illustrated.

Examples of the C1-C6 alkyl group include a methyl group, an ethyl group, a propyl group, an isopropyl group, a butyl group, a tert-butyl group, a pentyl group, an isopentyl group, a tert-pentyl group, a neopentyl group, a 1-methylbutyl group, a 2-methylbutyl group, a 1,2-dimethylpropyl group, a 1-ethylpropyl group, a hexyl group and a 1-methylpentyl group. Examples of the C3-C12 saturated cyclic hydrocarbon group include a cycloalkyl group such as a cyclohexyl group, a cycloheptyl group and a cyclooctyl group, a norbornyl group, a bicycle[2.2.2]octyl group, a 1-adamantyl group and a 2-adamantyl group.

Examples of the C6-C12 aromatic hydrocarbon group include a phenyl group, a methylphenyl group such as a 4-methylphenyl group, a dimethylphenyl group such as a 3,4-dimethylphenyl group and a naphthyl group such as a 2-naphthyl group. Examples of the C5-C9 heteroaromatic group include the followings.

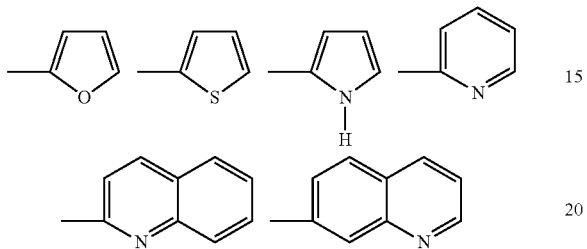

Examples of the C1-C2 alkylene group include a methylene group and an ethylene group.

Examples of $R^4$ and $R^5$ include the groups represented by the formulae (IB-1) to (IB-21) and examples of the group represented by $-A^1-R^6$ include the groups represented by the formulae (IB-1) to (IB-33).

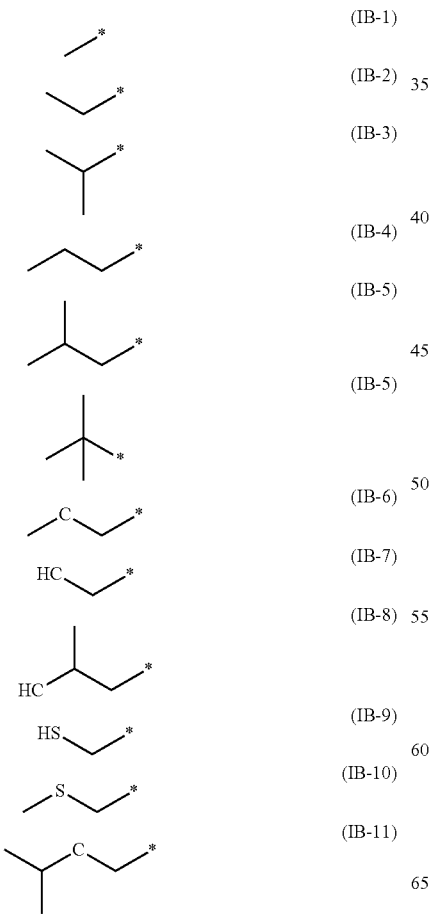

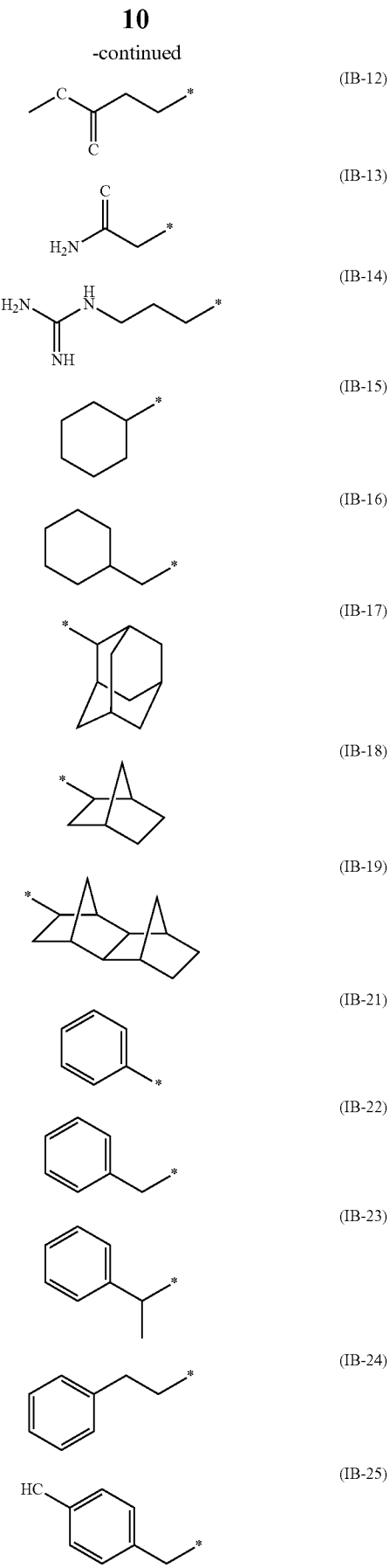

-continued

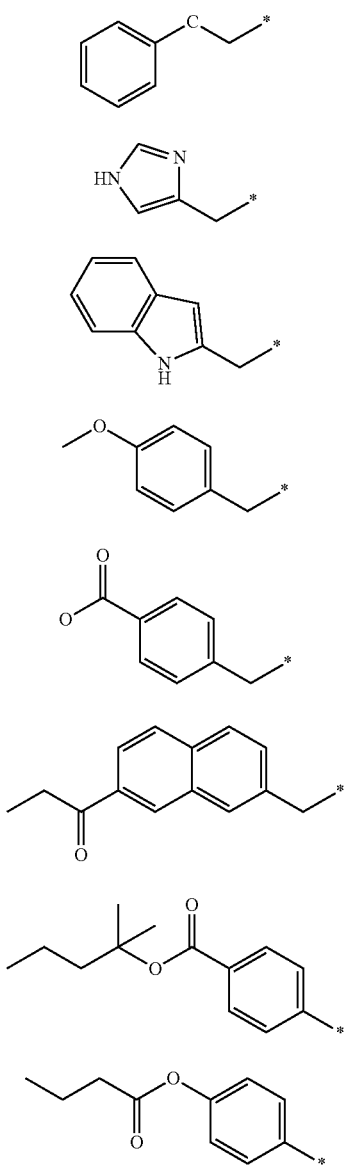

wherein * represents a binding position to an adjacent atom.

Among them, preferred is the group represented by the formula (IB-22) or (IB-30).

When $R^4$ and $R^5$ are bonded each other to form a C5-C6 heterocycle together with —CH—N— to which $R^4$ and $R^5$ are bonded, examples of Group (IB) include a group represented by the formula (IC):

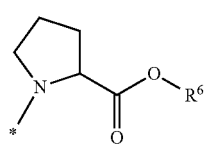

wherein * represents a binding position to —CO— (hereinafter, simply referred to as Group (IC)). Examples of Group (IC) include the groups represented by the formulae (IC-1) to (IC-6):

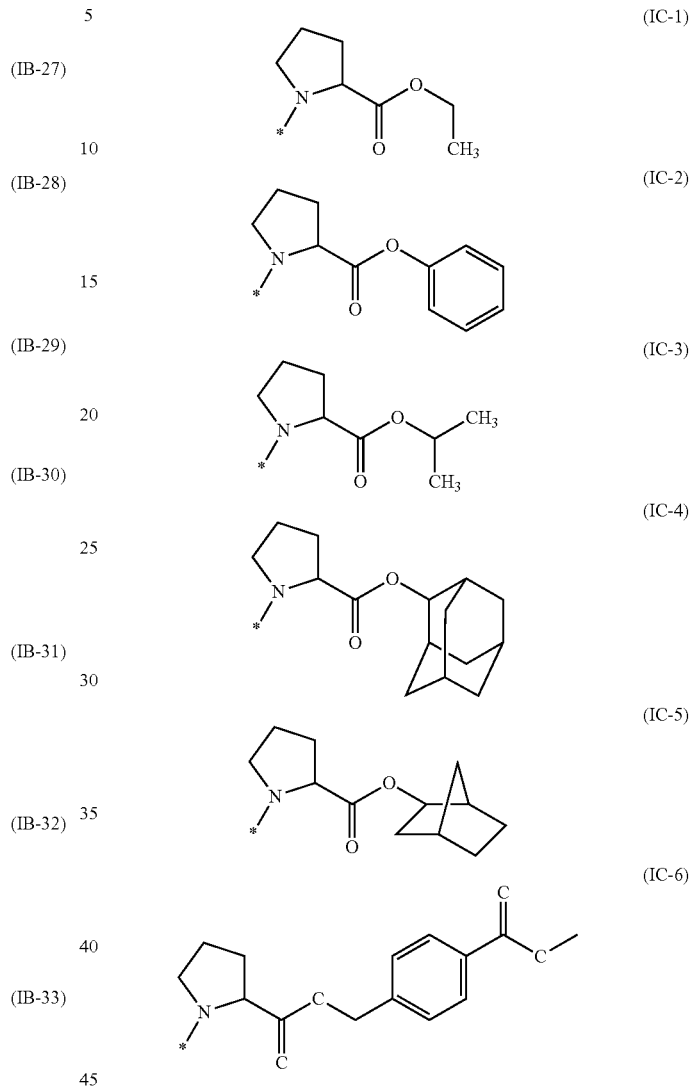

wherein * represents a binding position to —CO—.

Examples of Compound (I) include combinations of any one of the groups represented by the formula (IA-1) to (IA-29) and any one of the groups represented by the formula (IB-1) to (IB-33), and combinations of any one of the groups represented by the formula (IA-1) to (IA-29) and any one of the groups represented by the formula (IC-1) to (IC-5). Specific examples of Compound (I) include compounds (I-1) to (I-24) shown in Table 1 and compounds (I-101) to (I-110) shown in Table 2. Among them, preferred is compound (I-12).

TABLE 1

| Compound (I) | Group (IA) | $R^4$ | $R^5$ | $-A^1-R^6$ |
|---|---|---|---|---|
| (I-1) | (IA-1) | H | H | (IB-1) |
| (I-2) | (IA-2) | H | H | (IB-5) |
| (I-3) | (IA-1) | H | (IB-1) | (IB-2) |
| (I-4) | (IA-2) | H | (IB-1) | (IB-26) |
| (I-5) | (IA-1) | H | (IB-3) | (IB-1) |
| (I-6) | (IA-1) | H | (IB-3) | (IB-16) |
| (I-7) | (IA-2) | H | (IB-3) | (IB-25) |

TABLE 1-continued

| Compound (I) | Group (IA) | R⁴ | R⁵ | -A¹-R⁶ |
|---|---|---|---|---|
| (I-8) | (IA-2) | H | (IB-3) | (IB-27) |
| (I-9) | (IA-1) | H | (IB-5) | H |
| (I-10) | (IA-1) | H | (IB-5) | (IB-2) |
| (I-11) | (IA-2) | (IB-4) | (IB-5) | (IB-5) |
| (I-12) | (IA-2) | H | (IB-5) | (IB-22) |
| (I-13) | (IA-7) | H | (IB-7) | (IB-1) |
| (I-14) | (IA-11) | H | (IB-7) | (IB-1) |
| (I-15) | (IA-11) | H | (IB-8) | (IB-1) |
| (I-16) | (IA-21) | (IB-1) | (IB-8) | (IB-1) |
| (I-17) | (IA-2) | H | (IB-13) | (IB-1) |
| (I-18) | (IA-2) | (IB-2) | (IB-14) | (IB-1) |
| (I-19) | (IA-1) | H | (IB-5) | (IB-29) |
| (I-20) | (IA-2) | H | (IB-5) | (IB-30) |
| (I-21) | (IA-2) | H | (IB-5) | (IB-31) |
| (I-22) | (IA-7) | H | (IB-7) | (IB-32) |
| (I-23) | (IA-11) | H | (IB-7) | (IB-33) |
| (I-24) | (IA-2) | H | (IB-5) | H |

TABLE 2

| Compound (I) | Group (IA) | Group (IC) |
|---|---|---|
| (I-101) | (IA-1) | (IC-1) |
| (I-102) | (IA-1) | (IC-2) |
| (I-103) | (IA-2) | (IC-1) |
| (I-104) | (IA-2) | (IC-2) |
| (I-105) | (IA-2) | (IC-4) |
| (I-106) | (IA-7) | (IC-1) |
| (I-107) | (IA-7) | (IC-2) |
| (I-108) | (IA-8) | (IC-1) |
| (I-109) | (IA-8) | (IC-2) |
| (I-110) | (IA-2) | (IC-5) |

For example, the compound (I-12) is represented by the following formula (I-12), and the compound (I-20) and (I-110) are also represented by the following formulae (I-20) and (I-110), respectively.

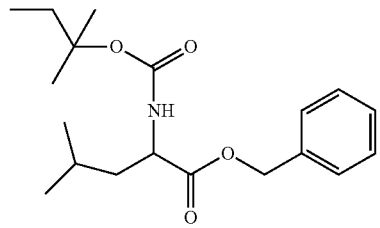

(I-12)

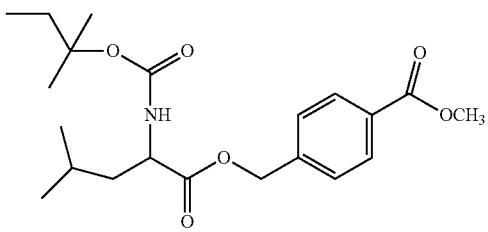

(I-20)

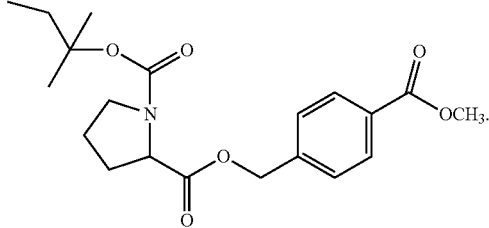

(I-110)

As Compound (I), a compound represented by the formula (I-A):

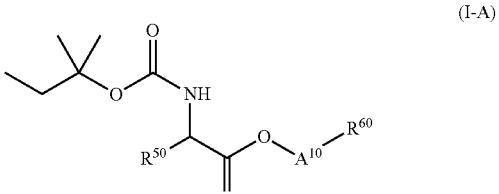

(I-A)

wherein $A^{10}$ represents a methylene group, $R^{50}$ represents a C1-C6 alkyl group and $R^{60}$ represents a phenyl group or a phenyl group having —$COOR^{70}$ in which $R^{70}$ represents a C1-C6 alkyl group, is preferable.

The photoresist composition of the present invention can contain two or more kinds of Compound (I). The content of Compound (I) is usually 0.01 to 10% by weight, preferably 0.005 to 8% by weight and more preferably 0.1 to 5% by weight based on amount of solid component. In this specification, "solid component" means components other than solvent in the photoresist composition.

The resin is insoluble or poorly soluble in an alkali aqueous solution but becomes soluble in an alkali aqueous solution by the action of an acid. The resin has a structural unit derived from a compound having an acid-labile group, and can be produced by polymerizing one or more compounds having an acid-labile group.

In this specification, "an acid-labile group" means a group capable of being eliminated by the action of an acid.

Examples of the acid-labile group include a group represented by the formula (1):

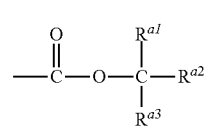

(1)

wherein $R^{a1}$, $R^{a2}$ and $R^{a3}$ independently each represent a C1-C8 aliphatic hydrocarbon group or a C3-C20 saturated cyclic hydrocarbon group, or $R^{a1}$ and $R^{a2}$ are bonded each other to form a C3-C20 ring together with a carbon atom to which $R^{a1}$ and $R^{a2}$ are bonded.

Examples of the C1-C8 aliphatic hydrocarbon group include a C1-C8 alkyl group. Specific examples of the C1-C8 alkyl group include a methyl group, an ethyl group, a propyl group, an isopropyl group, a butyl group, a pentyl group, a hexyl group, a heptyl group and an octyl group. The C3-C20 saturated cyclic hydrocarbon group may be monocyclic or polycyclic, and examples thereof include a monocyclic alicyclic hydrocarbon group such as a C3-C20 cycloalkyl group (e.g. a cyclopentyl group, a cyclohexyl group, a methylcyclohexyl group, a dimethylcyclohexyl group, a cycloheptyl group and a cyclooctyl group) and a polycyclic alicyclic hydrocarbon group such as a decahydronaphthyl group, an adamantyl group, a norbornyl group, a methylnorbornyl group, and the followings:

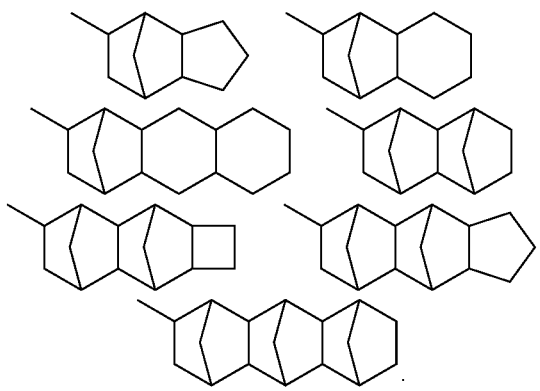

The saturated cyclic hydrocarbon group preferably has 1 to 16 carbon atoms.

Examples of the ring formed by bonding $R^{a1}$ and $R^{a2}$ each other include the following groups and the ring preferably has 3 to 12 carbon atoms.

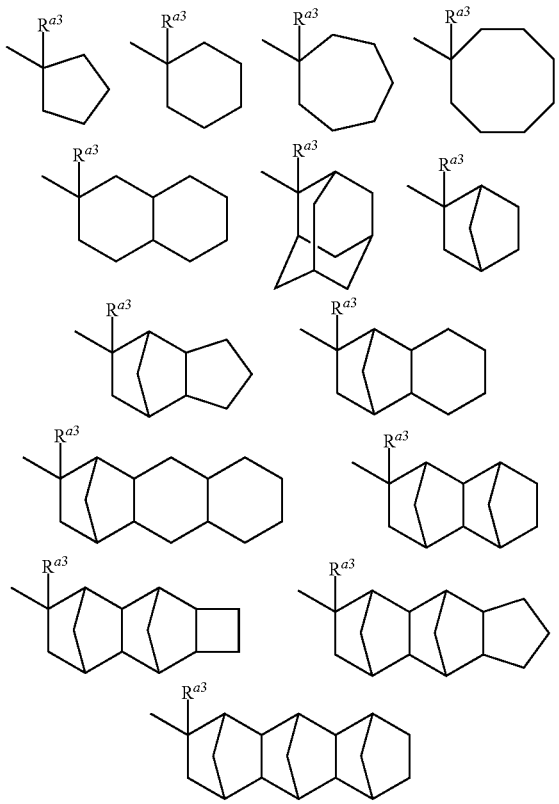

wherein $R^{a3}$ is the same as defined above.

The group represented by the formula (1) wherein $R^{a1}$, $R^{a2}$ and $R^{a3}$ independently each represent a C1-C8 alkyl group such as a tert-butyl group, the group represented by the formula (1) wherein $R^{a1}$ and $R^{a2}$ are bonded each other to form an adamantyl ring and $R^{a3}$ is a C1-C8 alkyl group such as a 2-alkyl-2-adamantyl group, and the group represented by the formula (1) wherein $R^{a1}$ and $R^{a2}$ are C1-C8 alkyl groups and $R^{a3}$ is an adamantyl group such as a 1-(1-adamantyl)-1-alkylalkoxycarbonyl group are preferable.

The compound having an acid-labile group is preferably an acrylate monomer having an acid-labile group in its side chain or a methacryalte monomer having an acid-labile group in its side chain.

Preferable examples of the compound having an acid-labile group include monomers represented by the formulae (a1-1) and (a1-2):

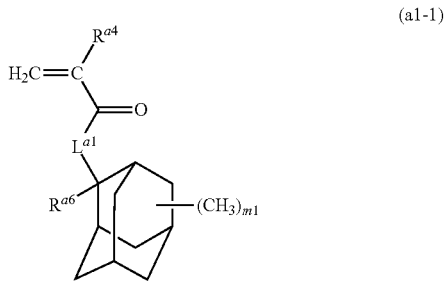

(a1-1)

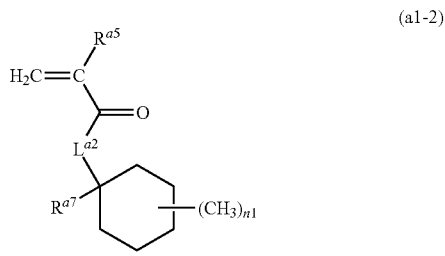

(a1-2)

wherein $R^{a4}$ and $R^{a5}$ each independently represents a hydrogen atom or a methyl group, $R^{a6}$ and $R^{a7}$ each independently represents a C1-C8 aliphatic hydrocarbon group or a C3-C10 saturated cyclic hydrocarbon group, $L^{a1}$ and $L^{a2}$ each independently represents *—O— or *—O—$(CH_2)_{k1}$—CO—O— in which * represents a binding position to —CO—, and k1 represents an integer of 1 to 7, m1 represents an integer of 0 to 14 and n1 represents an integer of 0 to 10.

The aliphatic hydrocarbon group preferably has 1 to 6 carbon atoms, and the saturated cyclic hydrocarbon group preferably has 3 to 8 carbon atoms and more preferably 3 to 6 carbon atoms.

Examples of the aliphatic hydrocarbon group include a C1-C8 alkyl group such as a methyl group, an ethyl group, a propyl group, an isopropyl group, a butyl group, a tert-butyl group, a 2,2-dimethylethyl group, a 1-methylpropyl group, a 2,2-dimethylpropyl group, a 1-ethylpropyl group, a 1-methylbutyl group, a 2-methylbutyl group, a 3-methylbutyl group, a 1-propylbutyl group, a pentyl group, a 1-methylpentyl group, a hexyl group, a 1,4-dimethylhexyl group, a heptyl group, a 1-methylheptyl group and an octyl group. Examples of the saturated cyclic hydrocarbon group include a cyclohexyl group, a methylcyclohexyl group, a dimethylcyclohexyl group, a cycloheptyl group, a methylcycloheptyl group, a norbornyl group and a methylnorbornyl group.

$L^{a1}$ is preferably *—O— or *—O—$(CH_2)_{f1}$—CO—O— in which * represents a binding position to —CO—, and f1 represents an integer of 1 to 4, and is more preferably *—O— or *—O—$CH_2$—CO—O—, and is especially preferably

*—O—. $L^{a2}$ is preferably *—O— or *—O—$(CH_2)_{f1}$—CO—O— in which * represents a binding position to —CO—, and f1 is the same as defined above, and is more preferably *—O— or *—O—$CH_2$—CO—O—, and is especially preferably *—O—.

In the formula (a1-1), m1 is preferably an integer of 0 to 3, and is more preferably 0 or 1. In the formula (a1-2), n1 is preferably an integer of 0 to 3, and is more preferably 0 or 1.

Particularly when the photoresist composition contains a resin derived from a monomer having a bulky structure such as a saturated cyclic hydrocarbon group, the photoresist composition having excellent resolution tends to be obtained.

Examples of the monomer represented by the formula (a1-1) include the followings.

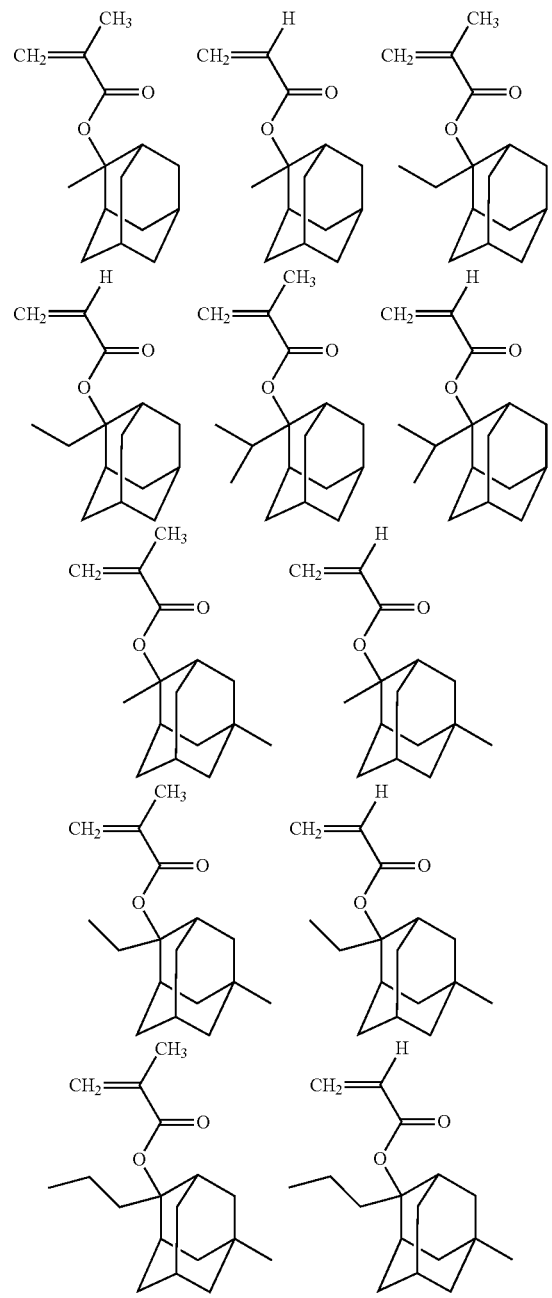

-continued

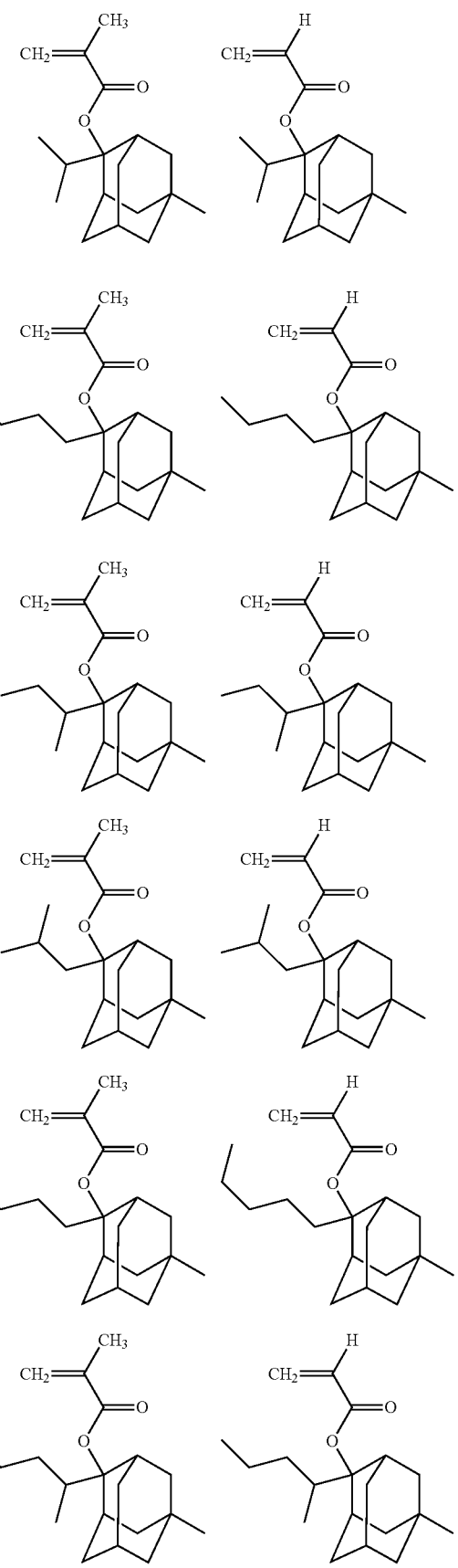

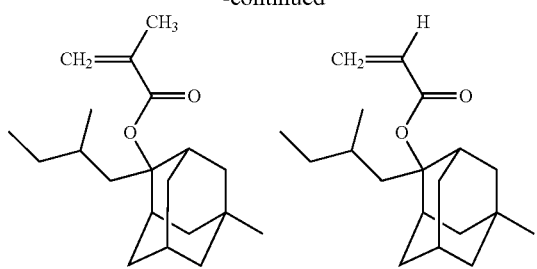
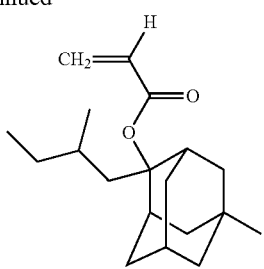
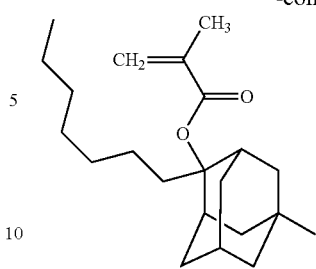
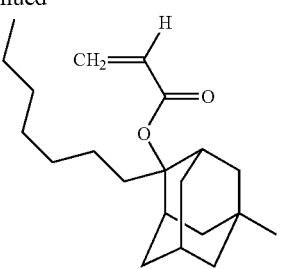
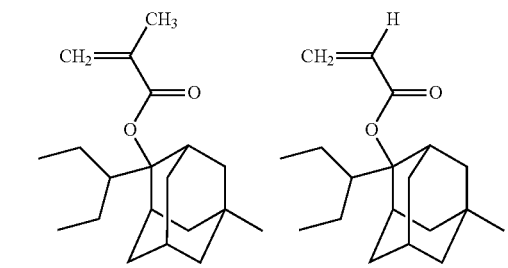
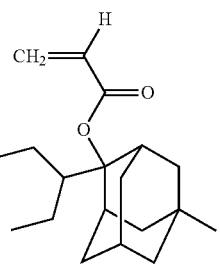
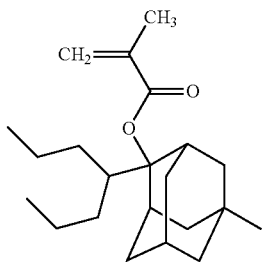
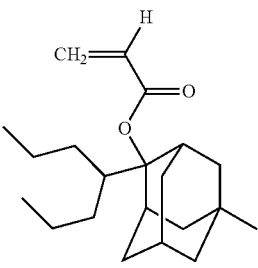
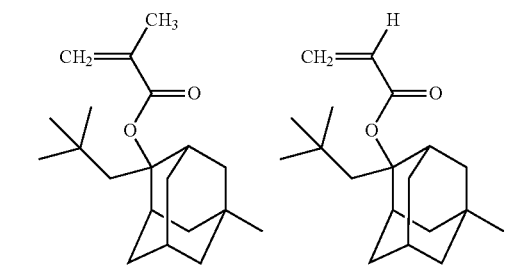
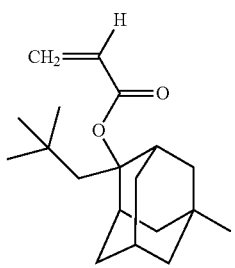
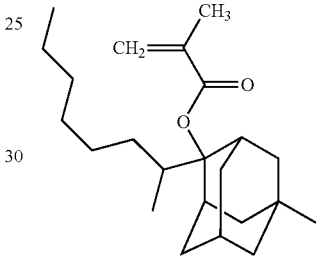
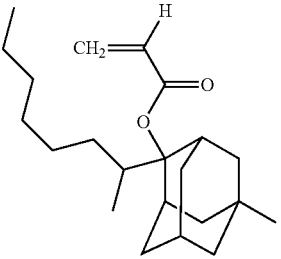
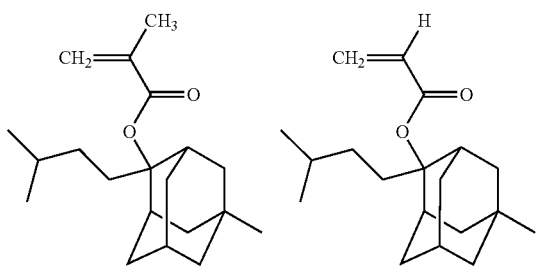
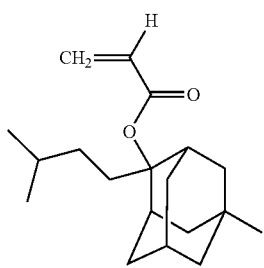
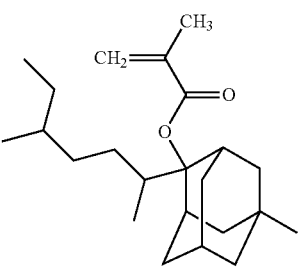
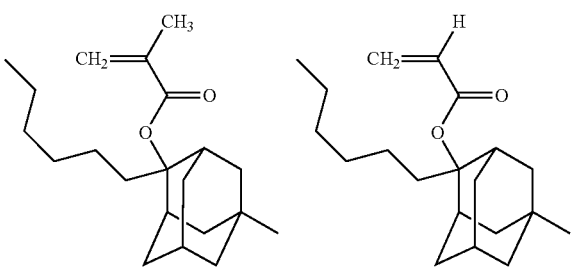
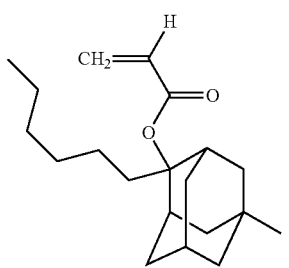
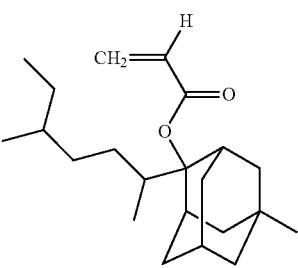
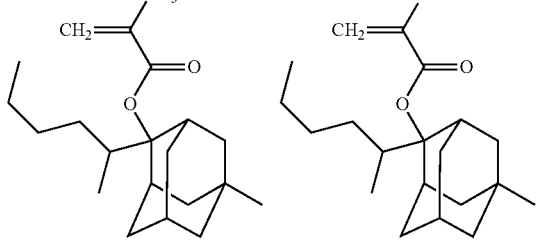
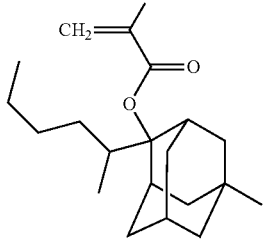
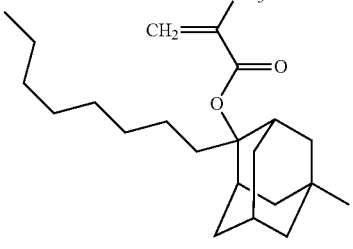

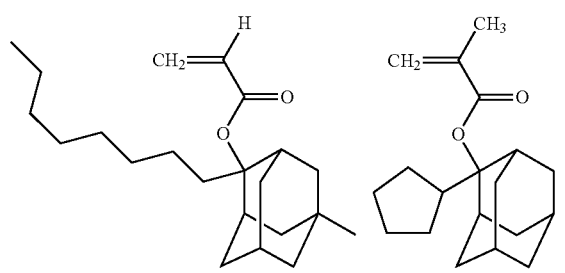
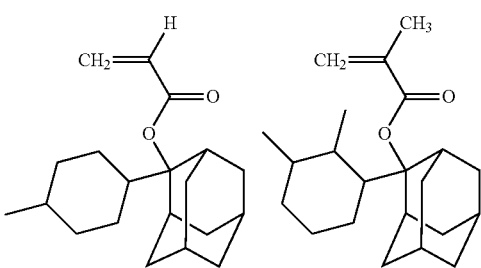
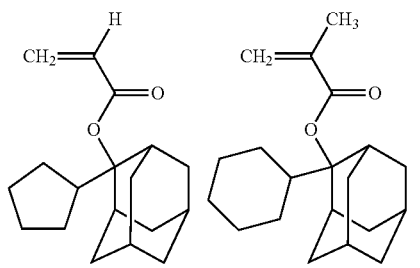
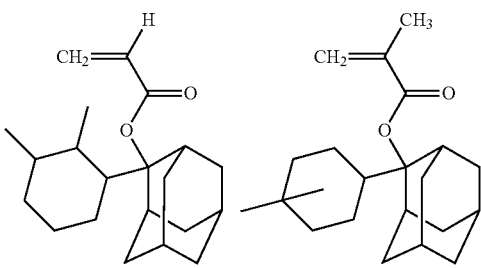
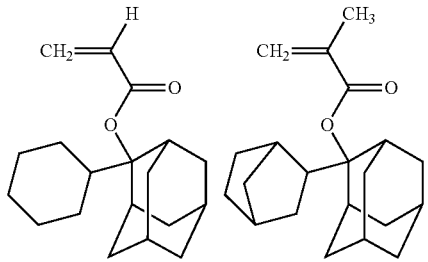
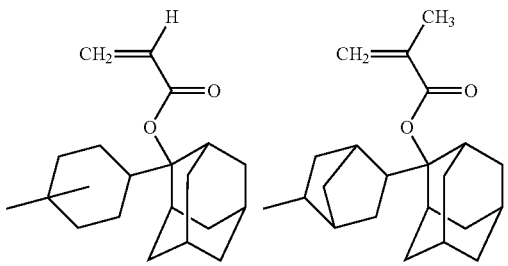
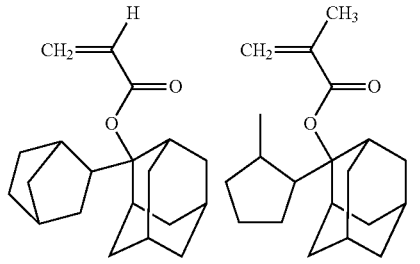
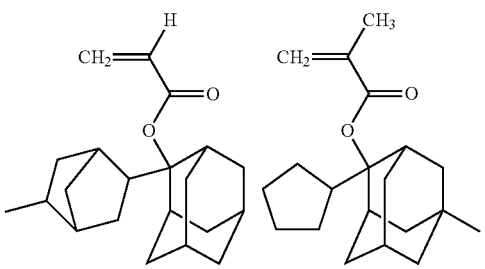
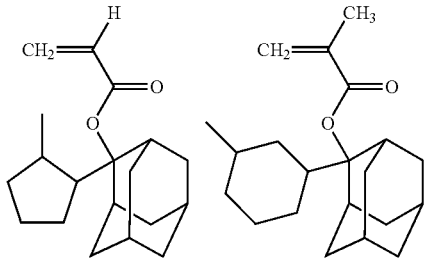
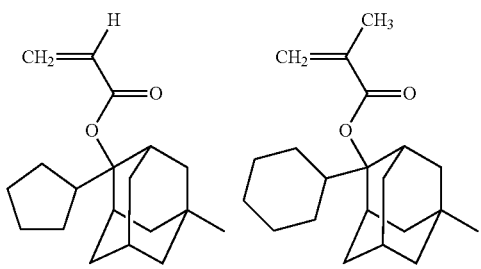
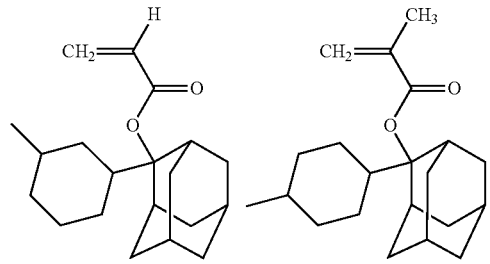
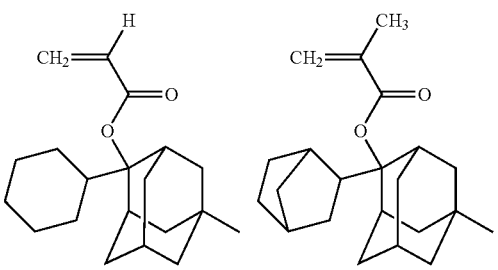

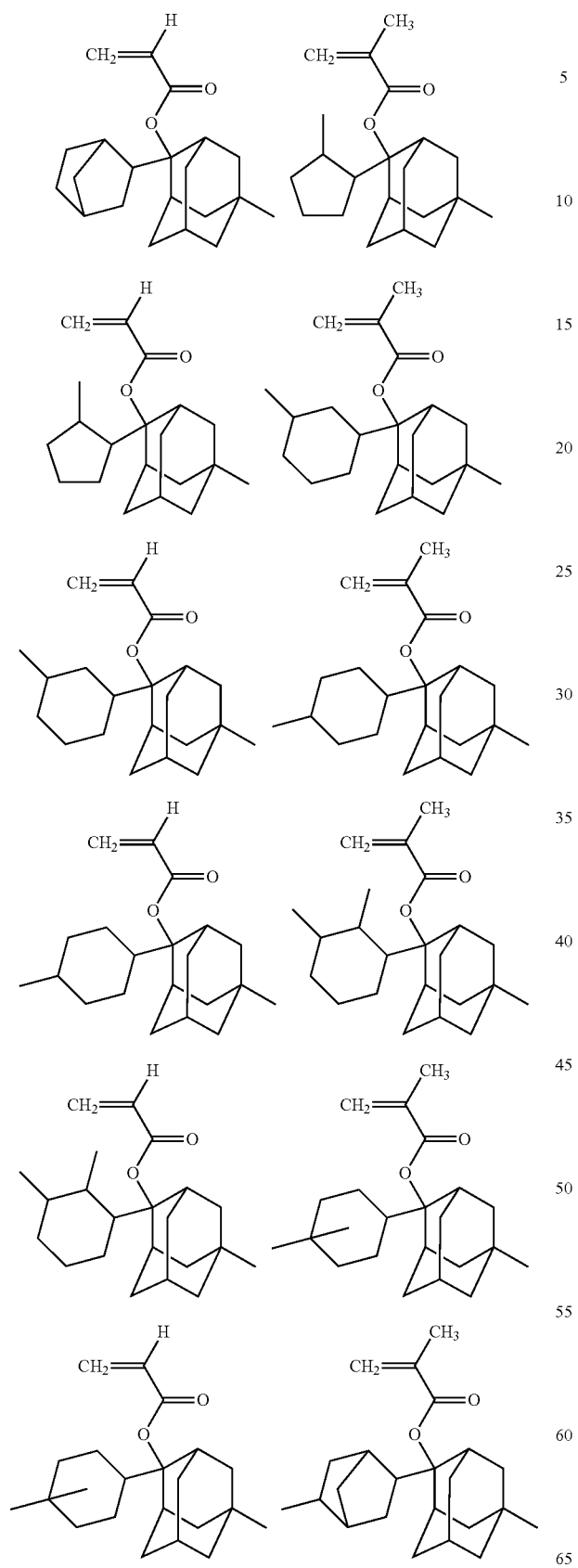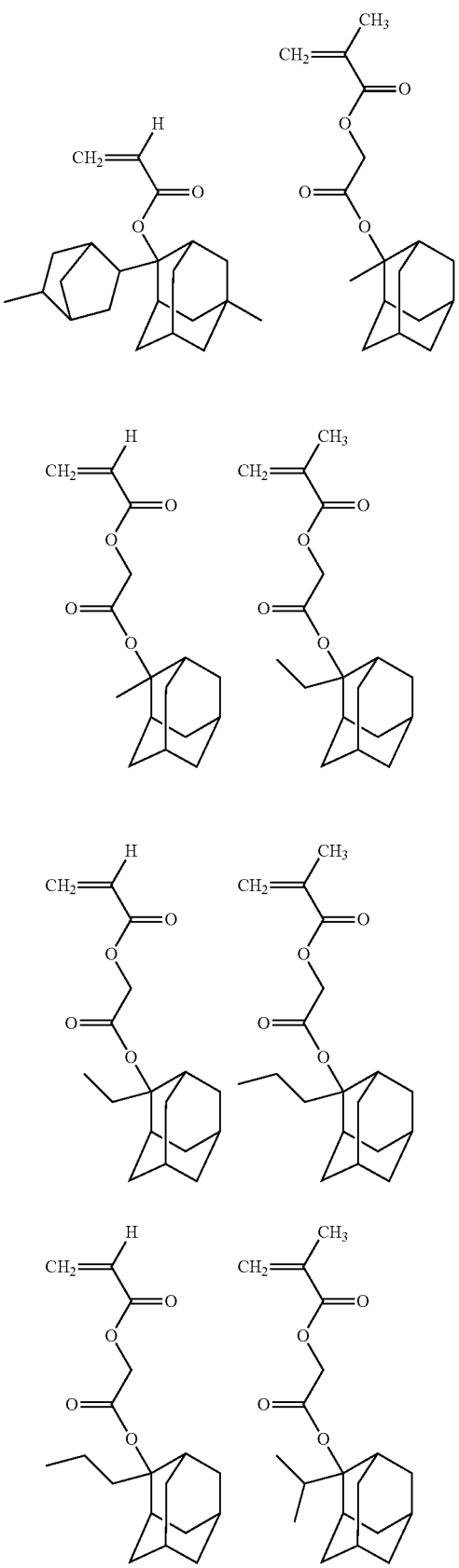

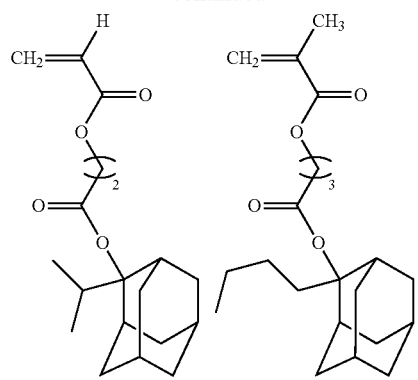
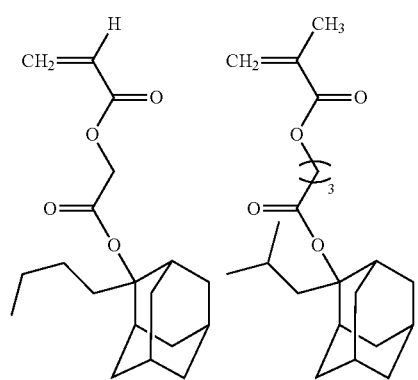
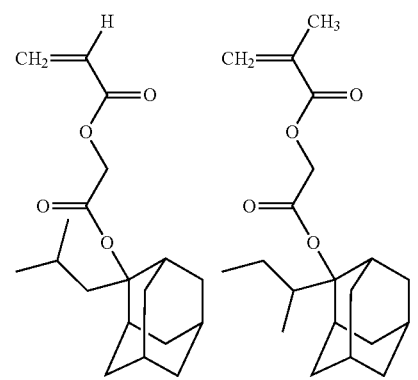
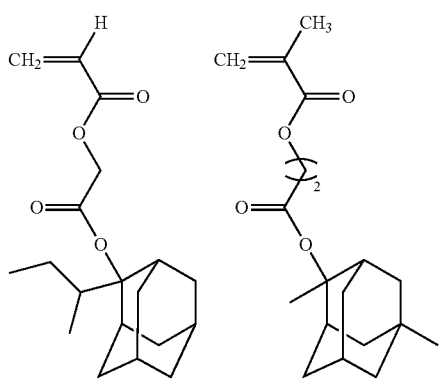
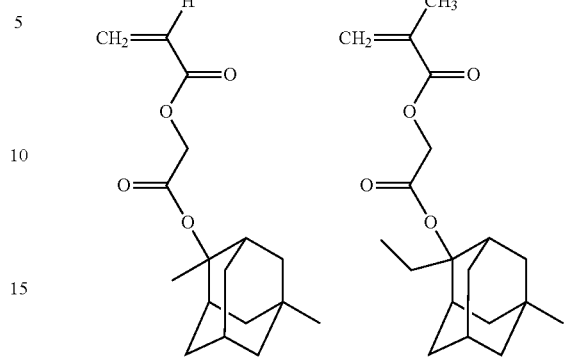
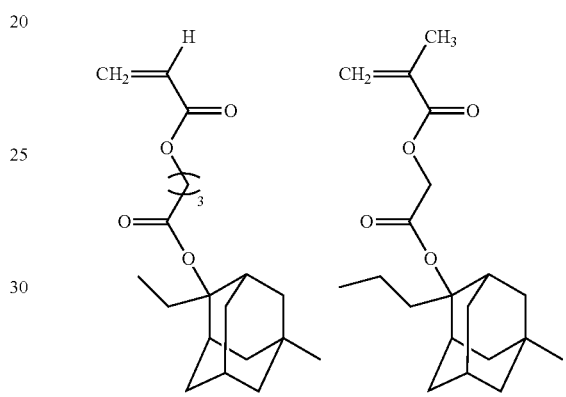
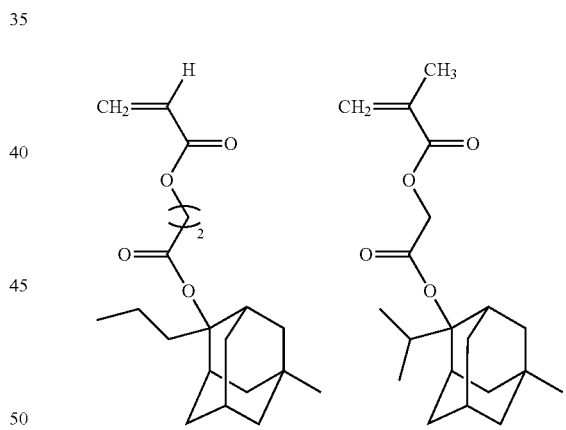
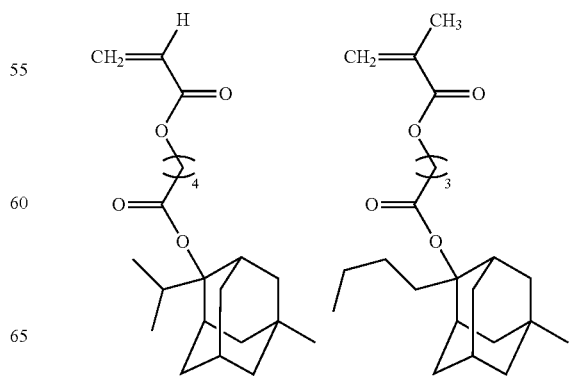

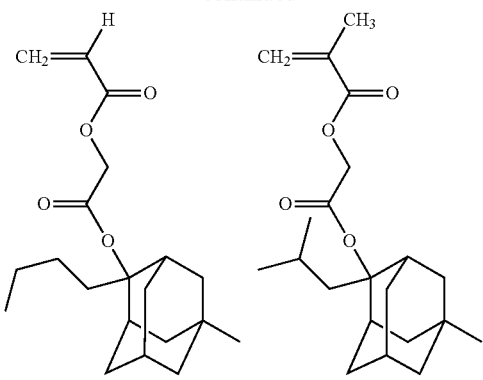
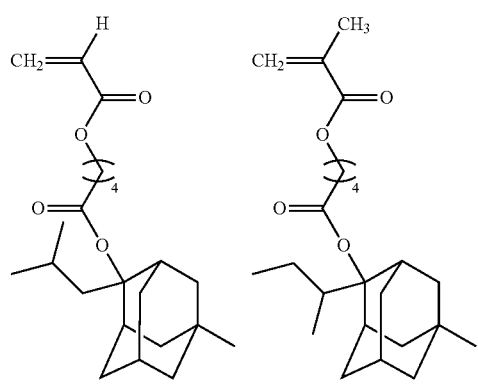
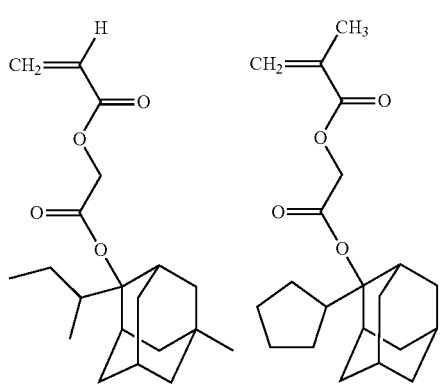
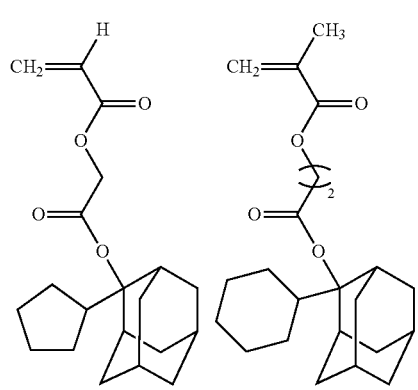
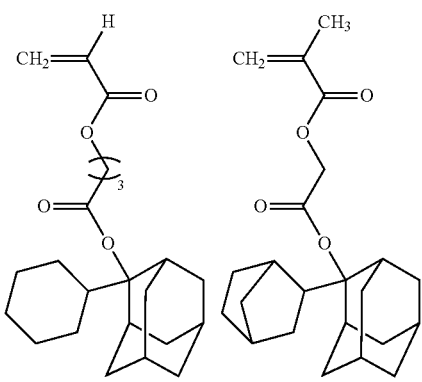
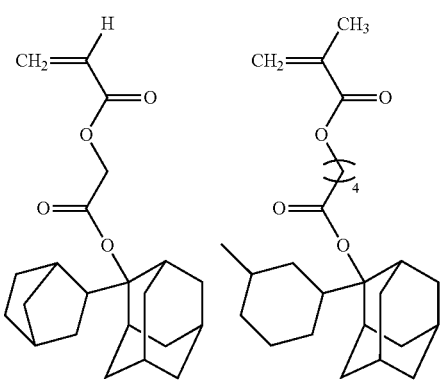
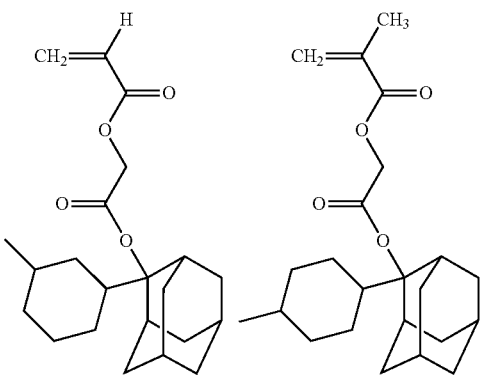
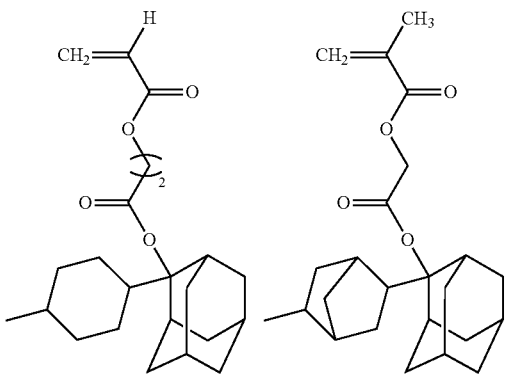

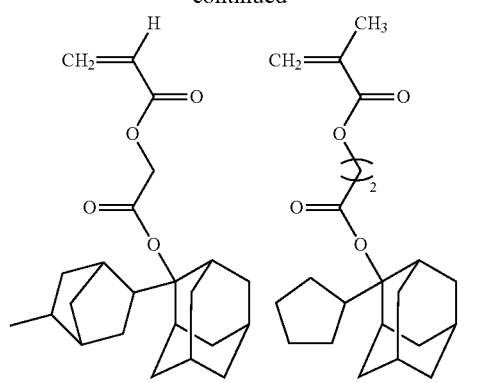
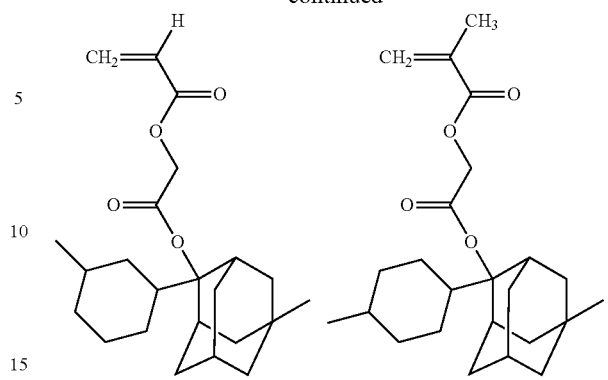
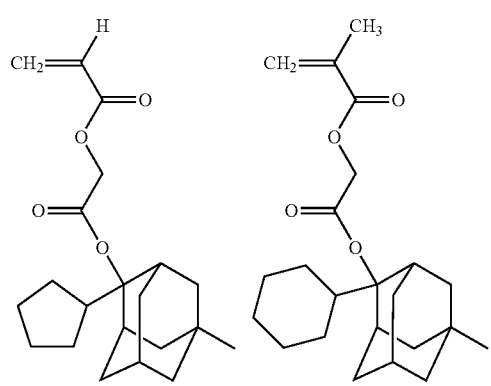
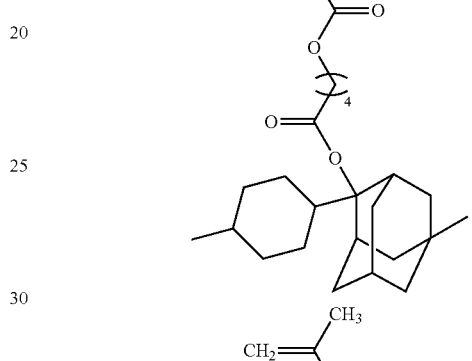
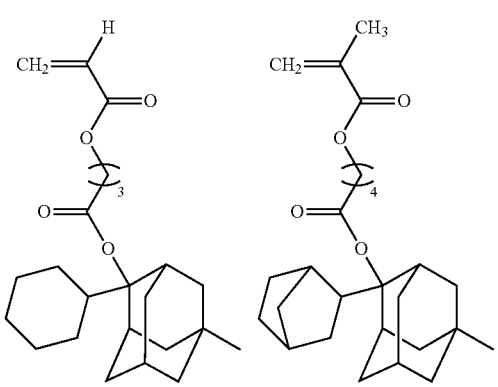
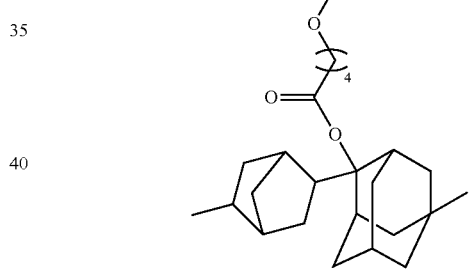
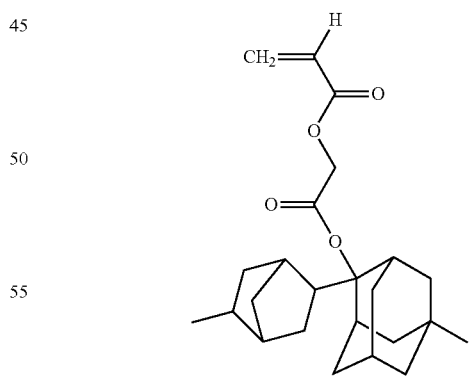
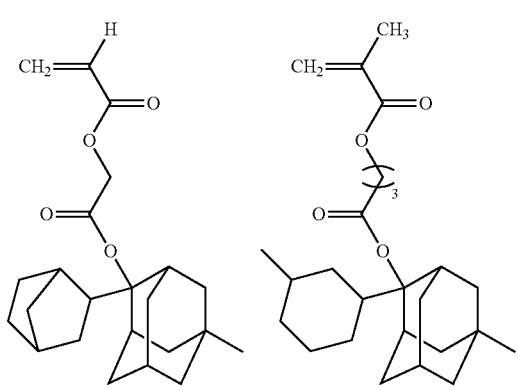
Among them, preferred are 2-methyl-2-adamantyl acrylate, 2-methyl-2-adamantyl methacrylate, 2-ethyl-2-adamantyl acrylate, 2-ethyl-2-adamantyl methacrylate, 2-isopropyl-2-adamantyl acrylate and 2-isopropyl-2-adamantyl methacrylate, and more preferred are 2-methyl-2-adamantyl methacrylate, 2-ethyl-2-adamantyl methacrylate, and 2-isopropyl-2-adamantyl methacrylate.

Examples of the monomer represented by the formula (a1-2) include the followings.

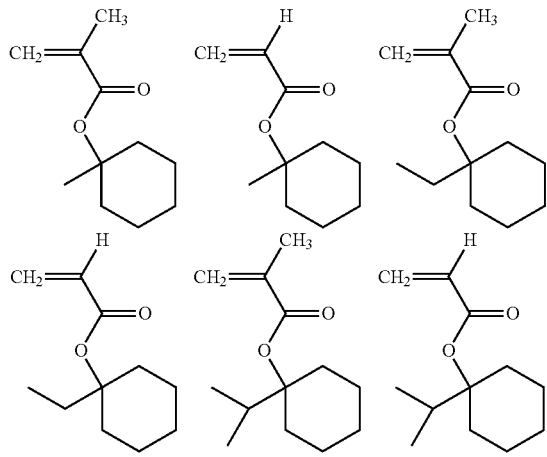

Among them, preferred are 1-ethyl-1-cyclohexyl acrylate and 1-ethyl-1-cyclohexyl methacrylate, and more preferred is 1-ethyl-1-cyclohexyl methacrylate.

The content of the structural unit derived from a compound having an acid-labile group in the resin is usually 10 to 95% by mole, preferably 15 to 90% by mole and more preferably 20 to 85% by mole based on 100% by mole of all the structural units of the resin.

Other examples of the compound having an acid-labile group include a monomer represented by the formula (a1-3):

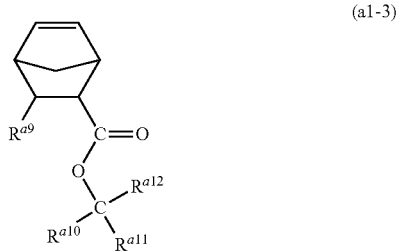

(a1-3)

wherein $R^{a9}$ represents a hydrogen atom, a C1-C3 aliphatic hydrocarbon group which can have one or more substituents, a carboxyl group, a cyano group or a —COOR$^{a13}$ group in which $R^{a13}$ represents a C1-C8 aliphatic hydrocarbon group or a C3-C8 saturated cyclic hydrocarbon group, and the C1-C8 aliphatic hydrocarbon group and the C3-C8 saturated cyclic hydrocarbon group can have one or more hydroxyl groups, and one or more —CH$_2$— in the C1-C8 aliphatic hydrocarbon group and the C3-C8 saturated cyclic hydrocarbon group can be replaced by —O— or —CO—, $R^{a10}$, $R^{a11}$ and $R^{a12}$ each independently represent a C1-C12 aliphatic hydrocarbon group or a C3-C12 saturated cyclic hydrocarbon group, and $R^{a10}$ and $R^{a11}$ can be bonded each other to form a ring together with the carbon atom to which $R^{a10}$ and $R^{a11}$ are bonded, and the C1-C12 aliphatic hydrocarbon group and the C3-C12 saturated cyclic hydrocarbon group can have one or more hydroxyl groups, and one or more —CH$_2$— in the C1-C12 aliphatic hydrocarbon group and the C3-C12 saturated cyclic hydrocarbon group can be replaced by —O— or —CO—.

Examples of the substituent include a hydroxyl group. Examples of the C1-C3 aliphatic hydrocarbon group which can have one or more substituents include a methyl group, an ethyl group, a propyl group, a hydroxymethyl group and a 2-hydroxyethyl group.

Examples of $R^{a13}$ include a methyl group, an ethyl group, a propyl group, a 2-oxo-oxolan-3-yl group and a 2-oxo-oxolan-4-yl group. Examples of $R^{a10}$, $R^{a11}$ and $R^{a12}$ include a methyl group, an ethyl group, a cyclohexyl group, a methylcyclohexyl group, a hydroxycyclohexyl group, an oxocyclohexyl group and an adamantyl group, and examples of the ring formed by bonding $R^{a10}$ and $R^{a11}$ each other together with the carbon atom to which $R^{a10}$ and $R^{a11}$ are bonded include a cyclohexane ring and an adamantane ring.

Examples of the monomer represented by the formula (a1-3) include tert-butyl 5-norbornene-2-carboxylate, 1-cyclohexyl-1-methylethyl 5-norbornene-2-carboxylate, 1-methylcyclohexyl 5-norbornene-2-carboxylate, 2-methyl-2-adamantyl 5-norbornene-2-carboxylate, 2-ethyl-2-adamantyl 5-norbornene-2-carboxylate, 1-(4-methylcyclohexyl)-1-methylethyl 5-norbornene-2-carboxylate, 1-(4-hydroxycyclohexyl)-1-methylethyl 5-norbornene-2-carboxylate, 1-methyl-1-(4-oxocyclohexyl) ethyl 5-norbornene-2-carboxylate and 1-(1-adamantyl)-1-methylethyl 5-norbornene-2-carboxylate.

When the resin has a structural unit derived from the monomer represented by the formula (a1-3), the photoresist composition having excellent resolution and higher dry-etching resistance tends to be obtained.

When the resin contains the structural unit derived form the monomer represented by the formula (a1-3), the content of the structural unit derived from the monomer represented by the formula (a1-3) is usually 10 to 95% by mole and preferably 15 to 90% by mole and more preferably 20 to 85% by mole based on total molar of all the structural units of the resin.

Other examples of the compound having an acid-labile group include a monomer represented by the formula (a1-4):

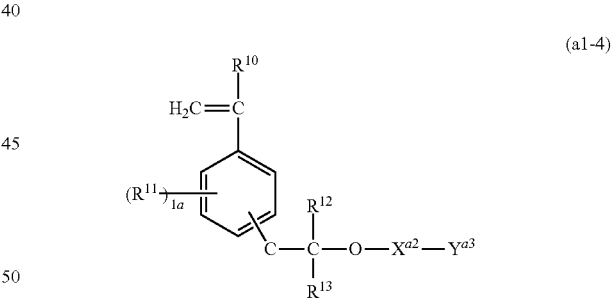

(a1-4)

wherein $R^{10}$ represents a hydrogen atom, a halogen atom, a C1-C6 alkyl group or a C1-C6 halogenated alkyl group, $R^{11}$ is independently in each occurrence a halogen atom, a hydroxyl group, a C1-C6 alkyl group, a C1-C6 alkoxy group, a C2-C4 acyl group, a C2-C4 acyloxy group, an acryloyl group or a methacryloyl group, 1a represents an integer of 0 to 4, $R^{12}$ and $R^{13}$ each independently represent a hydrogen atom or a C1-C12 hydrocarbon group, $X^{a2}$ represents a single bond or a C1-C17 divalent saturated hydrocarbon group in which one or more —CH$_2$— can be replaced by —O—, —CO—, —S—, —SO$_2$— or —N(R$^c$)— wherein R$^c$ represents a hydrogen atom or a C1-C6 alkyl group, and $Y^{a3}$ represents a C1-C12 aliphatic hydrocarbon group, a C3-C18 saturated cyclic hydrocarbon group or a C6-C18 aromatic hydrocarbon group, and the C1-C12 aliphatic hydrocarbon group, the C2-C18 saturated cyclic hydrocarbon group and the C6-C18 aromatic hydrocarbon group can have one or more substituents.

Examples of the halogen atom include a fluorine atom.

Examples of the C1-C6 alkyl group include a methyl group, an ethyl group, a propyl group, an isopropyl group, a butyl group, an isobutyl group, a sec-butyl group, a tert-butyl group, a pentyl group and a hexyl group, and a C1-C4 alkyl group is preferable and a C1-C2 alkyl group is more preferable and a methyl group is especially preferable.

Examples of the C1-C6 halogenated alkyl group include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group and a perfluorohexyl group.

Examples of the C1-C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group, and a C1-C4 alkoxy group is preferable and a C1-C2 alkoxy group is more preferable and a methoxy group is especially preferable.

Examples of the C2-C4 acyl group include an acetyl group, a propionyl group and a butyryl group, and examples of the C2-C4 acyloxy group include an acetyloxy group, a propionyloxy group and a butyryloxy group.

Examples of the C1-C12 hydrocarbon group include a C1-C12 aliphatic hydrocarbon group such as a methyl group, an ethyl group, a propyl group, an isopropyl group, a butyl group, an isobutyl group, a sec-butyl group, a tert-butyl group, a pentyl group, a hexyl group, a heptyl group, an octyl group, a 2-ethylhexyl group, a nonyl group, a decyl group, an undecyl group and a dodecyl group, and a C3-C12 saturated cyclic hydrocarbon group such as a cyclohexyl group, an adamantyl group, a 2-alkyl-2-adamantyl group, a 1-(1-adamantyl)-1-alkyl group and an isobornyl group.

Examples of the C1-C17 divalent saturated hydrocarbon group include a C1-C17 alkanediyl group such as a methylene group, an ethylene group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, a undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group and a heptadecane-1,17-diyl group.

Examples of the C1-C12 aliphatic hydrocarbon group include a methyl group, an ethyl group, a propyl group, an isopropyl group, a butyl group, an isobutyl group, a sec-butyl group, a tert-butyl group, a pentyl group, a hexyl group, a heptyl group, an octyl group, a 2-ethylhexyl group, a nonyl group, a decyl group, an undecyl group and a dodecyl group. Examples of the C3-C18 saturated cyclic hydrocarbon group include a cyclopropyl group, a cyclobutyl group, a cyclopentyl group, a cyclohexyl group, a cycloheptyl group, a cyclooctyl group, a cyclononyl group, a cyclodecyl group, a norbornyl group, a 1-adamantyl group, a 2-adamantyl group, an isobornyl group and the following groups:

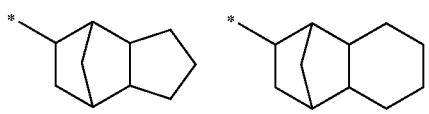

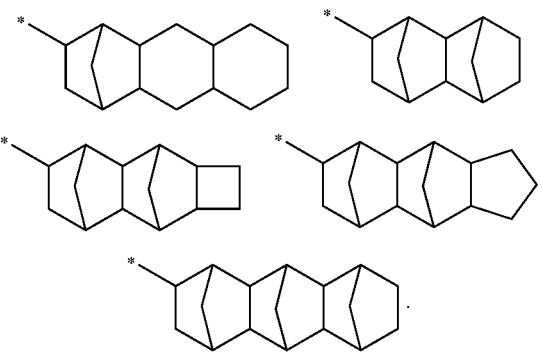

Examples of the C6-C18 aromatic hydrocarbon group include a phenyl group, a naphthyl group, an anthryl group, a p-methylphenyl group, a p-tert-butylphenyl group and a p-adamantylphenyl group.

Examples of the monomer represented by the formula (a1-4) include the followings.

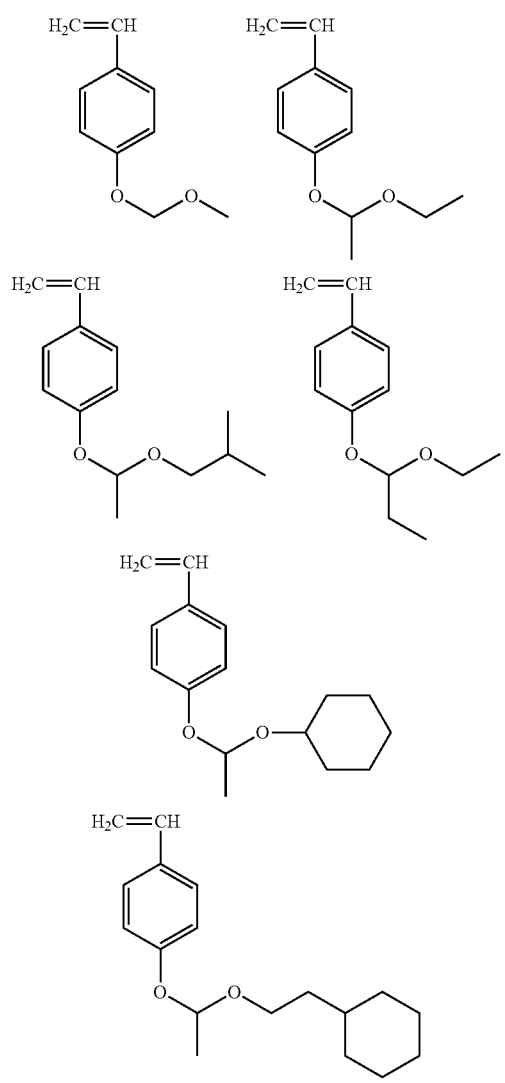

-continued
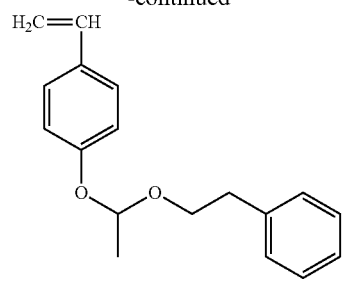
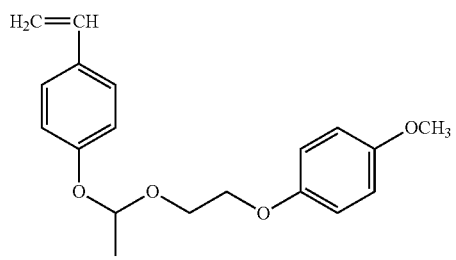
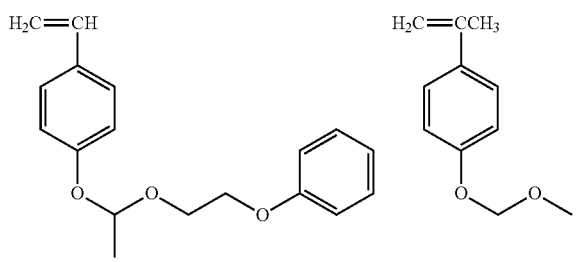
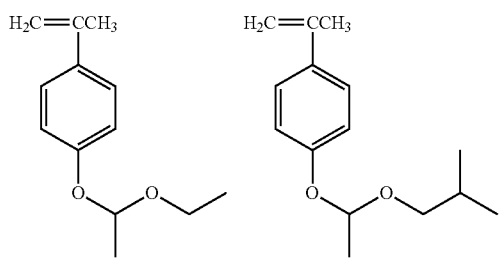
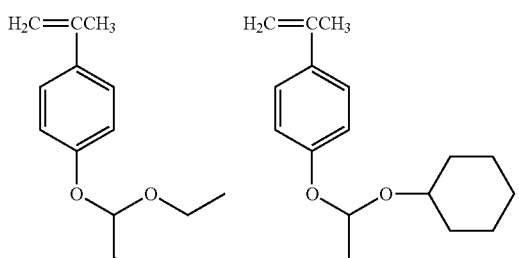
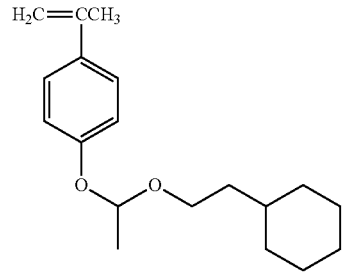
-continued
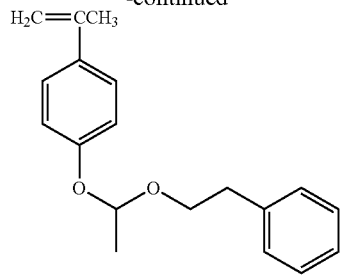
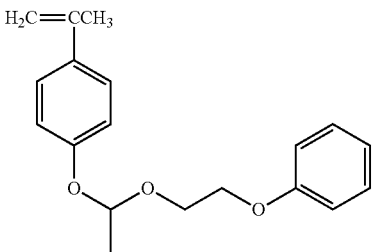
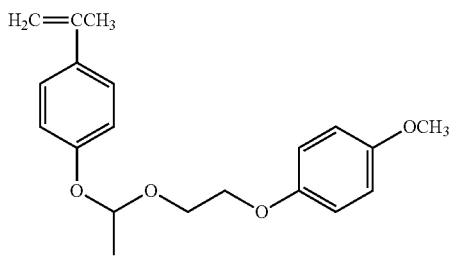
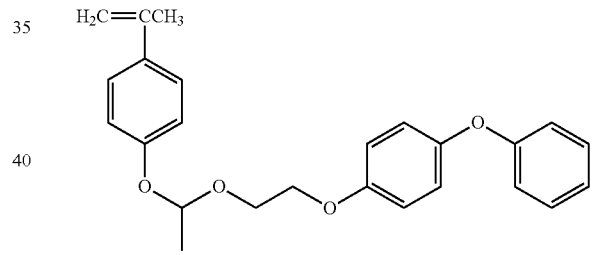
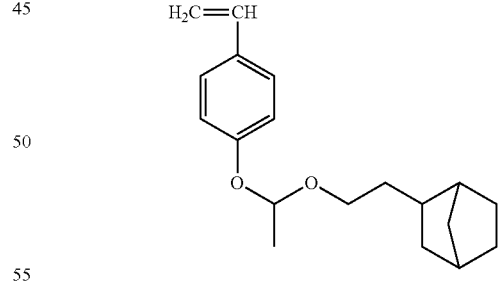
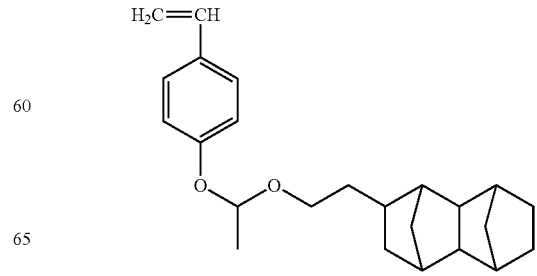

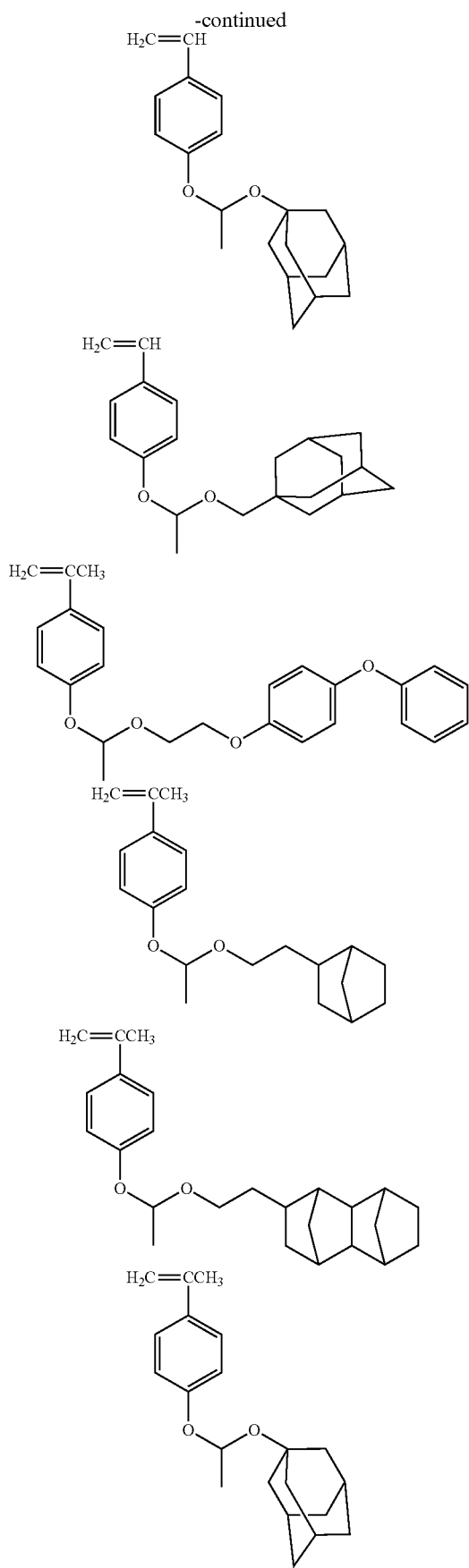
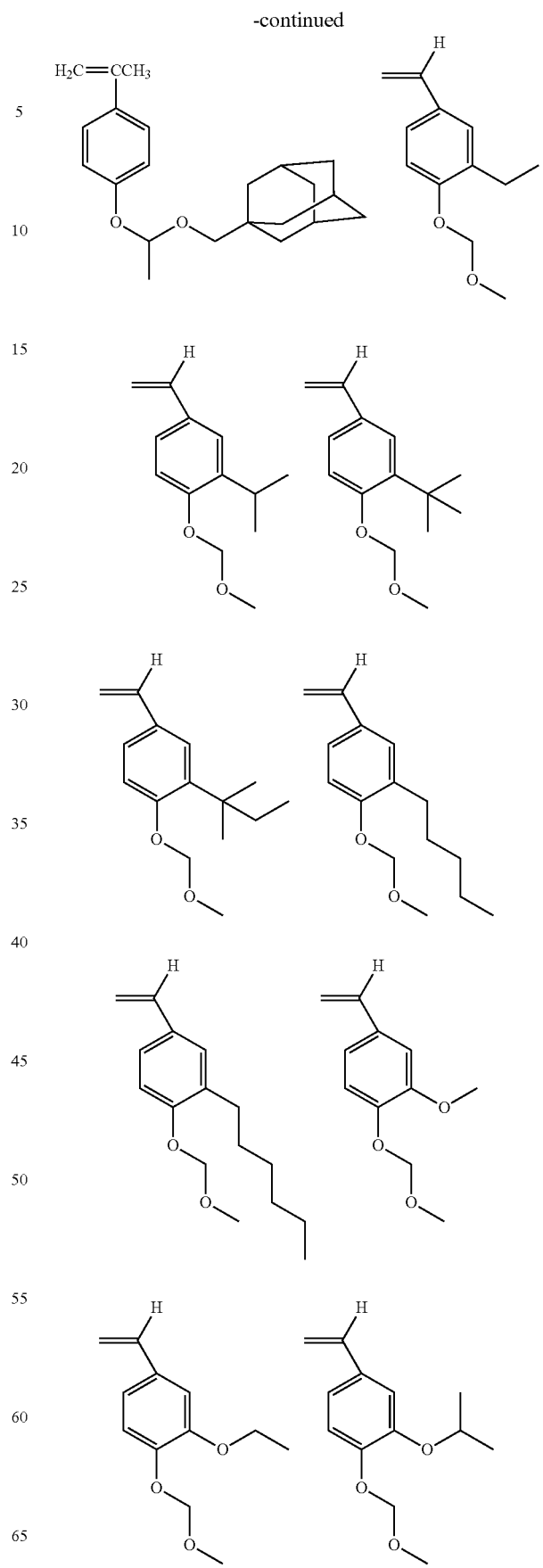

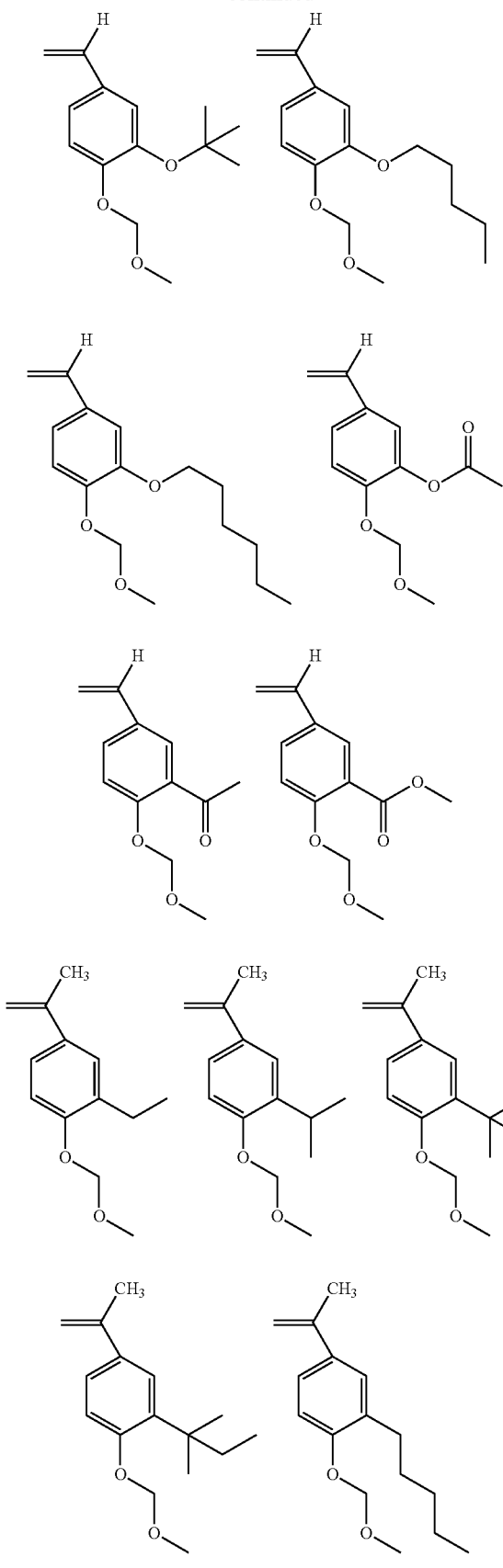
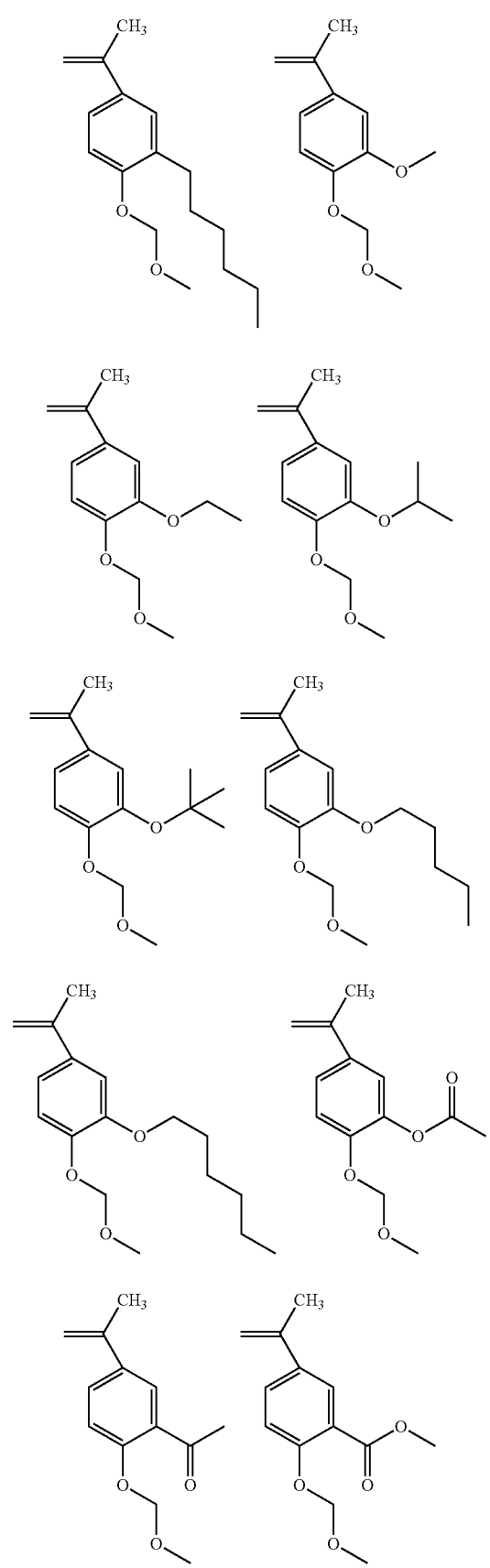

-continued

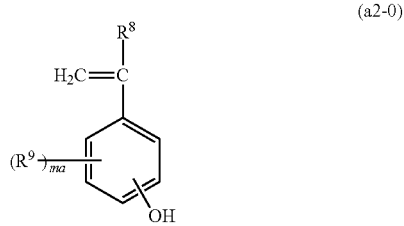

When the resin contains the structural unit derived form the monomer represented by the formula (a1-4), the content of the structural unit derived from the monomer represented by the formula (a1-4) is usually 10 to 95% by mole and preferably 15 to 90% by mole and more preferably 20 to 85% by mole based on total molar of all the structural units of the resin.

The resin can have two or more kinds of structural units derived from the compounds having an acid-labile group.

The resin preferably contains the structural unit derived from the compound having an acid-labile group and a structural unit derived from the compound having no acid-labile group. The resin can have two or more kinds of structural units derived from the compounds having no acid-labile group. When the resin contains the structural unit derived from the compound having an acid-labile group and the structural unit derived from the compound having no acid-labile group, the content of the structural unit derived from the compound having an acid-labile group is usually 10 to 80% by mole and preferably 20 to 60% by mole based on total molar of all the structural units of the resin. The content of the structural unit derived from a monomer having an adamantyl group, especially the monomer represented by the formula (a1-1) in the structural unit derived from the compound having no acid-labile group is preferably 15% by mole or more from the viewpoint of dry-etching resistance of the photoresist composition.

The compound having no acid-labile group preferably contains one or more hydroxyl groups or a lactone ring. When the resin contains the structural unit derived from the compound having no acid-labile group and having one or more hydroxyl groups or a lactone ring, a photoresist composition having good resolution and adhesiveness of photoresist to a substrate tends to be obtained.

Examples of the compound having no acid-labile group and having one or more hydroxyl groups include a monomer represented by the formula (a2-0):

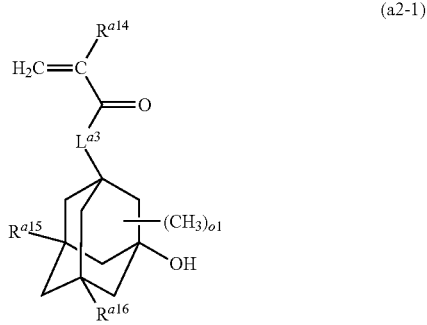

wherein $R^8$ represents a hydrogen atom, a halogen atom, a C1-C6 alkyl group or a C1-C6 halogenated alkyl group, $R^9$ is independently in each occurrence a halogen atom, a hydroxyl group, a C1-C6 alkyl group, a C1-C6 alkoxy group, a C2-C4 acyl group, a C2-C4 acyloxy group, an acryloyl group or a methacryloyl group, ma represents an integer of 0 to 4, and a monomer represented by the formula (a2-1):

wherein $R^{a14}$ represents a hydrogen atom or a methyl group, $R^{a15}$ and $R^{a16}$ each independently represent a hydrogen atom, a methyl group or a hydroxyl group, $L^{a3}$ represents *—O— or *—O—$(CH_2)_{k2}$—CO—O— in which * represents a binding position to —CO—, and k2 represents an integer of 1 to 7, and o1 represents an integer of 0 to 10.

When KrF excimer laser (wavelength: 248 nm) lithography system, or a high energy laser such as electron beam and extreme ultraviolet is used as an exposure system, the resin containing the structural unit derived from the monomer represented by the formula (a2-0) is preferable, and when ArF excimer laser (wavelength: 193 nm) is used as an exposure system, the resin containing the structural unit derived from the monomer represented by the formula (a2-1) is preferable.

In the formula (a2-0), examples of the halogen atom include a fluorine atom, examples of the C1-C6 alkyl group include a methyl group, an ethyl group, a propyl group, an isopropyl group, a butyl group, an isobutyl group, a sec-butyl group, a tert-butyl group, a pentyl group and a hexyl group, and a C1-C4 alkyl group is preferable and a C1-C2 alkyl group is more preferable and a methyl group is especially preferable. Examples of the C1-C6 halogenated alkyl group include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group and a perfluorohexyl group. Examples of the C1-C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group, and a C1-C4 alkoxy group is preferable and a C1-C2 alkoxy group is more preferable and a methoxy group is especially preferable. Examples of the C2-C4 acyl group include an acetyl group, a propionyl group and a butyryl group, and examples of the C2-C4 acyloxy group include an acetyloxy group, a propionyloxy group and a butyryloxy group. In the formula (a2-0), ma is preferably 0, 1 or 2, and is more preferably 0 or 1, and especially preferably 0.

The resin containing the structural unit derived from the monomer represented by the formula (a2-0) and the structural unit derived from the compound having an acid generator can be produced, for example, by polymerizing the compound having an acid generator and a monomer obtained by protecting a hydroxyl group of the monomer represented by the formula (a2-0) with an acetyl group followed by conducting deacetylation of the obtained polymer with a base.

Examples of the monomer represented by the formula (a2-0) include the followings.

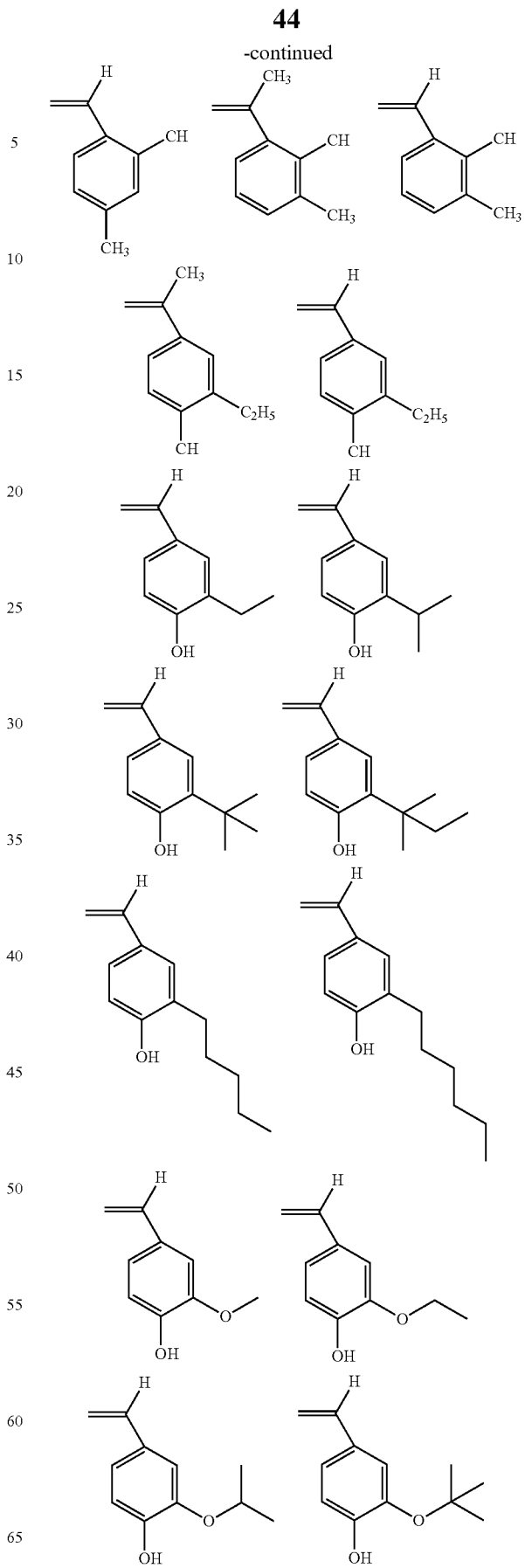

-continued

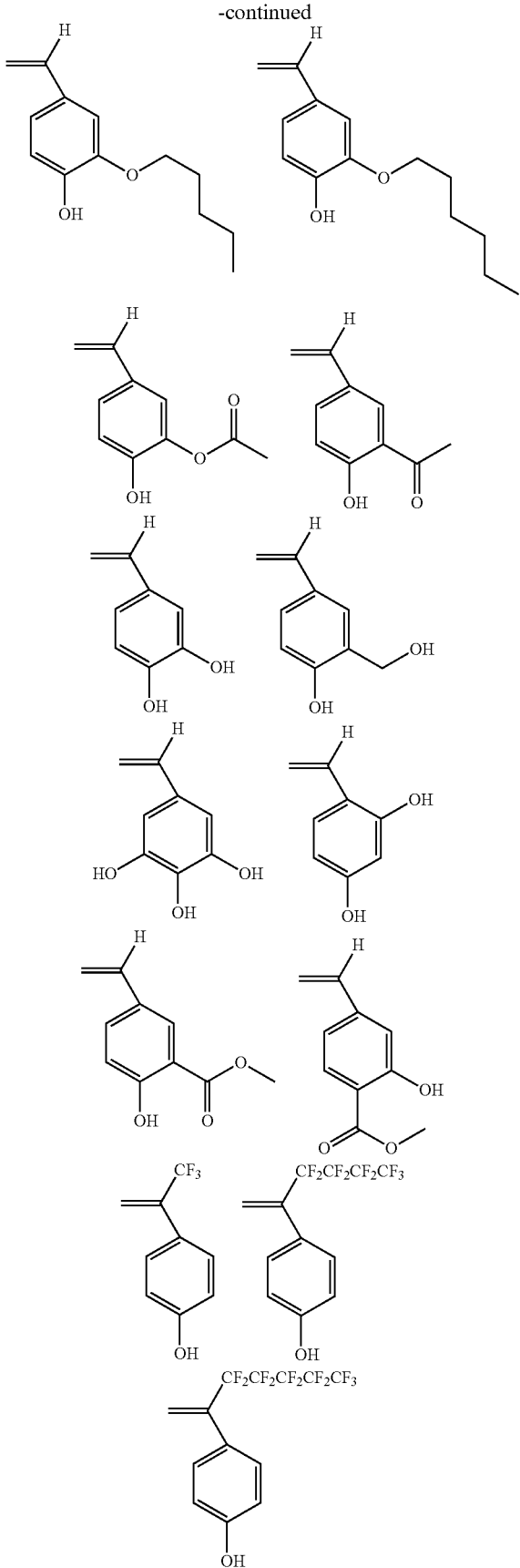

Among them, preferred are 4-hydroxystyrene and 4-hydroxy-α-methylstyrene.

When the resin contains the structural unit derived from the monomer represented by the formula (a2-0), the content of the structural unit derived from the monomer represented by the formula (a2-0) is usually 5 to 90% by mole and preferably 10 to 85% by mole and more preferably 15 to 80% by mole based on total molar of all the structural units of the resin.

In the formula (a2-1), $R^{a14}$ is preferably a methyl group, $R^{a15}$ is preferably a hydrogen atom, $R^{a16}$ is preferably a hydrogen atom or a hydroxyl group, $L^{a3}$ is preferably *—O— or *—O—$(CH_2)_{f2}$—CO—O— in which * represents a binding position to —CO—, and f2 represents an integer of 1 to 4, and is more preferably *—O—, and o1 is preferably 0, 1, 2 or 3 and is more preferably 0 or 1.

Examples of the monomer represented by the formula (a2-1) include the followings, and 3-hydroxy-1-adamantyl acrylate, 3-hydroxy-1-adamantyl methacrylate, 3,5-dihydroxy-1-adamantyl acrylate, 3,5-dihydroxy-1-adamantyl methacrylate, 1-(3,5-dihydroxy-1-adamantyloxycarbonyl)methyl acrylate and 1-(3,5-dihydroxy-1-adamantyloxycarbonyl)methyl methacrylate are preferable, and 3-hydroxy-1-adamantyl methacrylate and 3,5-dihydroxy-1-adamantyl methacrylate are more preferable.

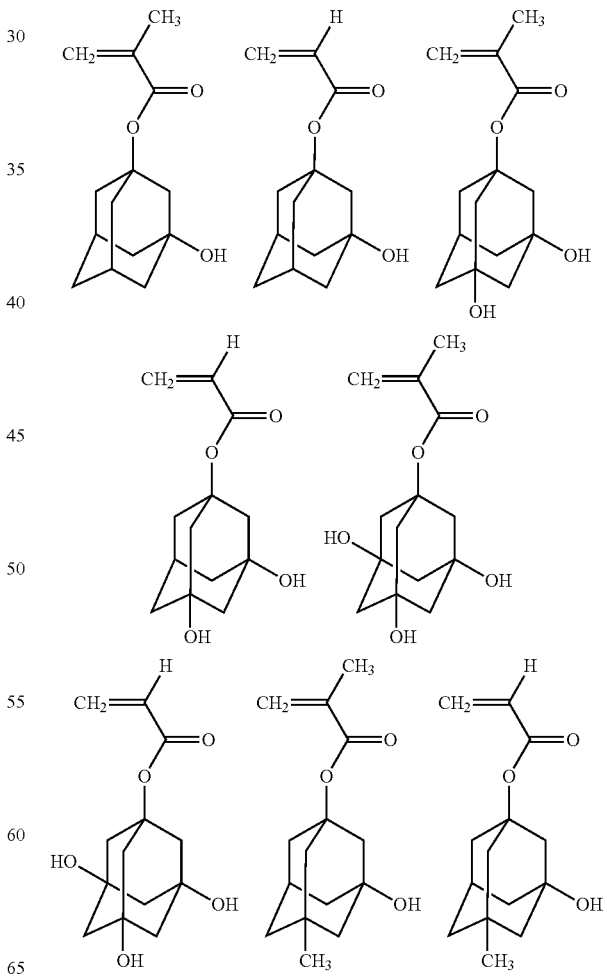

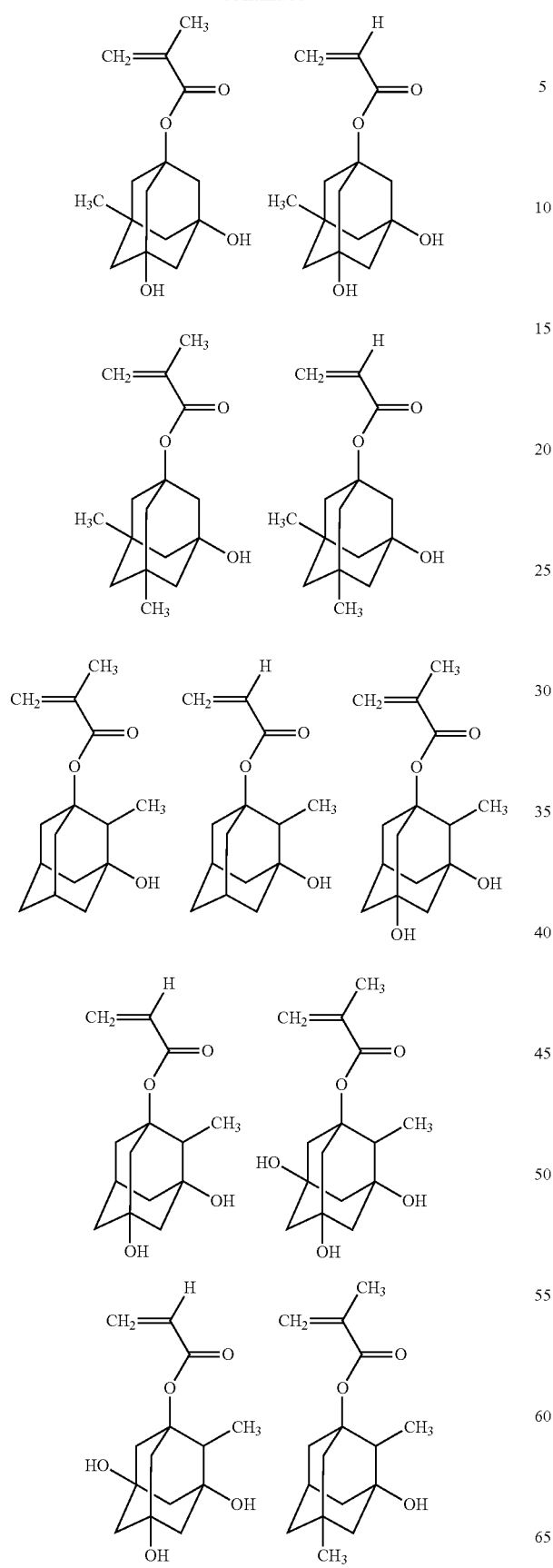
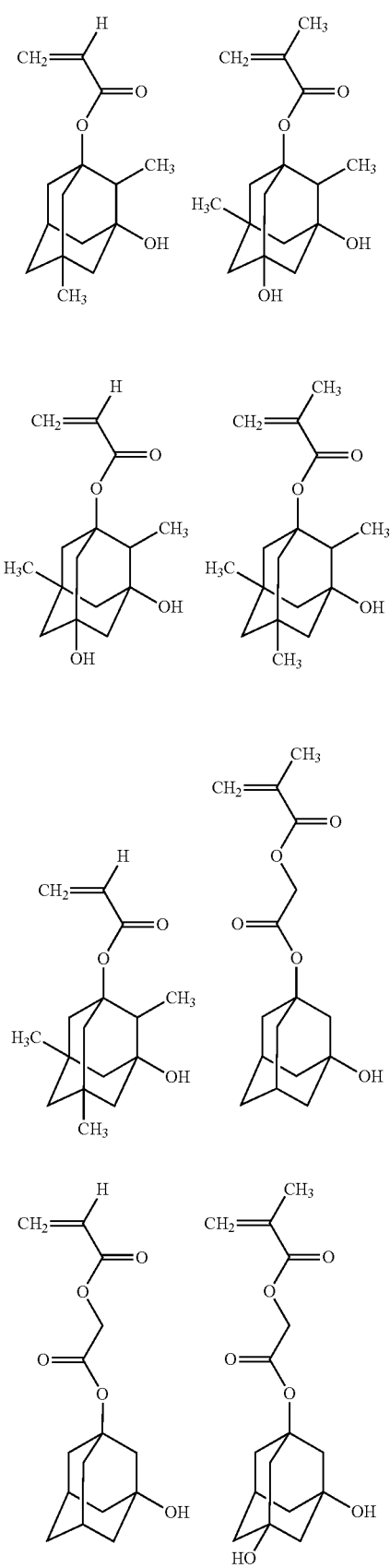

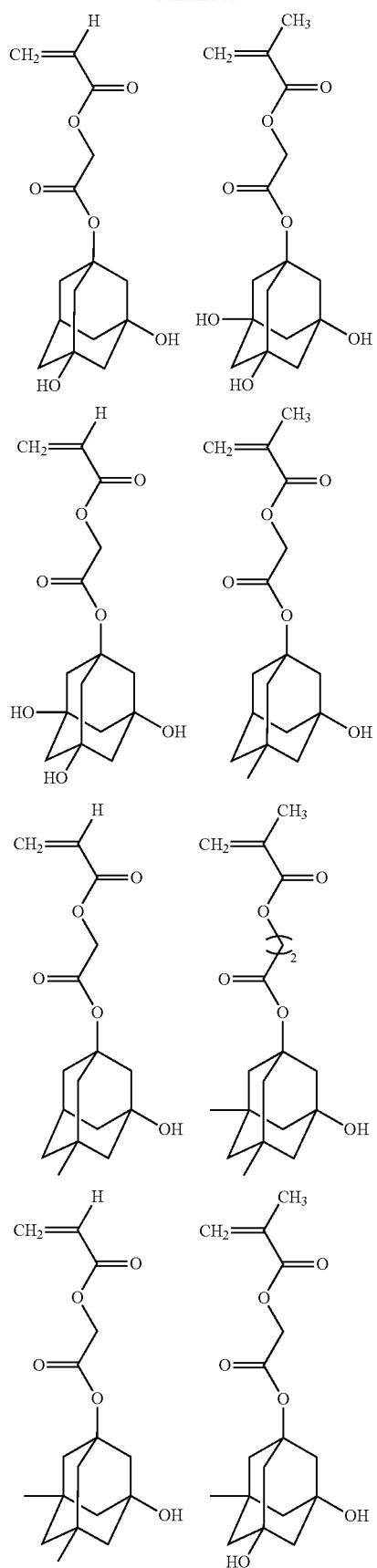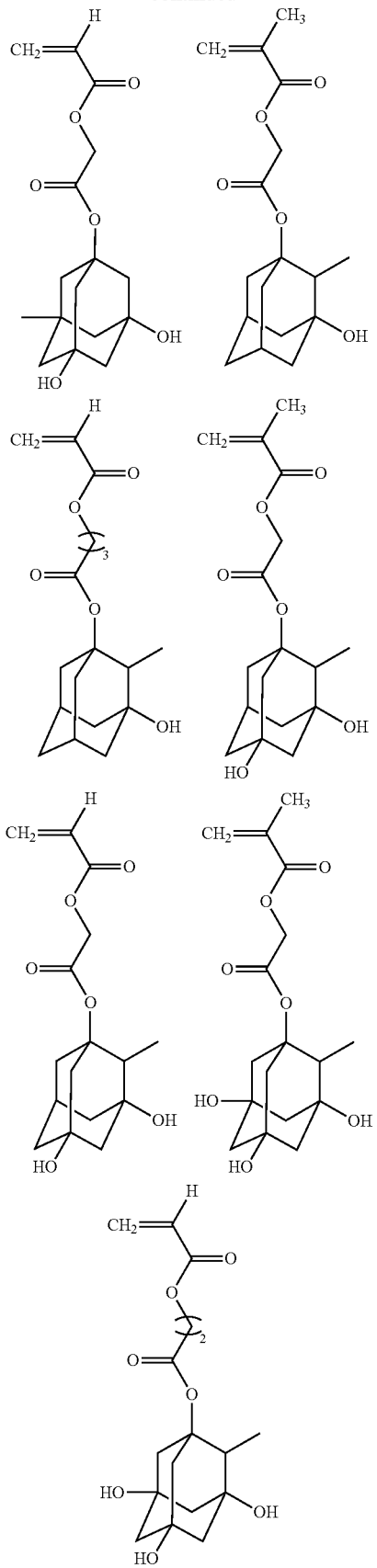

When the resin contains the structural unit derived from the monomer represented by the formula (a2-1), the content of the structural unit derived from the monomer represented by the formula (a2-1) is usually 3 to 40% by mole and preferably 5 to 35% by mole and more preferably 5 to 30% by mole based on total molar of all the structural units of the resin.

Examples of the lactone ring of the compound having no acid-labile group and having a lactone ring include a monocyclic lactone ring such as β-propiolactone ring, γ-butyrolactone ring and γ-valerolactone ring, and a condensed ring formed from a monocyclic lactone ring and the other ring. Among them, preferred are γ-butyrolactone ring and a condensed lactone ring formed from γ-butyrolactone ring and the other ring.

Preferable examples of the monomer having no acid-labile group and a lactone ring include the monomers represented by the formulae (a3-1), (a3-2) and (a3-3):

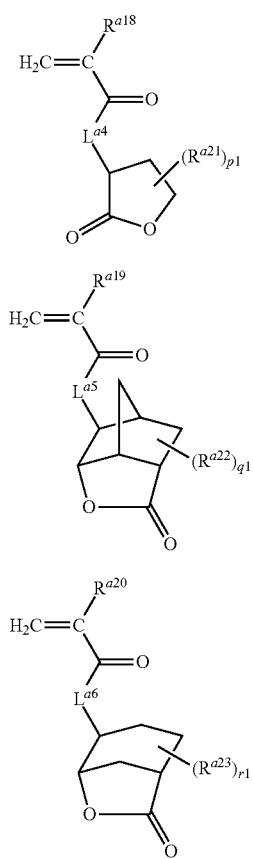

wherein $L^{a4}$, $L^{a5}$ and $L^{a6}$ each independently represent *—O— or *—O—$(CH_2)_{k3}$—CO—O— in which * represents a binding position to —CO— and k3 represents an integer of 1 to 7, $R^{a18}$, $R^{a19}$ and $R^{a20}$ each independently represent a hydrogen atom or a methyl group, $R^{a21}$ represents a C1-C4 aliphatic hydrocarbon group, $R^{a22}$ and $R^{a23}$ are independently in each occurrence a carboxyl group, a cyano group or a C1-C4 aliphatic hydrocarbon group, and p1 represents an integer of 0 to 5, q1 and r1 independently each represent an integer of 0 to 3.

It is preferred that $L^{a4}$, $L^{a5}$ and $L^{a6}$ each independently represent *—O— or *—O—$(CH_2)_{d1}$—CO—O— in which * represents a binding position to —CO— and d1 represents an integer of 1 to 4, and it is more preferred that $L^{a4}$, $L^{a5}$ and $L^{a6}$ are *—O—. $R^{a18}$, $R^{a19}$ and $R^{a20}$ are preferably methyl groups. $R^{a21}$ is preferably a methyl group. It is preferred that $R^{a22}$ and $R^{a23}$ are independently in each occurrence a carboxyl group, a cyano group or a methyl group. It is preferred that p1 is an integer of 0 to 2, and it is more preferred that p1 is 0 or 1. It is preferred that q1 and r1 independently each represent an integer of 0 to 2, and it is more preferred that q1 and r1 independently each represent 0 or 1.

Examples of the monomer represented by the formula (a3-1) include the followings.

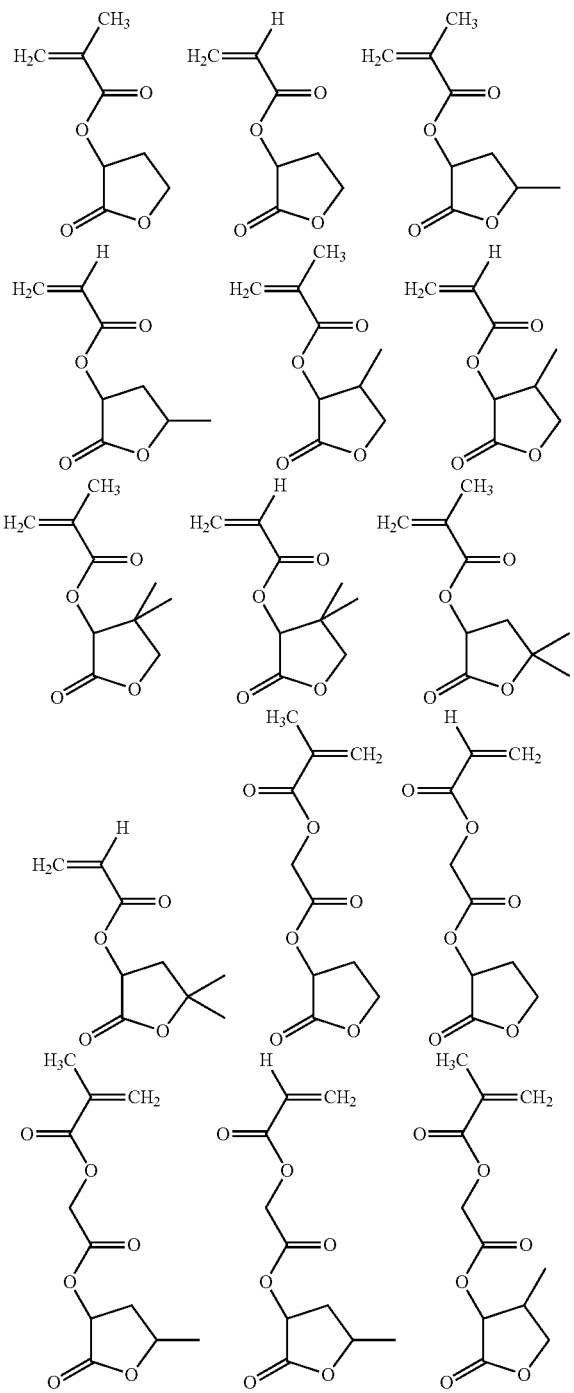

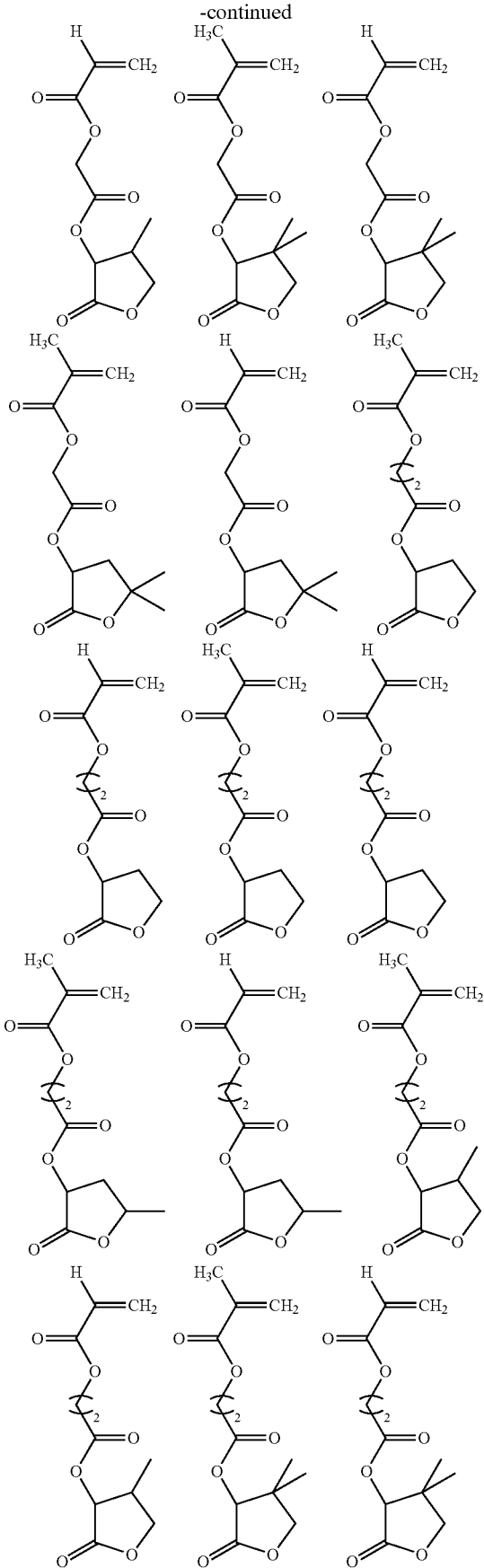
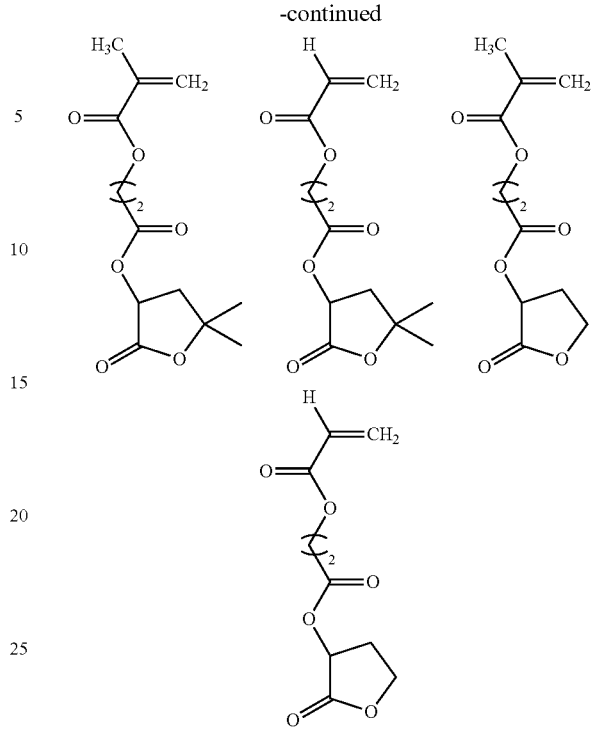
Examples of the monomer represented by the formula (a3-2) include the followings.
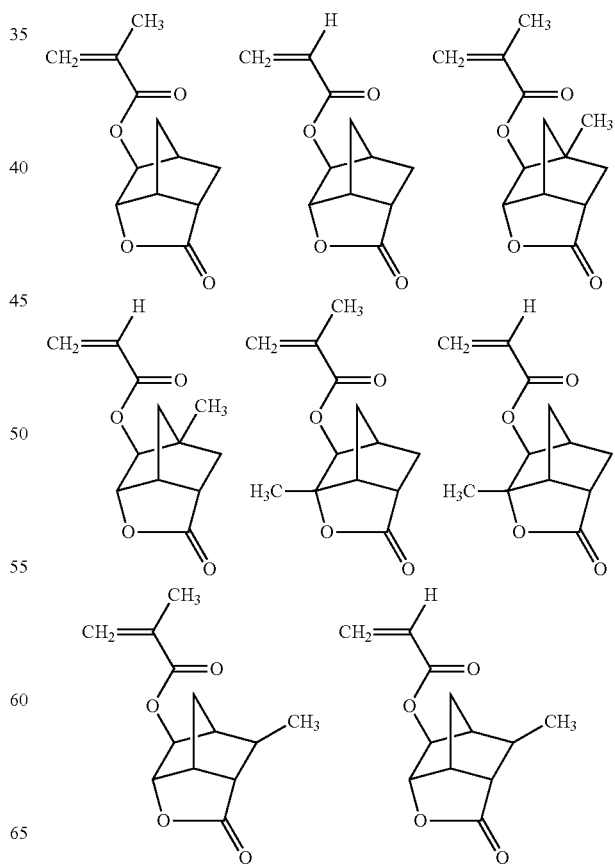

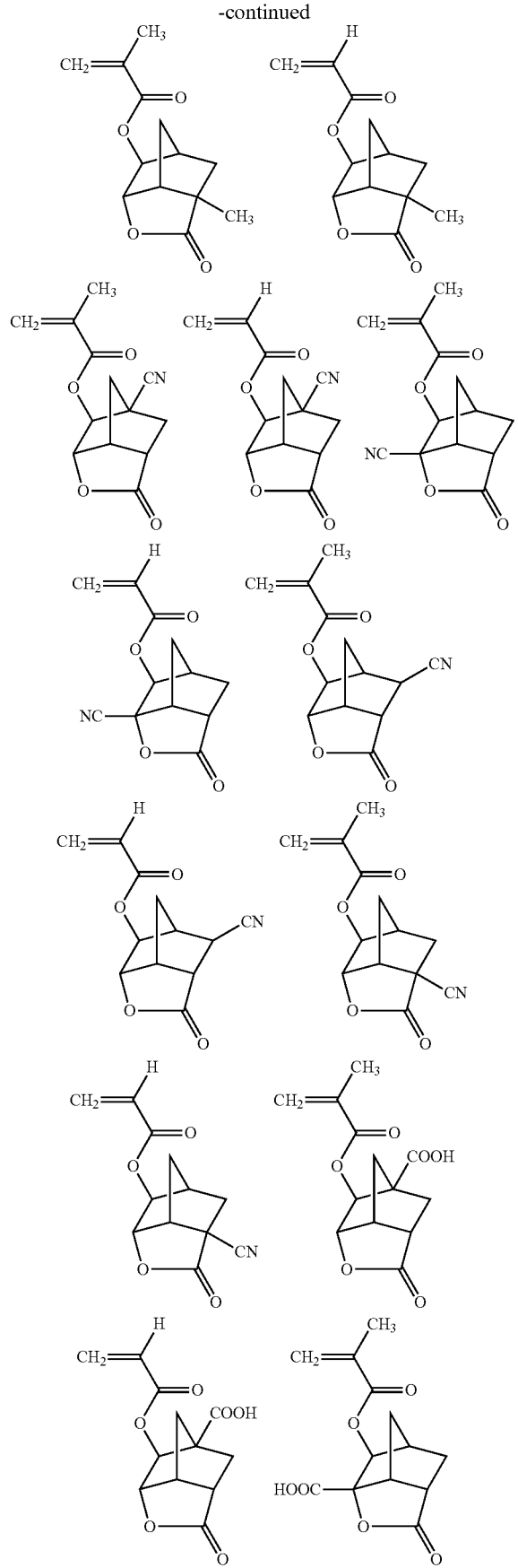
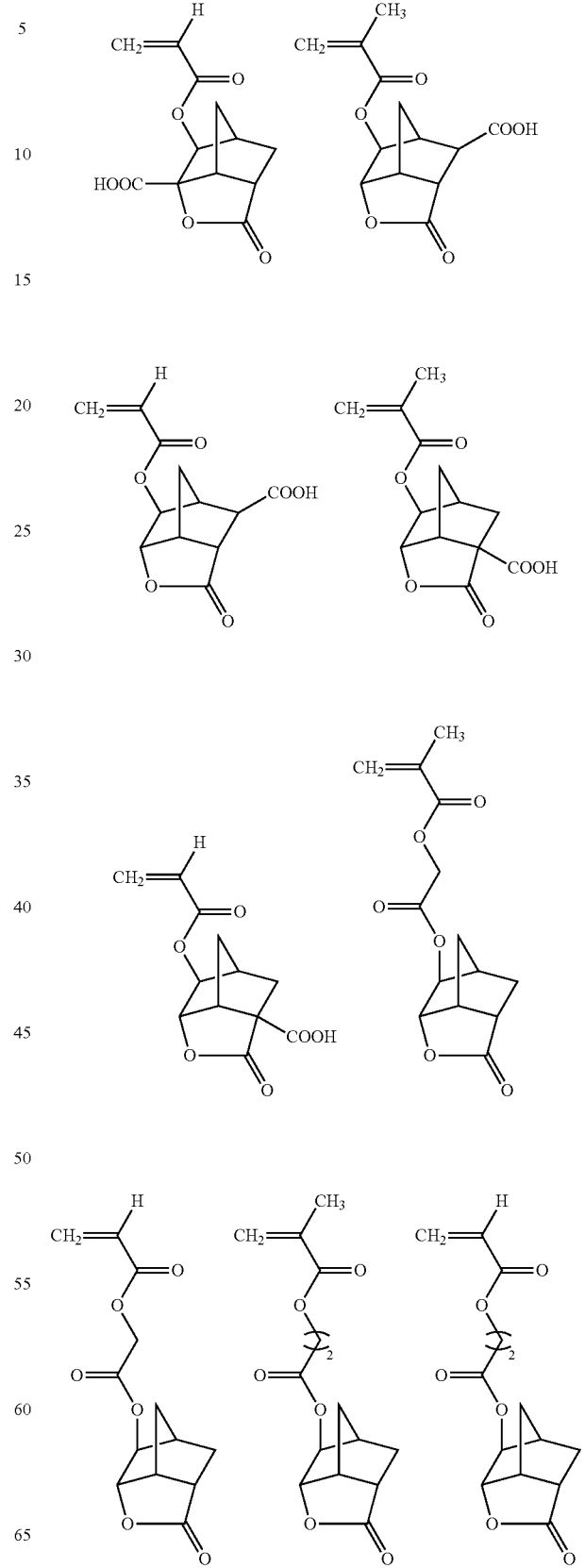

57
-continued
58
-continued
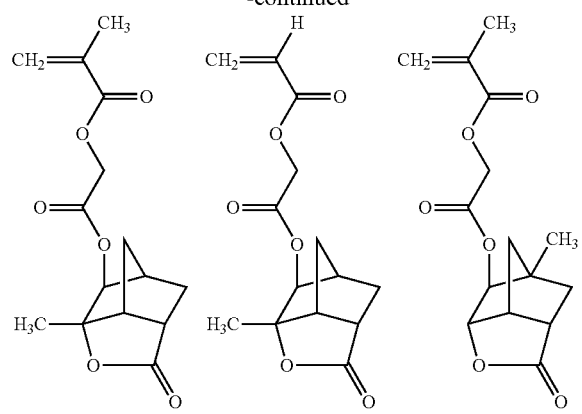
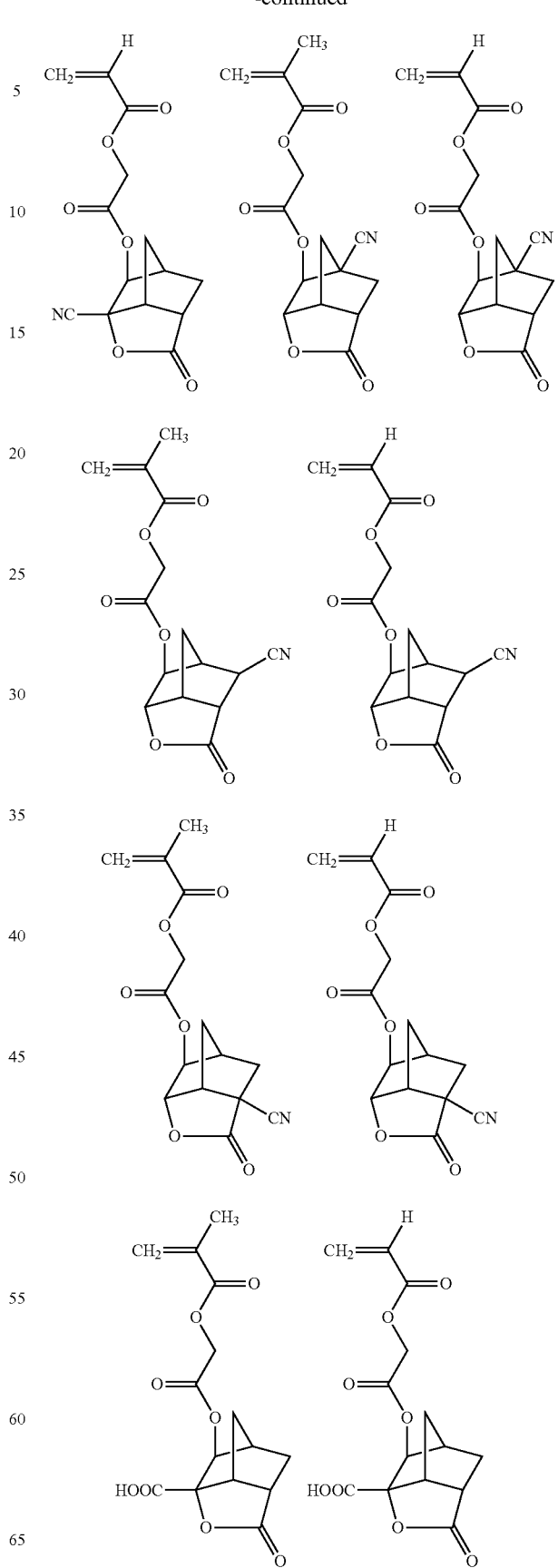

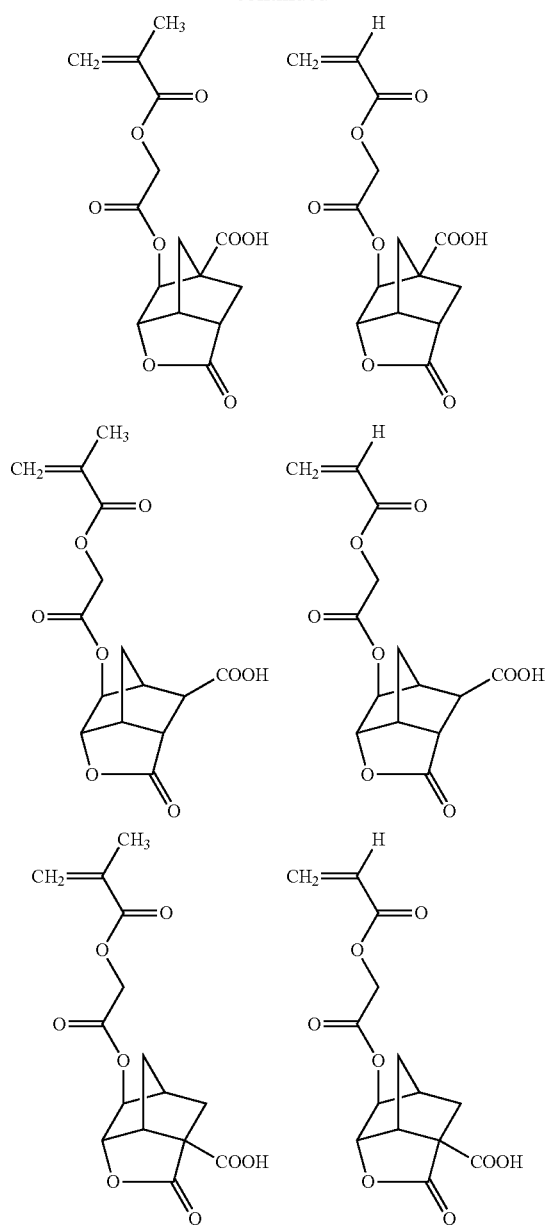
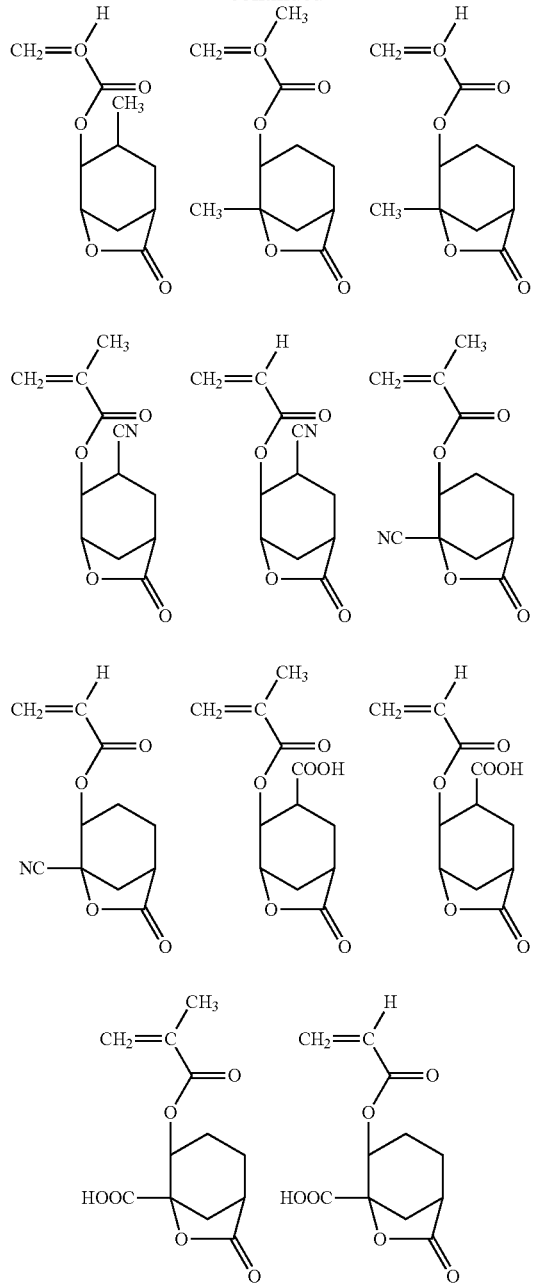
Examples of the monomer represented by the formula (a3-3) include the followings.
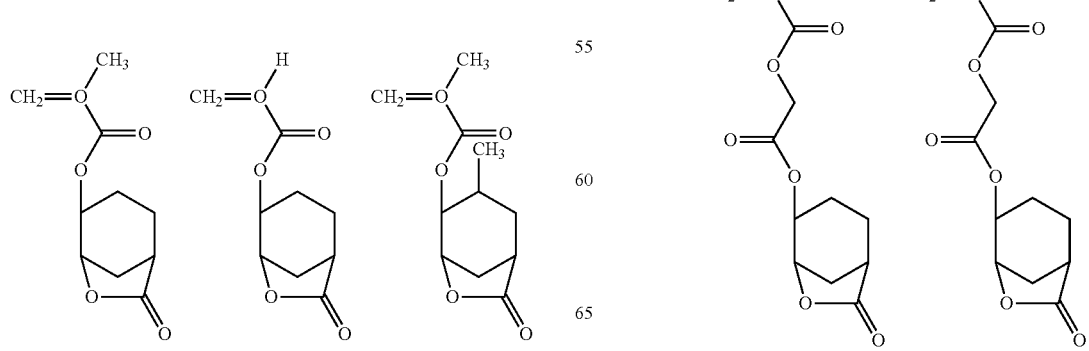

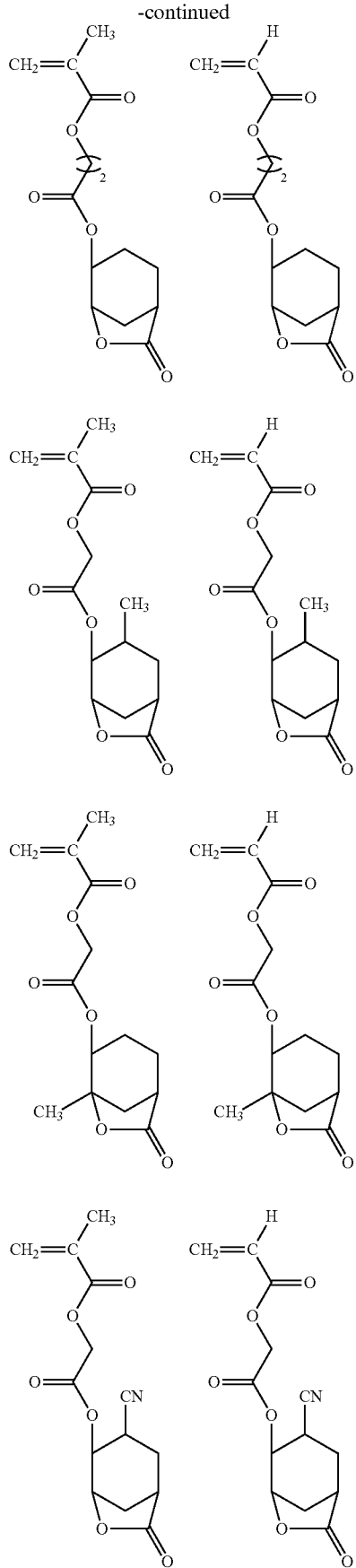
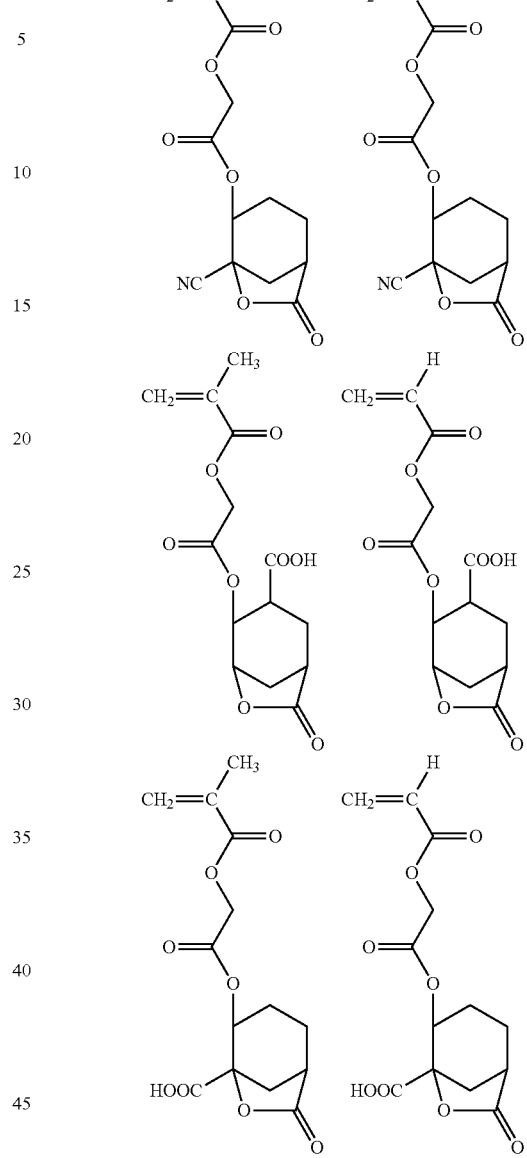

Among them, preferred are 5-oxo-4-oxatricyclo[4.2.1.0$^{3,7}$]nonan-2-yl acrylate, 5-oxo-4-oxatricyclo[4.2.1.0$^{3,7}$]nonan-2-yl methacrylate, tetrahydro-2-oxo-3-furyl acrylate, tetrahydro-2-oxo-3-furyl methacrylate, 2-(5-oxo-4-oxatricyclo[4.2.1.0$^{3,7}$]nonan-2-yloxy)-2-oxoethyl acrylate and 2-(5-oxo-4-oxatricyclo[4.2.1.0$^{3,7}$]nonan-2-yloxy)-2-oxoethyl methacrylate, and more preferred are 5-oxo-4-oxatricyclo[4.2.1.0$^{3,7}$]nonan-2-yl methacrylate, tetrahydro-2-oxo-3-furyl methacrylate and 2-(5-oxo-4-oxatricyclo[4.2.1.0$^{3,7}$]nonan-2-yloxy)-2-oxoethyl methacrylate.

When the resin contains the structural unit derived from the monomer having no acid-labile group and having a lactone ring, the content thereof is usually 5 to 50% by mole and preferably 10 to 45% by mole and more preferably 15 to 40% by mole based on total molar of all the structural units of the resin.

The resin can contain a structural unit derived from a monomer having an acid labile group containing a lactone ring. Examples of the monomer having an acid labile group containing a lactone ring include the followings.

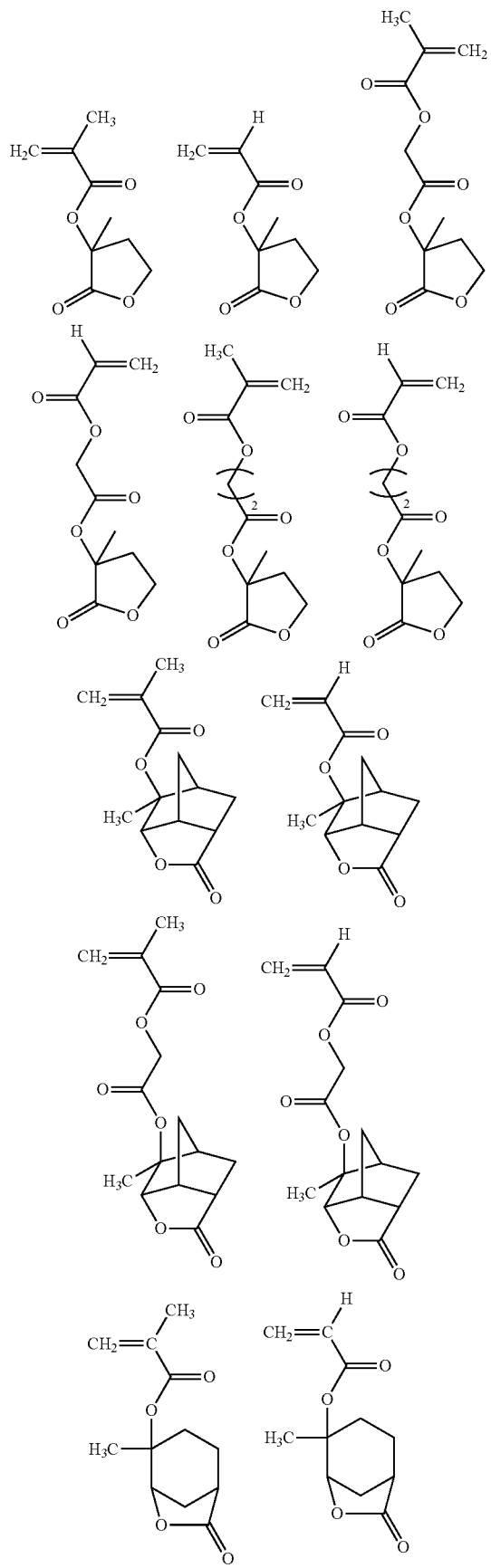

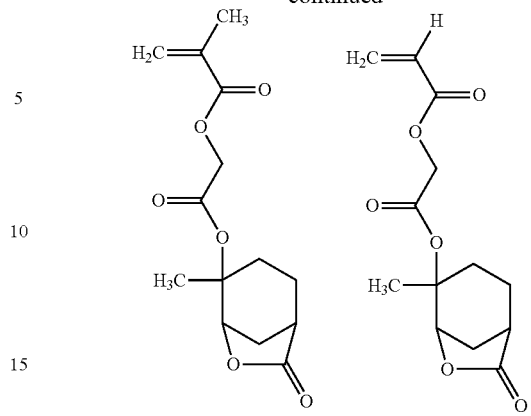

Examples of the other monomer having no acid-labile group include the monomers represented by the formulae (a-4-1), (a-4-2) and (a-4-3):

(a4-1)

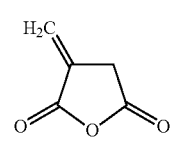
(a4-2)

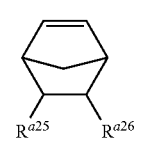
(a4-3)

wherein $R^{a25}$ and $R^{a26}$ each independently represents a hydrogen atom, a C1-C3 aliphatic hydrocarbon group which can have one or more substituents, a carboxyl group, a cyano group or a —COOR$^{a27}$ group in which $R^{a27}$ represents a C1-C36 aliphatic hydrocarbon group or a C3-C36 saturated cyclic hydrocarbon group, and one or more —CH$_2$— in the C1-C36 aliphatic hydrocarbon group and the C3-C36 saturated cyclic hydrocarbon group can be replaced by —O— or —CO—, with the proviso that the carbon atom bonded to —O— of —COO— of $R^{a27}$ is not a tertiary carbon atom, or $R^{a25}$ and $R^{a26}$ are bonded together to form a carboxylic anhydride residue represented by —C(=O)OC(=O)—.

Examples of the substituent of the C1-C3 aliphatic hydrocarbon group include a hydroxyl group. Examples of the C1-C3 aliphatic hydrocarbon group which can have one or more substituents include a C1-C3 alkyl group such as a methyl group, an ethyl group and a propyl group, and a C1-C3 hydroxyalkyl group such a hydroxymethyl group and a 2-hydroxyethyl group. The C1-C36 aliphatic hydrocarbon group represented by $R^{a27}$ is preferably a C1-C8 aliphatic hydrocarbon group and is more preferably a C1-C6 aliphatic hydrocarbon group.

The C3-C36 saturated cyclic hydrocarbon group represented by $R^{a27}$ is preferably a C4-C36 saturated cyclic hydrocarbon group, and is more preferably C4-C12 saturated cyclic hydrocarbon group. Examples of $R^{a27}$ include a methyl group, an ethyl group, a propyl group, a 2-oxo-oxolan-3-yl group and a 2-oxo-oxolan-4-yl group.

Examples of the monomer represented by the formula (a-4-3) include 2-norbornene, 2-hydroxy-5-norbornene, 5-norbornene-2-carboxylic acid, methyl 5-norbornene-2-carboxylate, 2-hydroxyethyl 5-norbornene-2-carboxylate, 5-norbornene-2-methanol and 5-norbornene-2,3-dicarboxylic anhydride.

When the resin contains a structural unit derived from a monomer represented by the formula (a-4-1), (a-4-2) or (a-4-3), the content thereof is usually 2 to 40% by mole and preferably 3 to 30% by mole and more preferably 5 to 20% by mole based on total molar of all the structural units of the resin.

Preferable resin is a resin containing the structural units derived from the monomer having an acid-labile group, and the structural units derived from the monomer having one or more hydroxyl groups and/or the monomer having a lactone ring. The monomer having an acid-labile group is preferably the monomer represented by the formula (a1-1) or the monomer represented by the formula (a1-2), and is more preferably the monomer represented by the formula (a1-1).

The monomer having one or more hydroxyl groups is preferably the monomer represented by the formula (a2-1), and the monomer having a lactone ring is preferably the monomer represented by the formula (a3-1) or (a3-2).

The resin can be produced according to known polymerization methods such as radical polymerization.

The resin usually has 2,500 or more of the weight-average molecular weight, and preferably 3,000 or more of the weight-average molecular weight. The resin usually has 50,000 or less of the weight-average molecular weight, and preferably has 30,000 or less of the weight-average molecular weight. The weight-average molecular weight can be measured with gel permeation chromatography.

The first photoresist composition of the present invention usually includes 80% by weight or more of the solid component.

The photoresist composition of the present invention contains an acid generator, and preferably a photoacid generator.

The acid generator is a substance which is decomposed to generate an acid by applying a radiation such as a light, an electron beam or the like on the substance itself or on a photoresist composition containing the substance. The acid generated from the acid generator acts on the resin resulting in cleavage of the acid-labile group existing in the resin.

Examples of the acid generator include a nonionic acid generator, an ionic acid generator and the combination thereof.

An ionic acid generator is preferable. Examples of the nonionic acid generator include an organo-halogen compound, a sulfone compound such as a disulfone, a ketosulfone and a sulfonyldiazomethane, a sulfonate compound such as a 2-nitrobenzylsulfonate, an aromatic sulfonate, an oxime sulfonate, an N-sulfonyloxyimide, a sulfonyloxyketone and DNQ 4-sulfonate. Examples of the ionic acid generator include an acid generator having an inorganic anion such as $BF_4^-$, $PF_6^-$, $AsF_6^-$ and $SbF_6^-$, and an acid generator having an organic anion such as a sulfonic acid anion and a bissulfonylimido anion, and an acid generator having a sulfonic acid anion is preferable.

Preferable examples of the acid generator include a salt represented by the formula (B1):

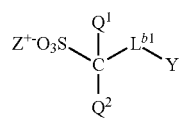

(B1)

wherein $Q^1$ and $Q^2$ each independently represent a fluorine atom or a C1-C6 perfluoroalkyl group, $L^{b1}$ represents a single bond or a C1-C17 divalent saturated hydrocarbon group in which one or more methylene groups can be replaced by —O— or —CO—, Y represents a C1-C18 aliphatic hydrocarbon group which can have one or more substituents, or a C3-C18 saturated cyclic hydrocarbon group which can have one or more substituents, and one or more methylene groups in the aliphatic hydrocarbon group and the saturated cyclic hydrocarbon group can be replaced by —O—, —CO— or —SO$_2$—, and $Z^+$ represents an organic cation.

Examples of the C1-C6 perfluoroalkyl group include a trifluoromethyl group, a pentafluoroethyl group, a heptafluoropropyl group, a nonafluorobutyl group, an undecafluoropentyl group and a tridecafluorohexyl group, and a trifluoromethyl group is preferable. $Q^1$ and $Q^2$ each independently preferably represent a fluorine atom or a trifluoromethyl group, and $Q^1$ and $Q^2$ are more preferably fluorine atoms.

Examples of the C1-C17 divalent saturated hydrocarbon group include a C1-C17 linear alkylene group such as a methylene group, an ethylene group, a propane-1,3-diyl group, a propane-1,2-diyl group, a butane-1,4-diyl group, a butane-1,3-diyl group, a pentane-1,5-diyl group, a hexane-1,6-diyl group, a heptane-1,7-diyl group, an octane-1,8-diyl group, a nonane-1,9-diyl group, a decane-1,10-diyl group, a undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group and a heptadecane-1,17-diyl group, a C1-C17 branched alkylene group such as a 1-methyl-1,3-propylene group, a 2-methyl-1,3-propylene group, a 2-methyl-1,2-propylene group, a 1-methyl-1,4-butylene group, and a 2-methyl-1,4-butylene group, a divalent saturated monocyclic hydrocarbon group such as a cycloalkylene group such as a 1,3-cyclobutylene group, a 1,3-cyclopentylene group, a 1,4-cyclohexylene group, and a 1,5-cyclooctylene group, and a divalent saturated polycyclic hydrocarbon group such as a 1,4-norbornylene group, a 2,5-norbornylene group, a 1,5-adamantylene group and a 2,6-adamantylene group.

Examples of the C1-C17 saturated hydrocarbon group in which one or more methylene groups are replaced by —O— or —CO— include *—CO—O-$L^{b2}$-, *—CO—O-$L^{b4}$-CO—O-$L^{b3}$-, *$L^{b5}$-O—CO—, *-$L^{b7}$-O-$L^{b6}$-, *—CO—O-$L^{b8}$-O—, and *—CO—O-$L^{b10}$-O-$L^{b9}$-CO—O—, wherein $L^{b2}$ represents a single bond or a C1-C15 alkanediyl group, $L^{b3}$ represents a single bond or a C1-C12 alkanediyl group, $L^{b4}$ represents a single bond or a C1-C13 alkanediyl group, with proviso that total carbon number of $L^{b3}$ and $L^{b4}$ is 1 to 13, $L^{b5}$ represents a C1-C15 alkanediyl group, $L^{b6}$ represents a C1-C15 alkanediyl group, $L^{b7}$ represents a C1-C15 alkanediyl group, with proviso that total carbon number of $L^{b6}$ and $L^{b7}$ is 1 to 16, $L^{b8}$ represents a C1-C14 alkanediyl group, $L^{b9}$ represents a C1-C11 alkanediyl group, $L^{b10}$ represents a C1-C11 alkanediyl group, with proviso that total carbon number of $L^{b9}$ and $L^{b10}$ is 1 to 12, and * represents a binding position to —C($Q^1$)($Q^2$)-. Among them, preferred are *—CO—O-$L^{b2}$-, *—CO—O-$L^{b4}$-CO—O-$L^{b3}$-, *-$L^{b5}$-O—CO— and *-$L^{b7}$-O-$L^{b6}$-, and more preferred are *—CO—O-$L^{b2}$- and *—CO—O-$L^{b4}$-CO—O-$L^{b3}$-, and much more preferred is *—CO—O-$L^{b2}$-, and especially preferred is *—CO—O-$L^{b2}$- in which $L^{b2}$ is a single bond or —CH$_2$—.

Examples of *—CO—O-$L^{b2}$- include *—CO—O— and *—CO—O—CH$_2$—. Examples of *—CO—O-$L^{b4}$-CO—O-$L^{b3}$- include *—CO—O—CH$_2$—CO—O—, *—CO—O—(CH$_2$)$_2$—CO—O—, *—CO—O— (CH$_2$)$_3$—CO—O—, *—CO—O—(CH$_2$)$_4$—CO—O—, *—CO—O—(CH$_2$)$_6$—CO—O—, *—CO—O—(CH$_2$)$_8$—CO—O—, *—CO—O—CH$_2$—CH(CH$_3$)—CO—O— and *—CO—O—CH$_2$—C(CH$_3$)$_2$—CO—O—. Examples of *-$L^{b5}$-O—CO— include *—CH$_2$—O—CO—, *—(CH$_2$)$_2$—O—CO—, *—(CH$_2$)$_3$—

O—CO—, *—(CH$_2$)$_4$—O—CO—, *—(CH$_2$)$_6$—O—CO— and *—(CH$_2$)$_8$—O—CO—. Examples of *-L$^{b7}$-O-L$^{b6}$- include *—CH$_2$—O—CH$_2$—. Examples of *—CO—O-L$^{b8}$-O— include *—CO—O—CH$_2$—O—, *—CO—O—(CH$_2$)$_2$—O—, *—CO—O—(CH$_2$)$_3$—O—, *—CO—O—(CH$_2$)$_4$—O— and *—CO—O—(CH$_2$)$_6$—O—. Examples of *—CO—O-L$^{b10}$-O-L$^{b9}$-CO—O— include the followings.

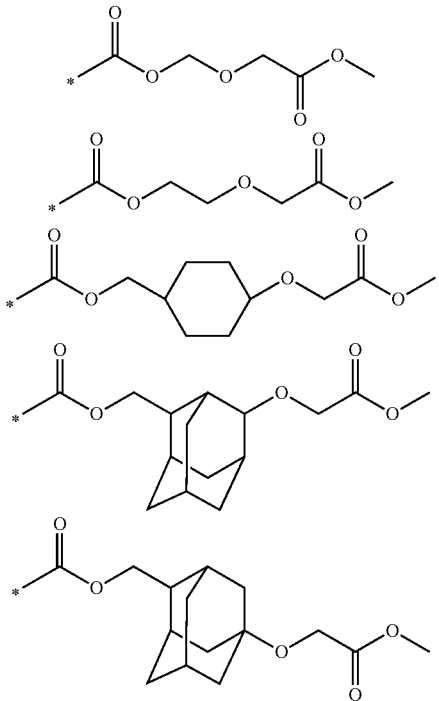

The saturated hydrocarbon group can have one or more substituents, and examples of the substituent include a halogen atom, a hydroxyl group, a carboxyl group, a C6-C18 aromatic hydrocarbon group, a C7-C21 aralkyl group such as a benzyl group, a phenethyl group, a phenylpropyl group, a trityl group, a naphthylmethyl group and a naphthyethyl group, a C2-C4 acyl group and a glycidyloxy group.

Examples of the substituent in Y include a halogen atom, a hydroxyl group, an oxo group, a glycidyloxy group, a C2-C4 acyl group, a C1-C12 alkoxy group, a C2-C7 alkoxycarbonyl group, a C1-C12 aliphatic hydrocarbon group, a C1-C12 hydroxy-containing aliphatic hydrocarbon group, a C3-C16 saturated cyclic hydrocarbon group, a C6-C18 aromatic hydrocarbon group, a C7-C21 aralkyl group and —(CH$_2$)$_{j2}$—O—CO—R$^{b1}$ in which R$^{b1}$ represents a C1-C16 aliphatic hydrocarbon group, a C3-C16 saturated cyclic hydrocarbon group or a C6-C18 aromatic hydrocarbon group and j2 represents an integer of 0 to 4. Examples of the halogen atom include a fluorine atom, a chlorine atom, a bromine atom and an iodine atom. Examples of the acyl group include an acetyl group and a propionyl group, and examples of the alkoxy group include a methoxy group, an ethoxy group, a propoxy group, an isopropoxy group and a butoxy group.

Examples of the alkoxycarbonyl group include a methoxycarbonyl group, an ethoxycarbonyl group, a propoxycarbonyl group, an isopropoxycarbonyl group and a butoxycarbonyl group. Examples of the aliphatic hydrocarbon group include the same as described above.

Examples of the hydroxyl-containing aliphatic hydrocarbon group include a hydroxymethyl group. Examples of the C3-C16 saturated cyclic hydrocarbon group include the same as described above, and examples of the aromatic hydrocarbon group include a phenyl group, a naphthyl group, an anthryl group, a p-methylphenyl group, a p-tert-butylphenyl group and a p-adamantylphenyl group. Examples of the aralkyl group include a benzyl group, a phenethyl group, a phenylpropyl group, a trityl group, a naphthylmethyl group and a naphthylethyl group.

Examples of the C1-C18 aliphatic hydrocarbon group represented by Y include a methyl group, an ethyl group, a propyl group, an isopropyl group, a butyl group, an isobutyl group, a sec-butyl group, a tert-butyl group, a pentyl group, a neopentyl group, a 1-methylbutyl group, a 2-methylbutyl group, a 1,2-dimethylpropyl group, a 1-ethylpropyl group, a hexyl group, a 1-methylpentyl group, a heptyl group, an octyl group, a 2-ethylhexyl group, a nonyl group, a decyl group, an undecyl group and a dodecyl group, and a C1-C6 alkyl group is preferable. Examples of the C3-C18 saturated cyclic hydrocarbon group represented by Y include the groups represented by the formulae (Y1) to (Y26):

 (Y1)

 (Y2)

 (Y3)

 (Y4)

 (Y5)

 (Y6)

 (Y7)

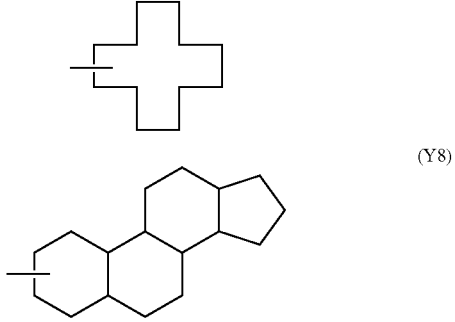 (Y8)

 (Y9)

(Y10) 
(Y11) 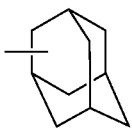
(Y12) 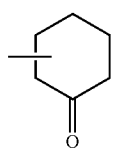
(Y13) 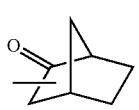
(Y14) 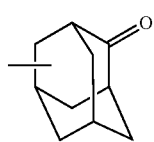
(Y15) 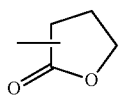
(Y16) 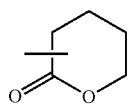
(Y17) 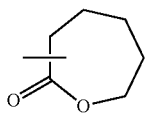
(Y18) 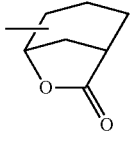
(Y19) 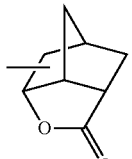
(Y20) 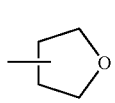
(Y21) 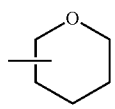
(Y22) 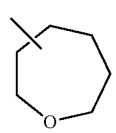
(Y23) 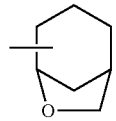
(Y24) 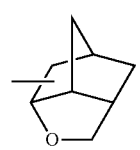
(Y25) 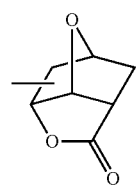
(Y26) 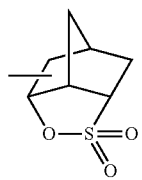
Among them, preferred are the groups represented by the formulae (Y1) to (Y19), and more preferred are the groups represented by the formulae (Y11), (Y14), (Y15) and (Y19). The groups represented by the formulae (Y11) and (Y14) are especially preferable.
Examples of Y having one or more substituents include the followings:
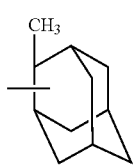 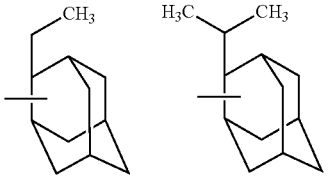
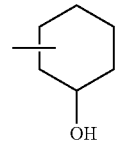 
 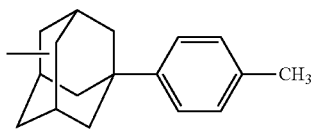

-continued

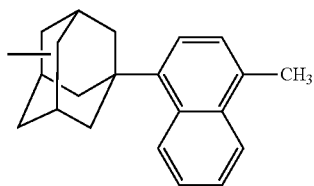

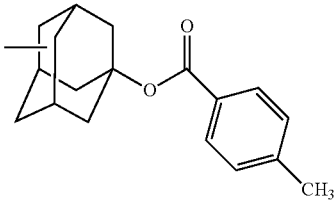

Y is preferably an adamantyl group which can have one or more substituents, and is more preferably an adamantyl group or an oxoadamantyl group.

Among the sulfonic acid anions of the acid generator represented by the formula (B1), preferred is a sulfonic acid anion having the group represented by the above-mentioned formula (b1-1), and more preferred are anions represented by the formulae (b1-1-1) to (b1-1-9).

(b1-1-1)
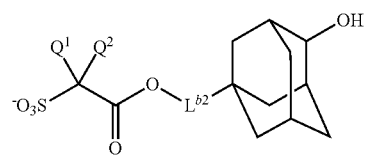

(b1-1-2)
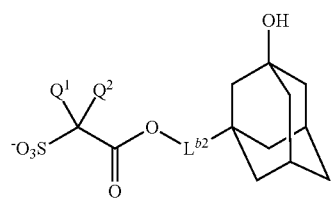

(b1-1-3)
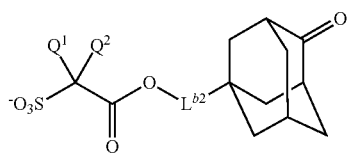

(b1-1-4)
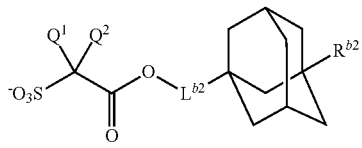

(b1-1-5)

-continued (b1-1-6)
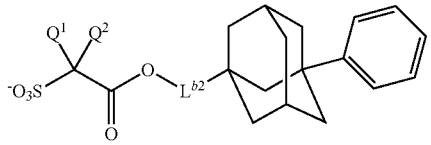

(b1-1-7)
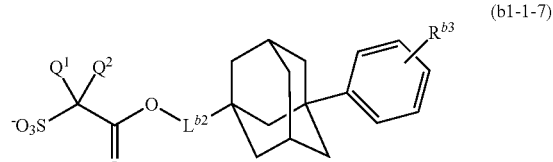

(b1-1-8)
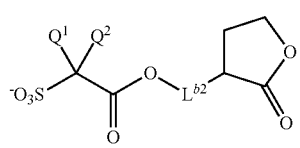

(b1-1-9)
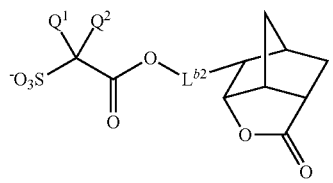

wherein $Q^1$, $Q^2$ and $L^{b2}$ are the same as defined above, and $R^{b2}$ and $R^{b3}$ each independently represent a C1-C4 aliphatic hydrocarbon group, preferably a methyl group.

Specific examples of the sulfonic acid anion include the followings.

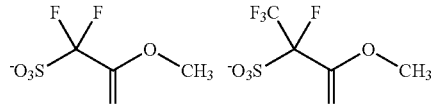
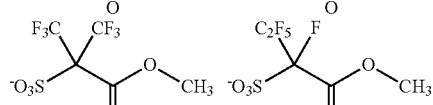
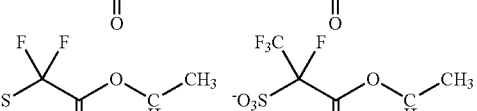
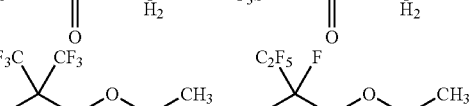
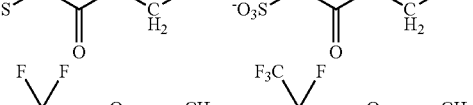
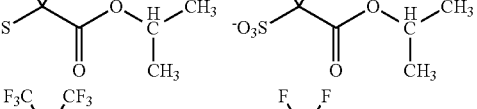

73
-continued
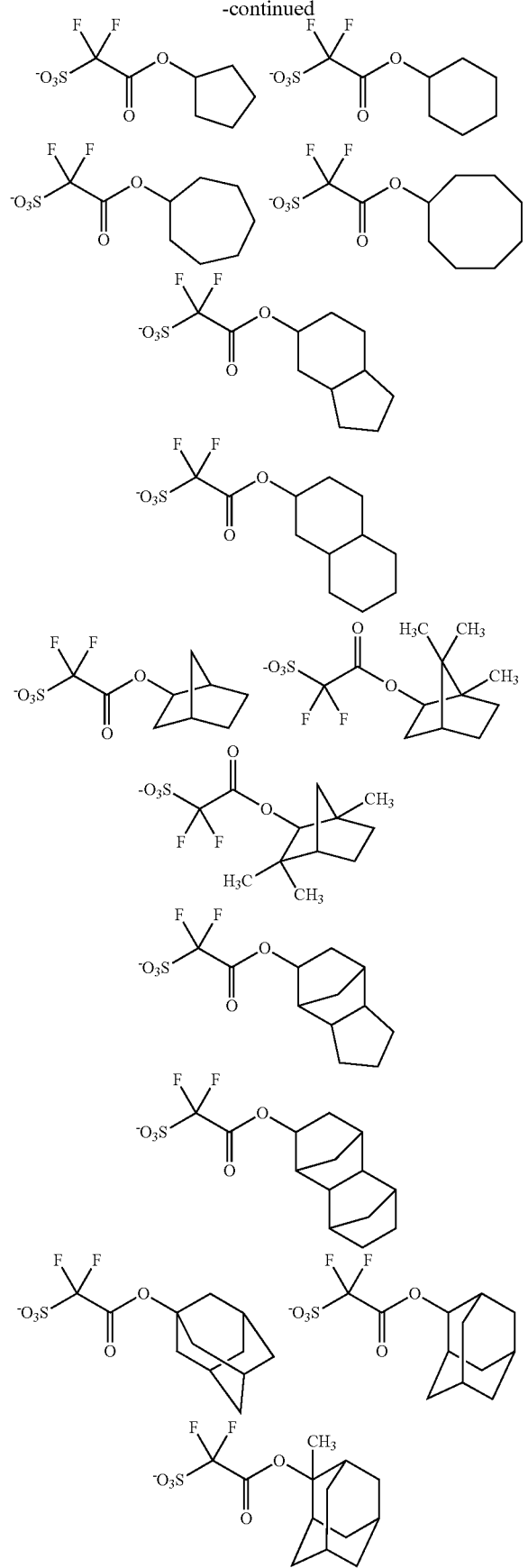
74
-continued
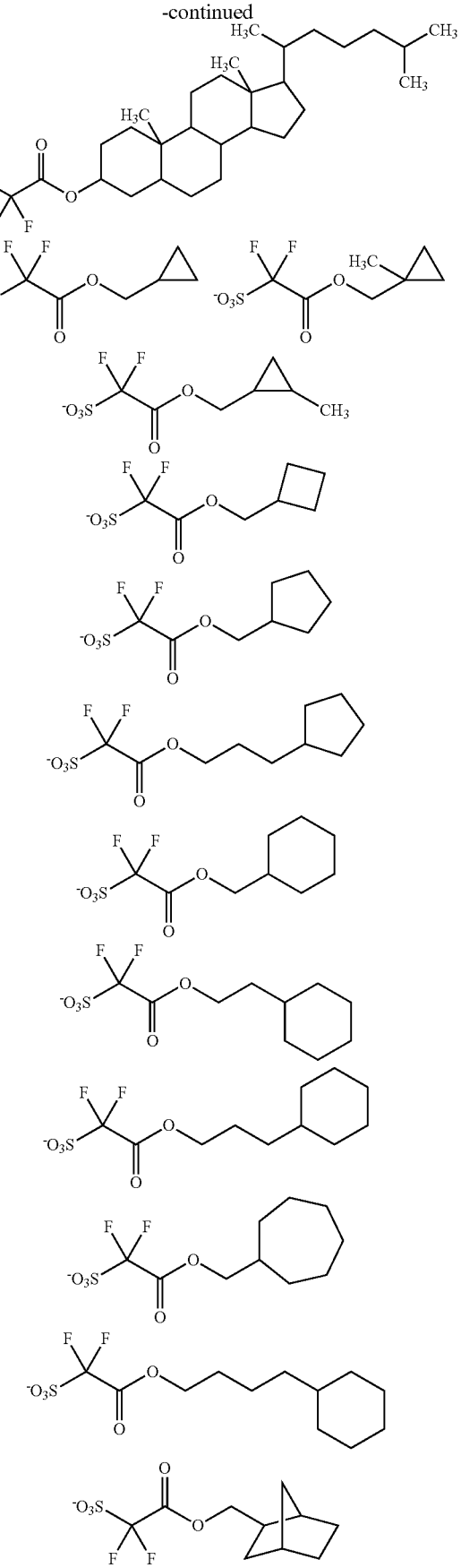

75
-continued
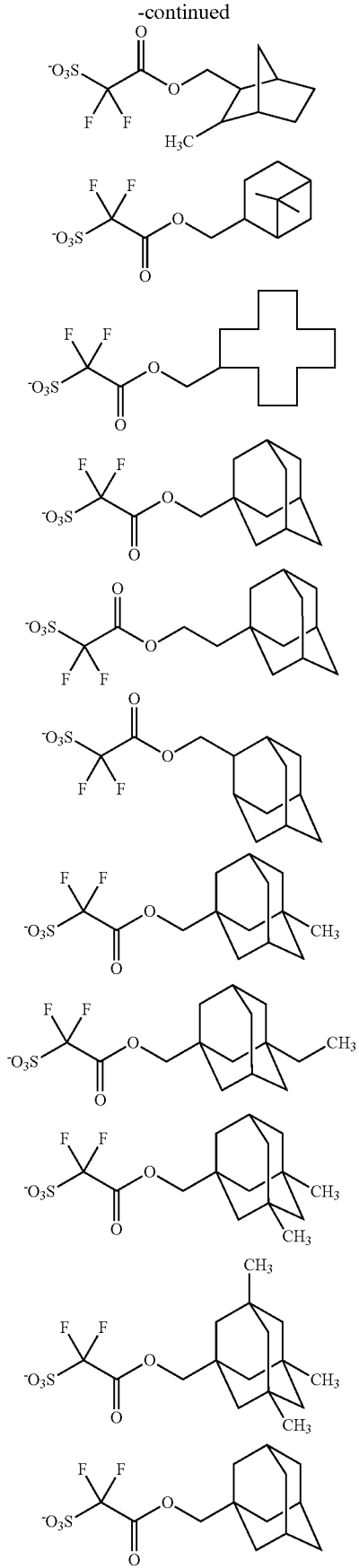
76
-continued
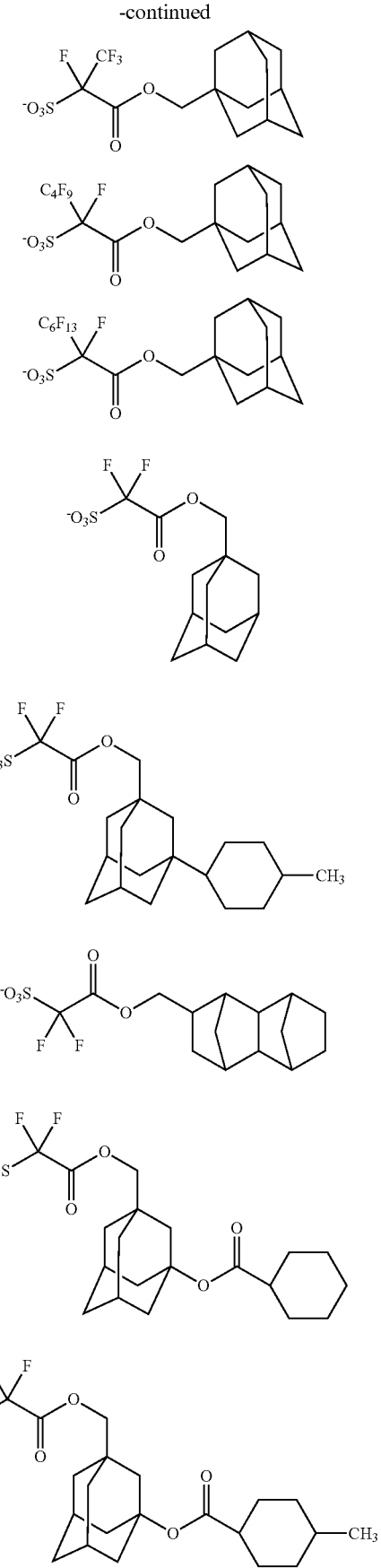

77
-continued
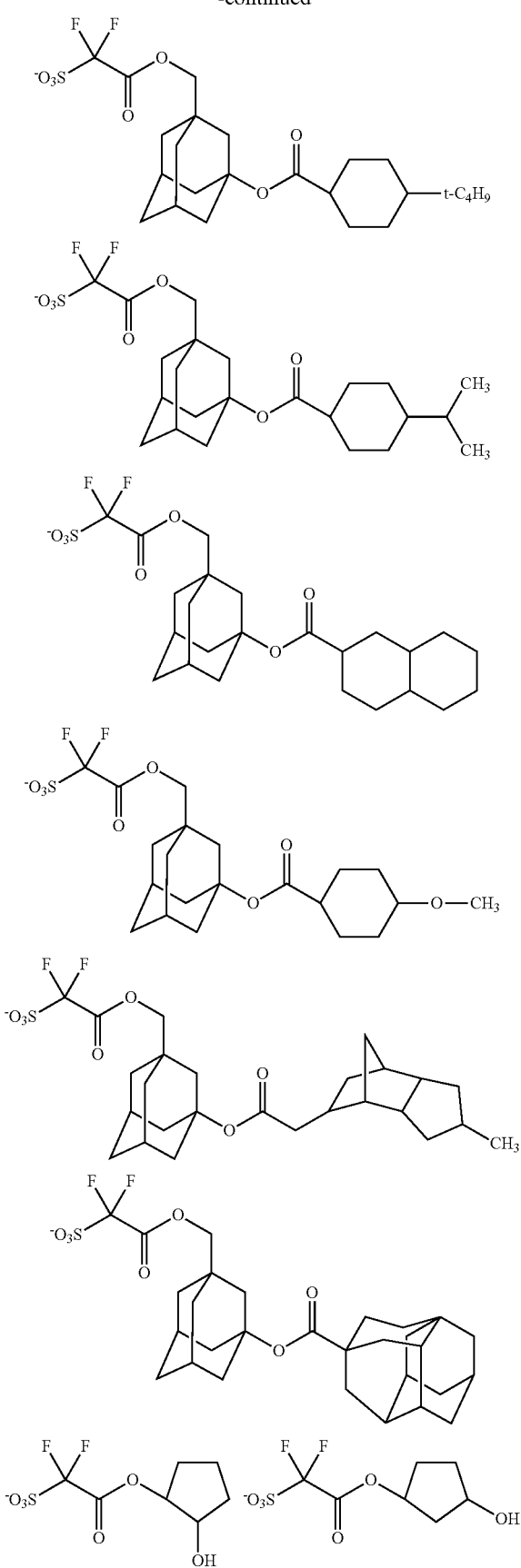
78
-continued
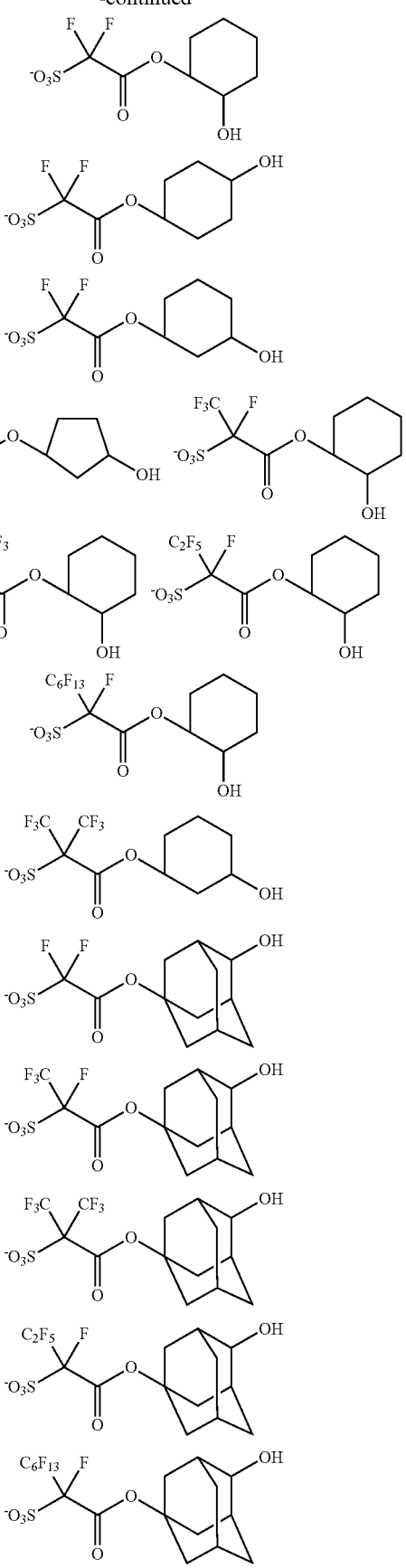

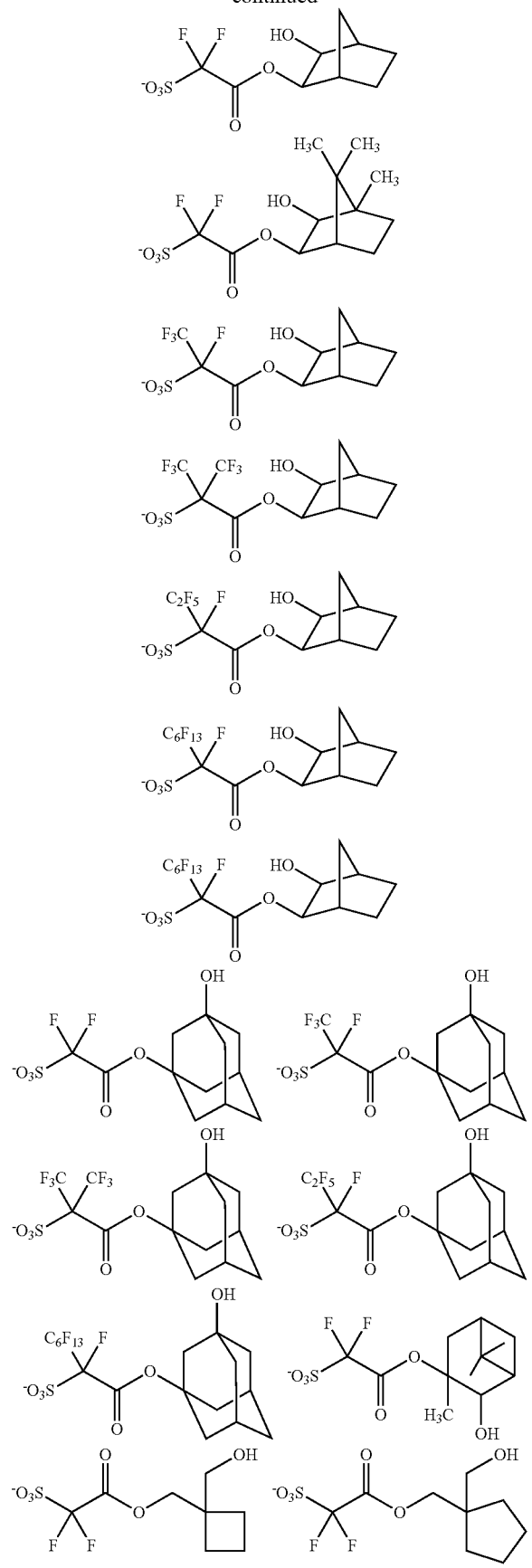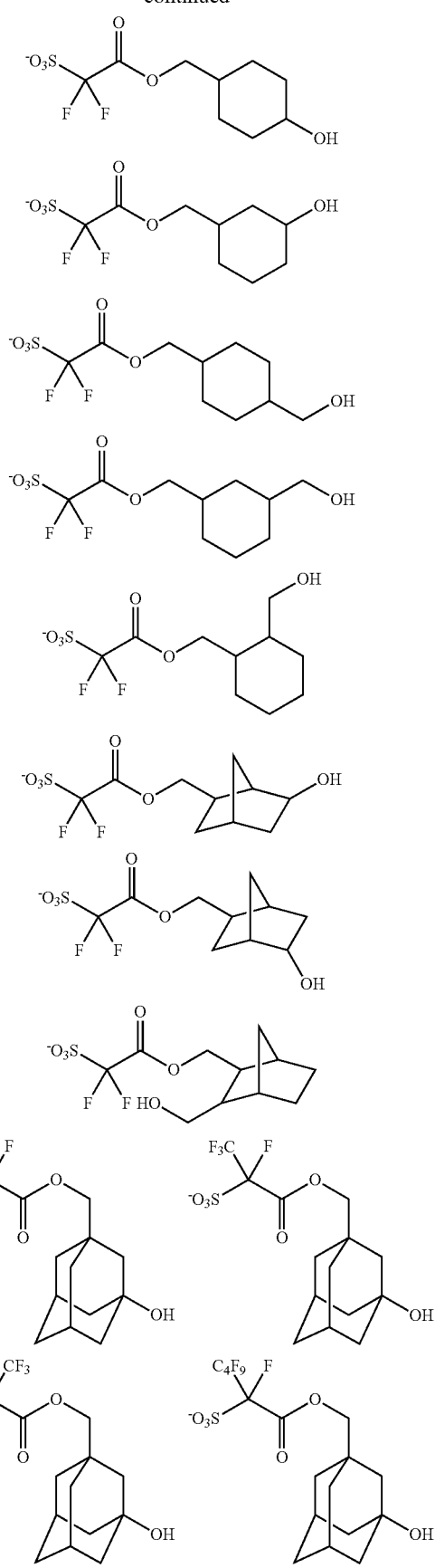

81
-continued
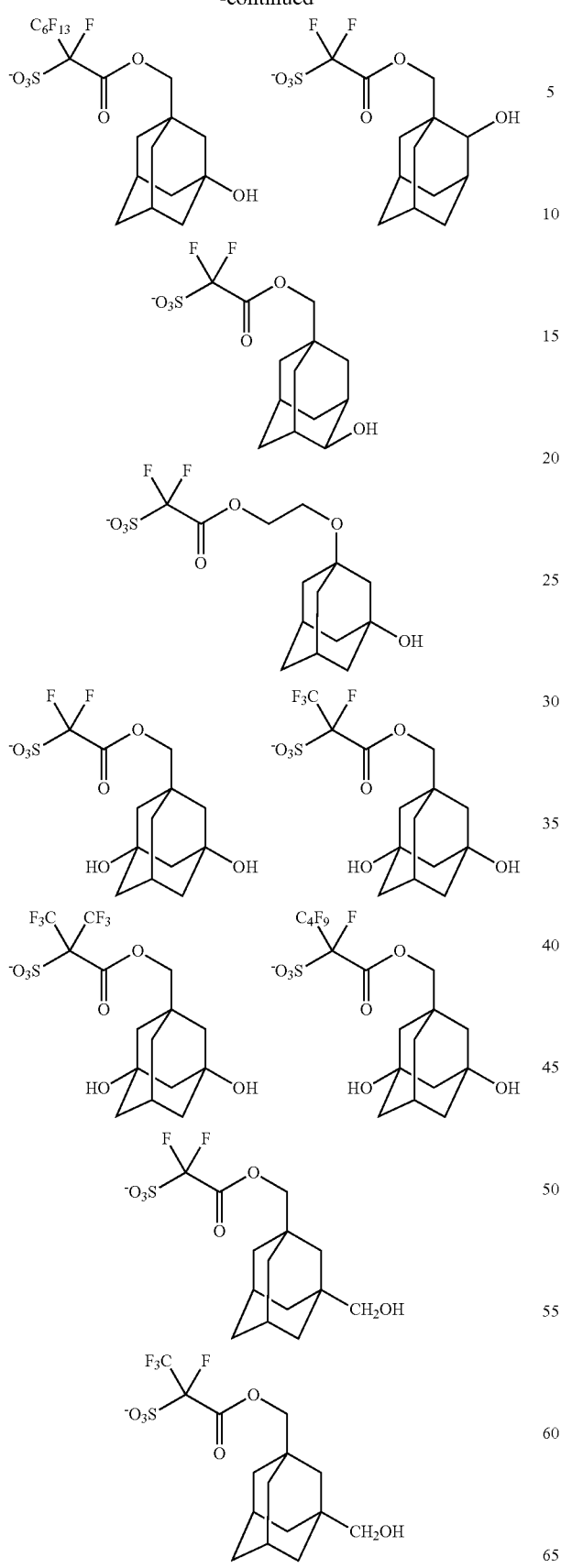
82
-continued
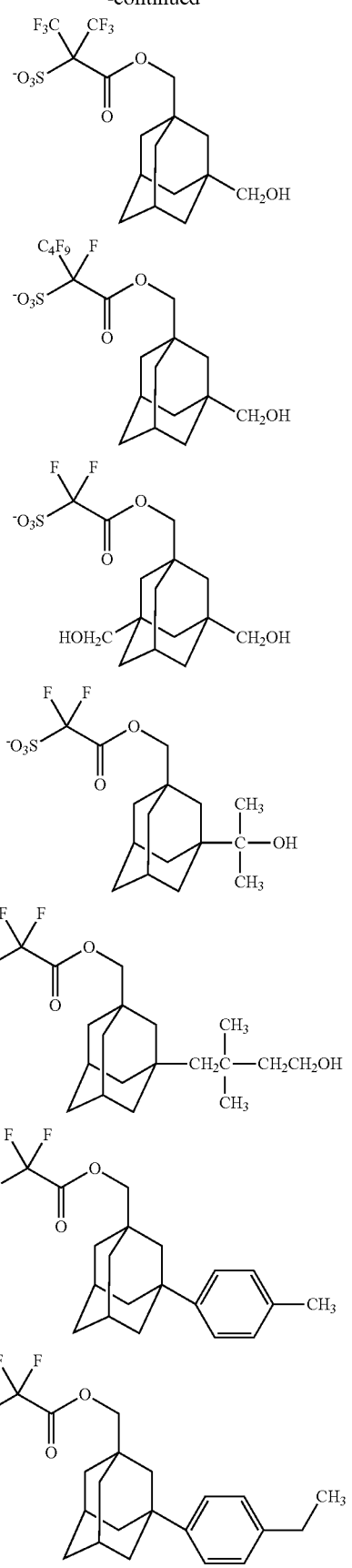

83
-continued
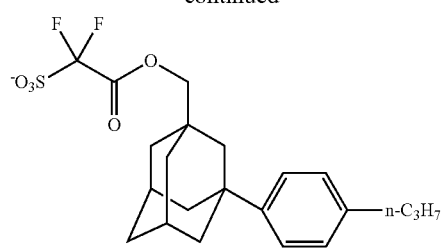
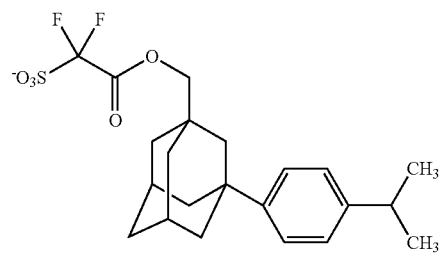
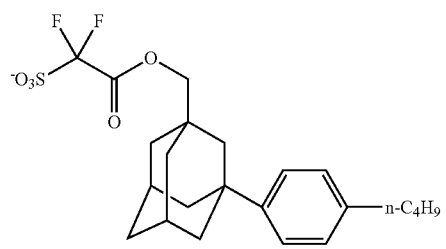
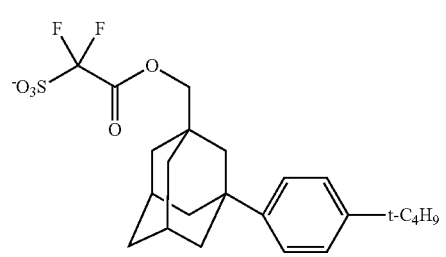
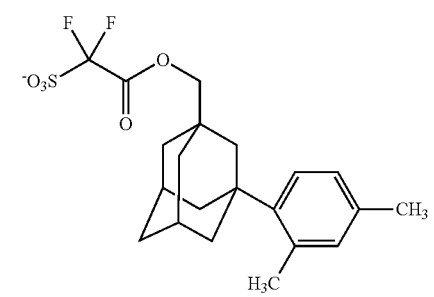
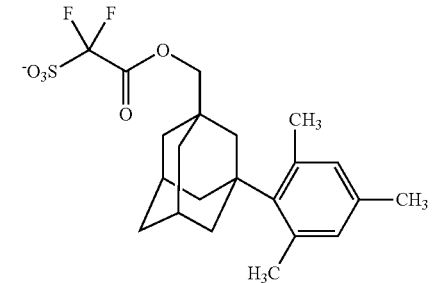
84
-continued
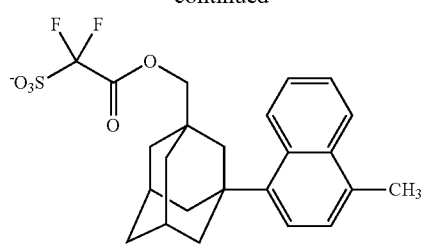
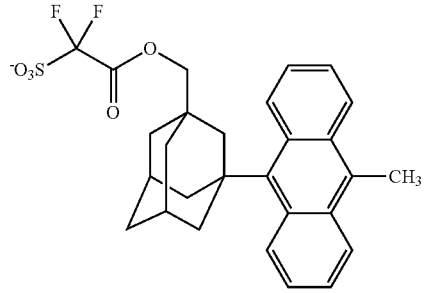
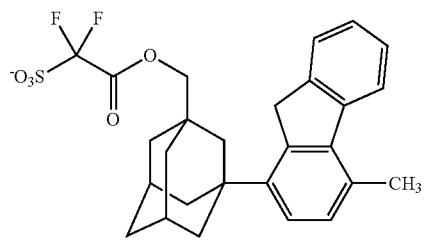
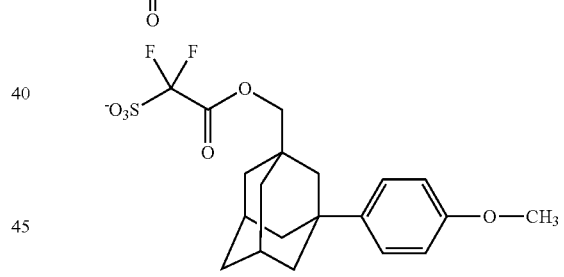
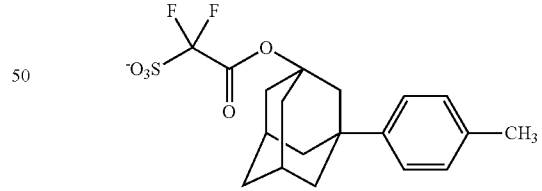
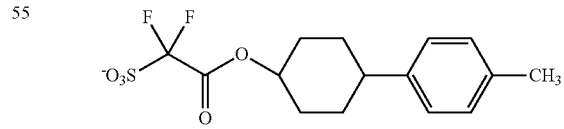
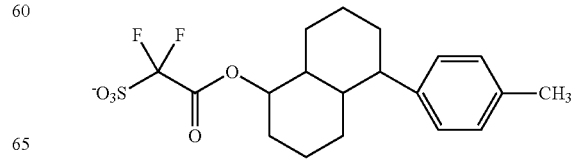

-continued
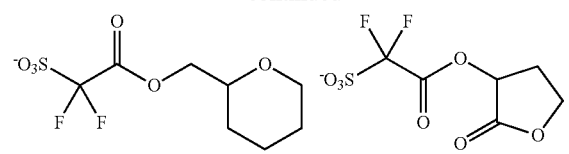
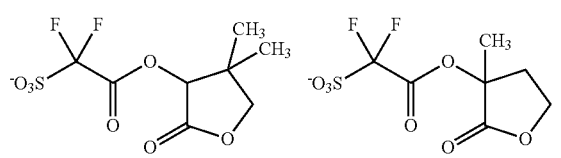
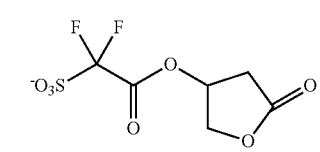
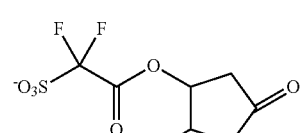
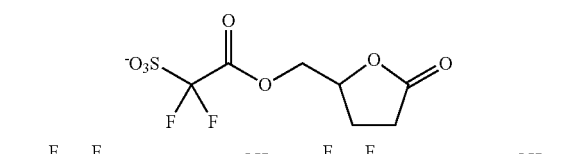
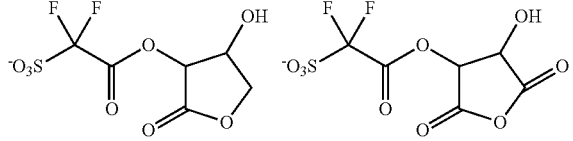
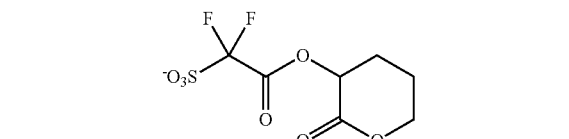
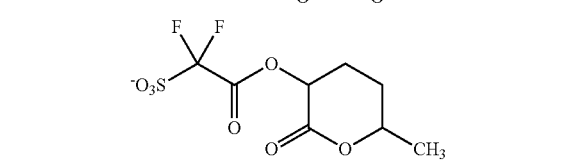
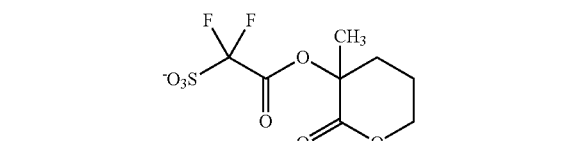
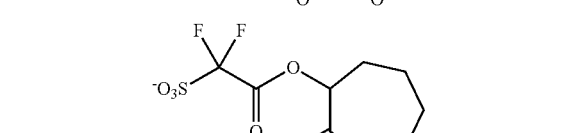
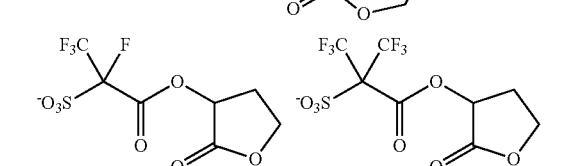
-continued
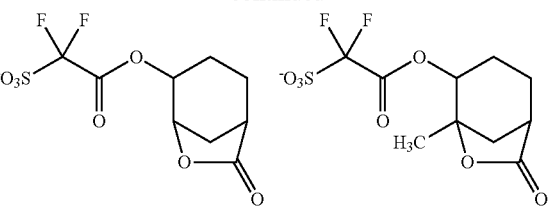
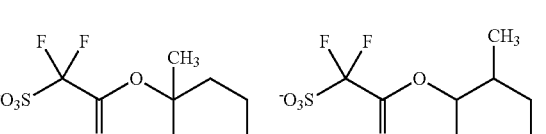
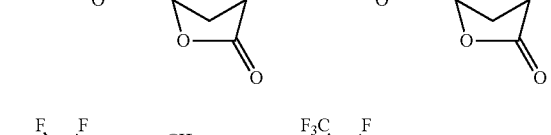
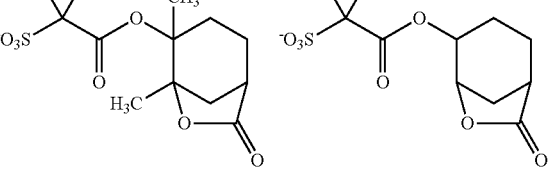
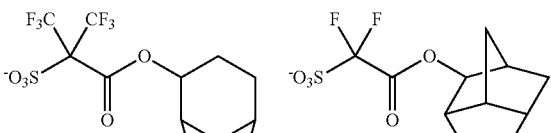
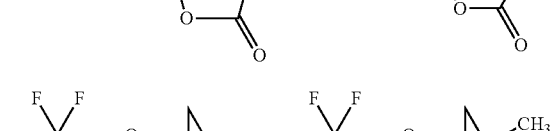
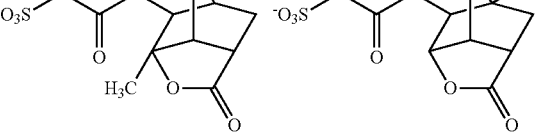
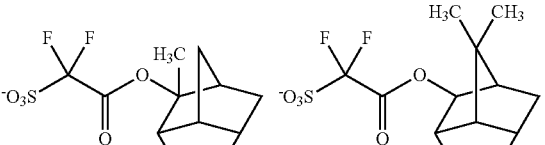
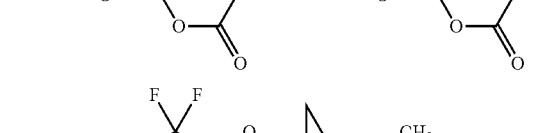
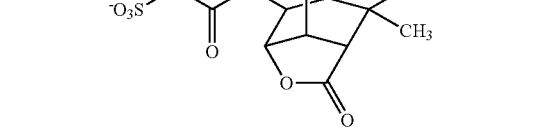
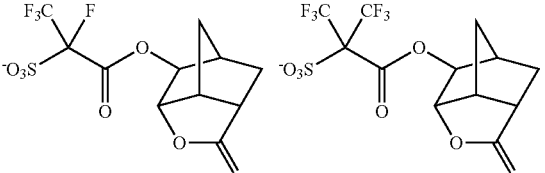

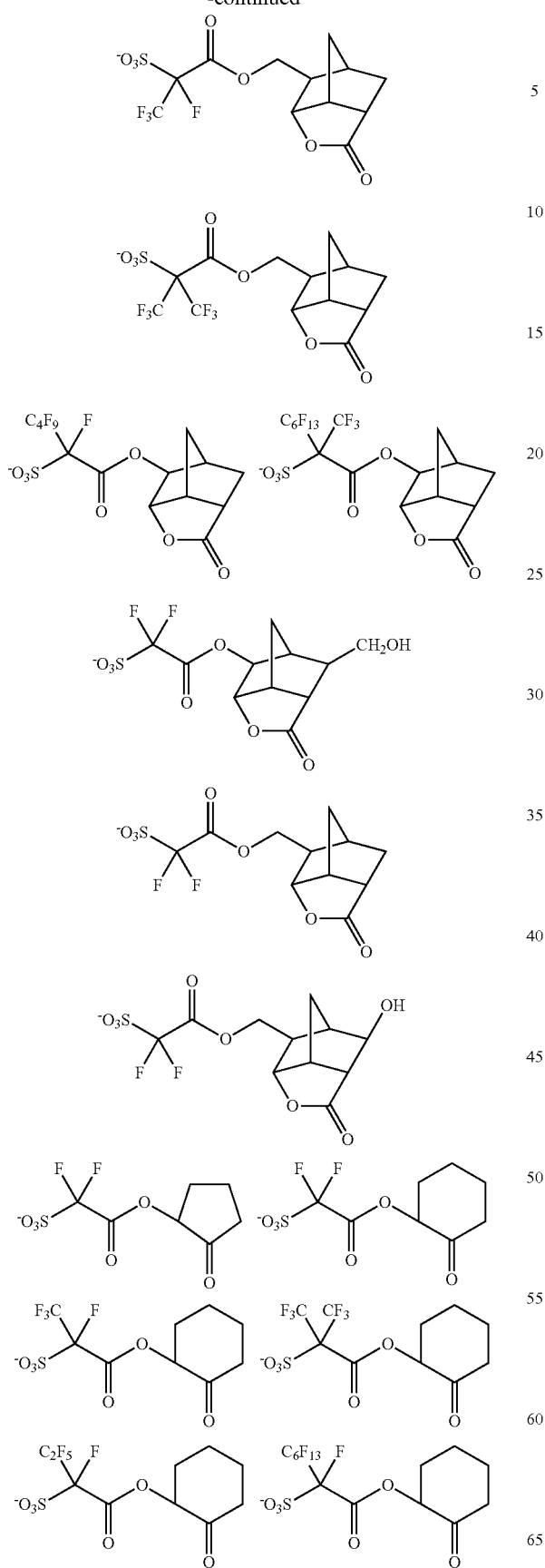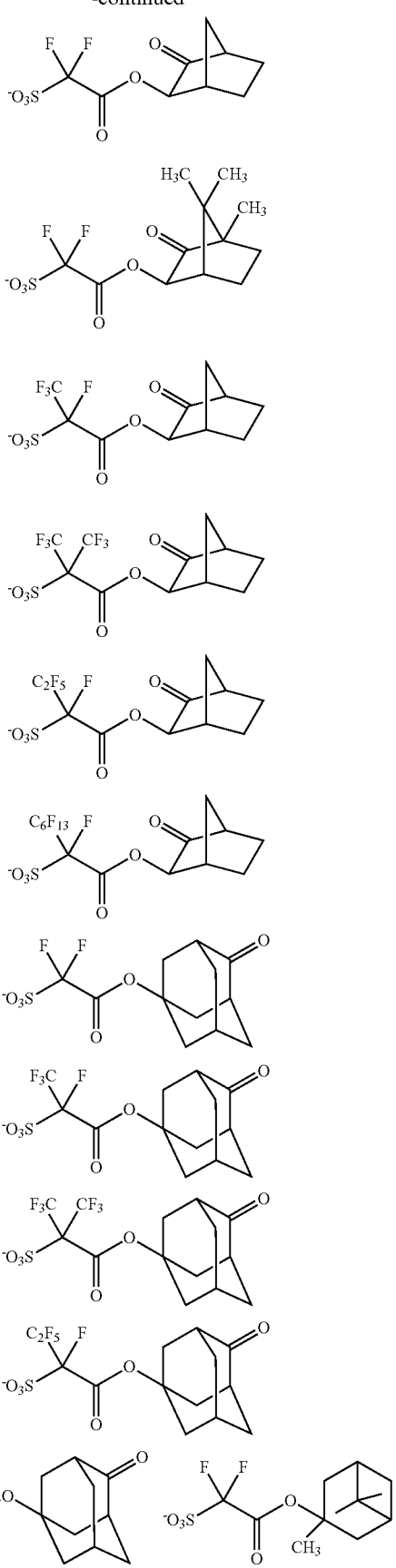

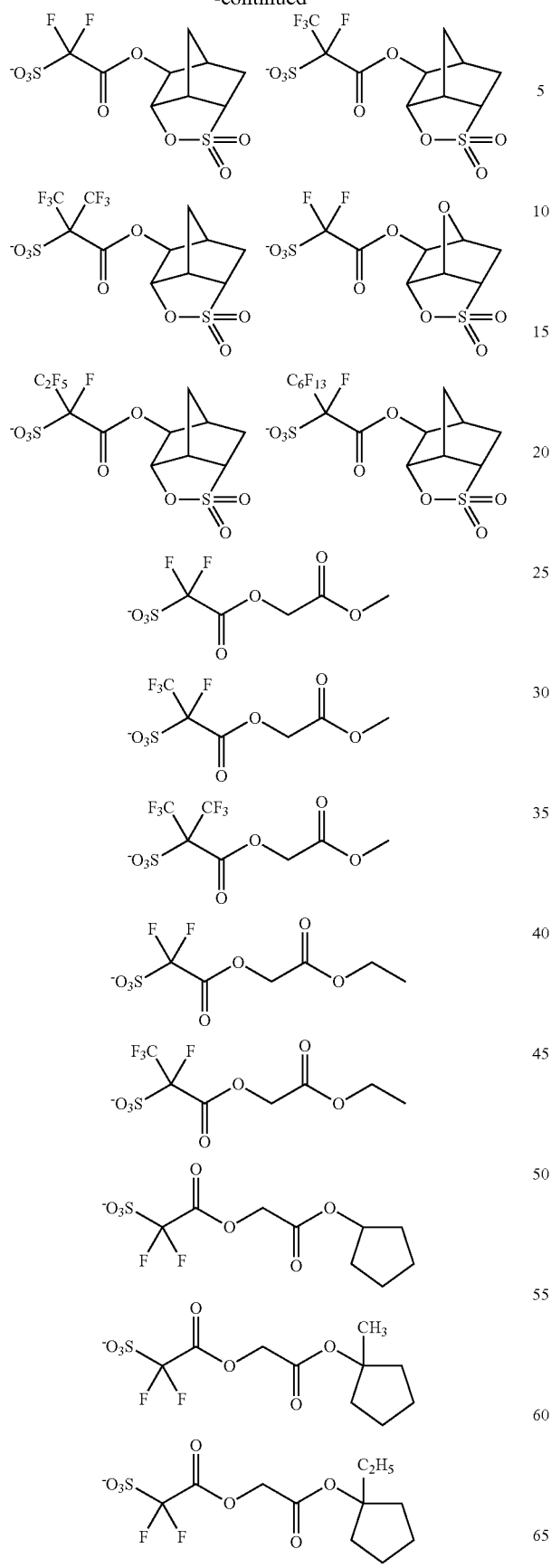
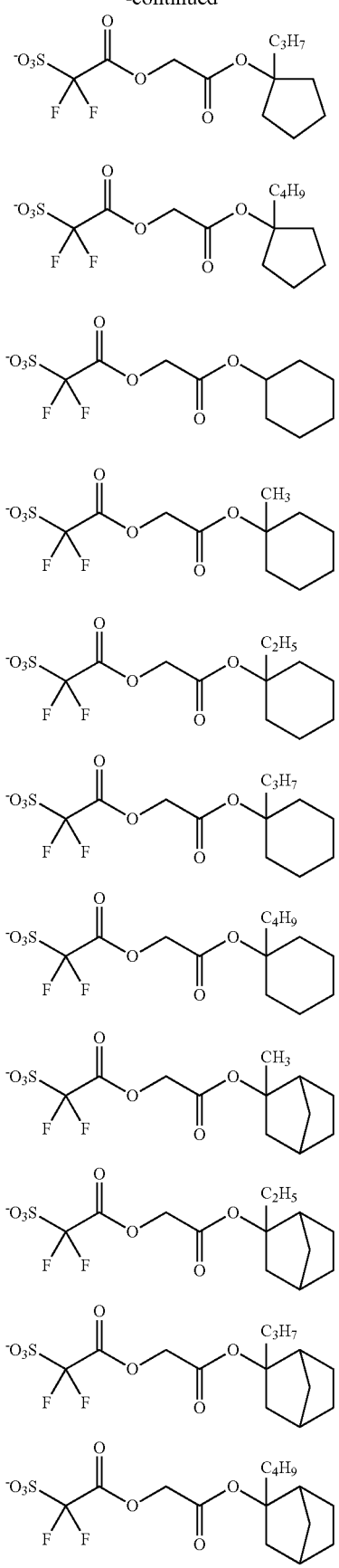

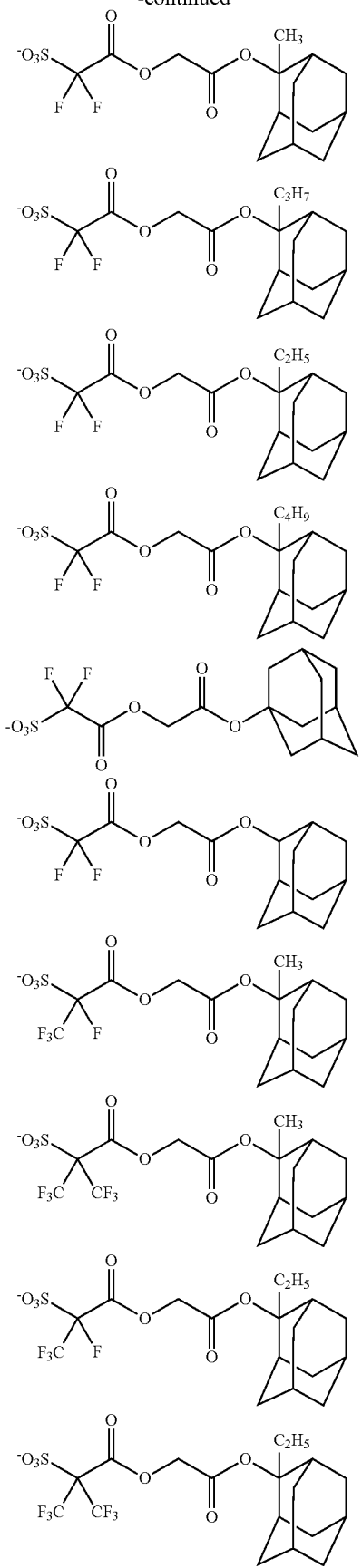
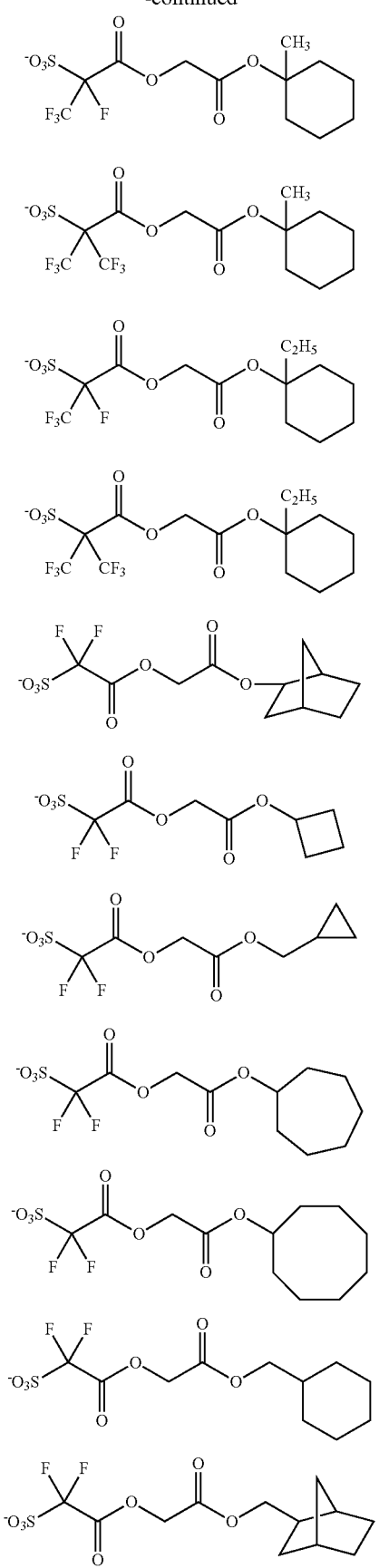

93
-continued
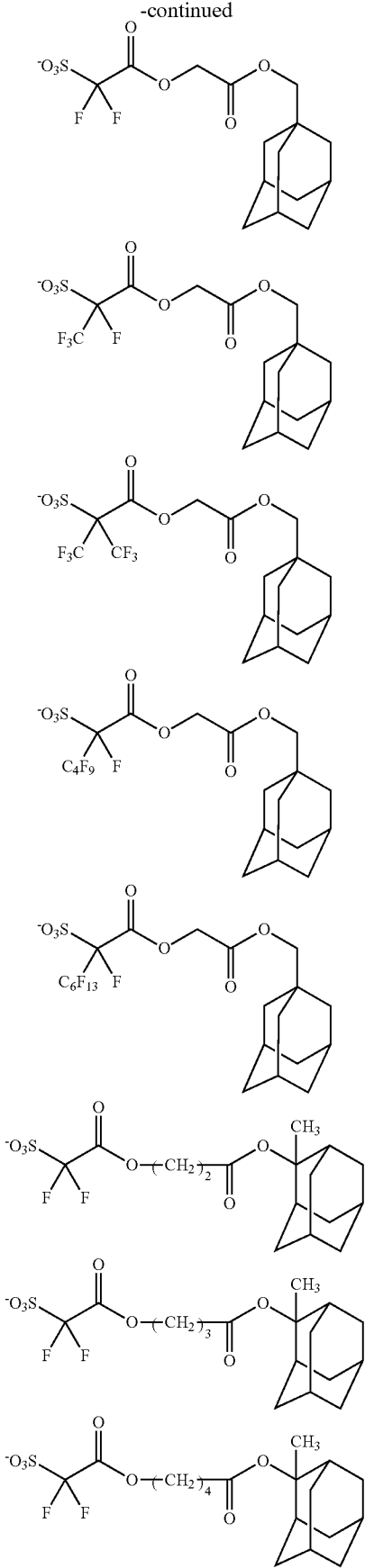
94
-continued
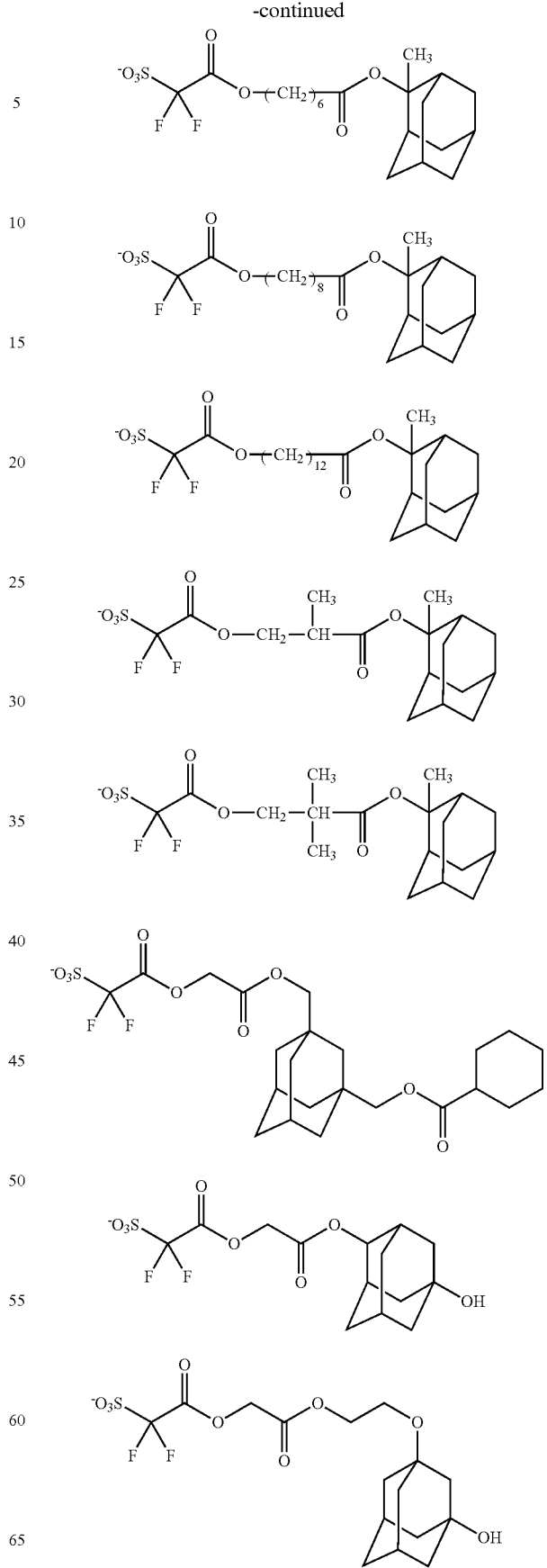

95
-continued
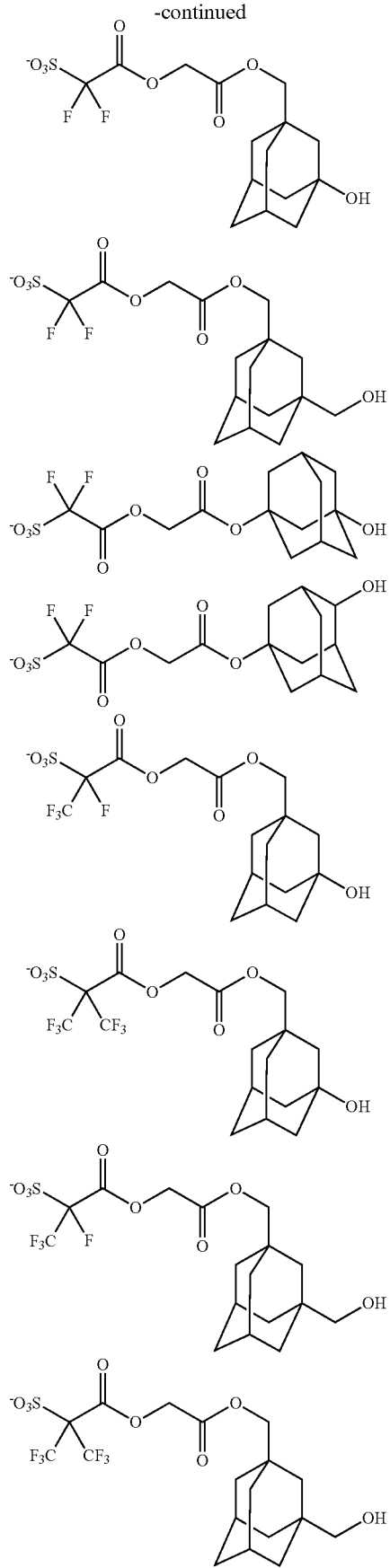
96
-continued
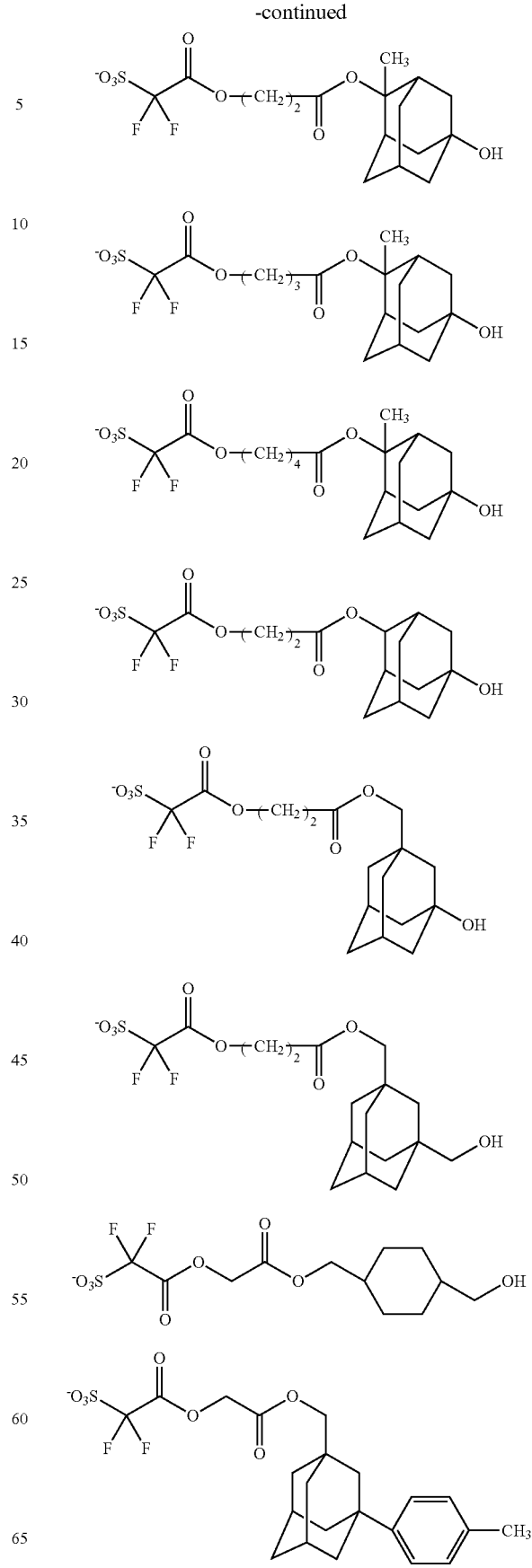

97
-continued
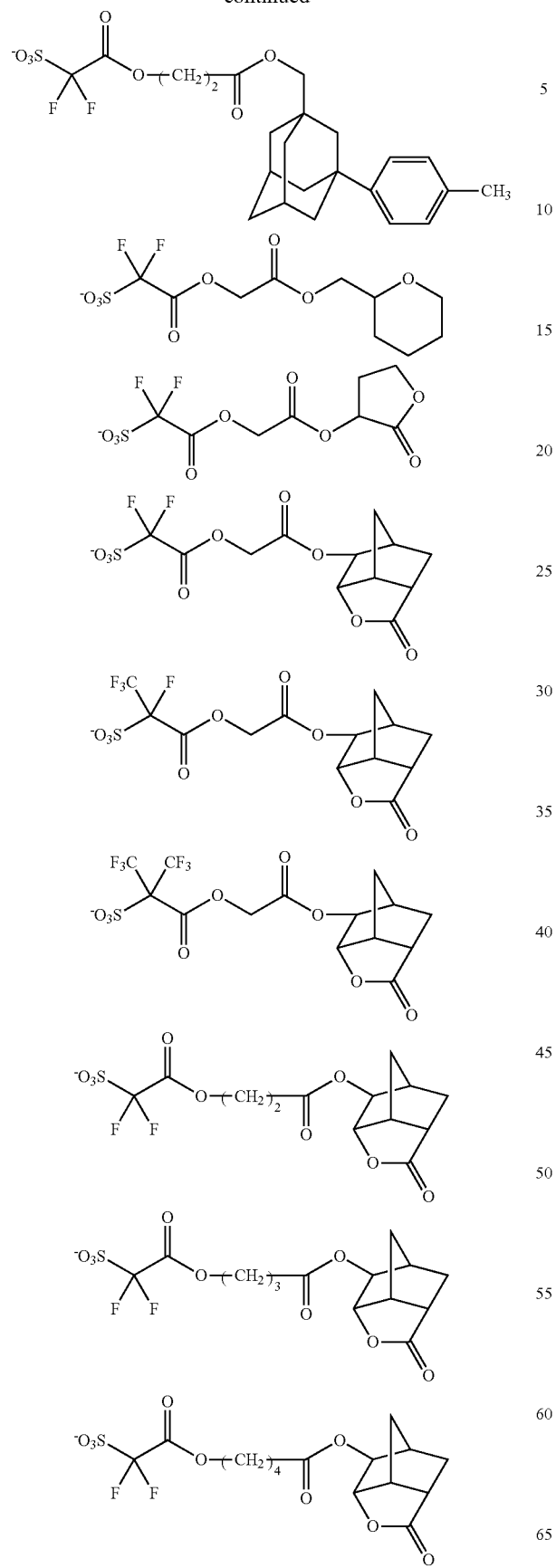
98
-continued
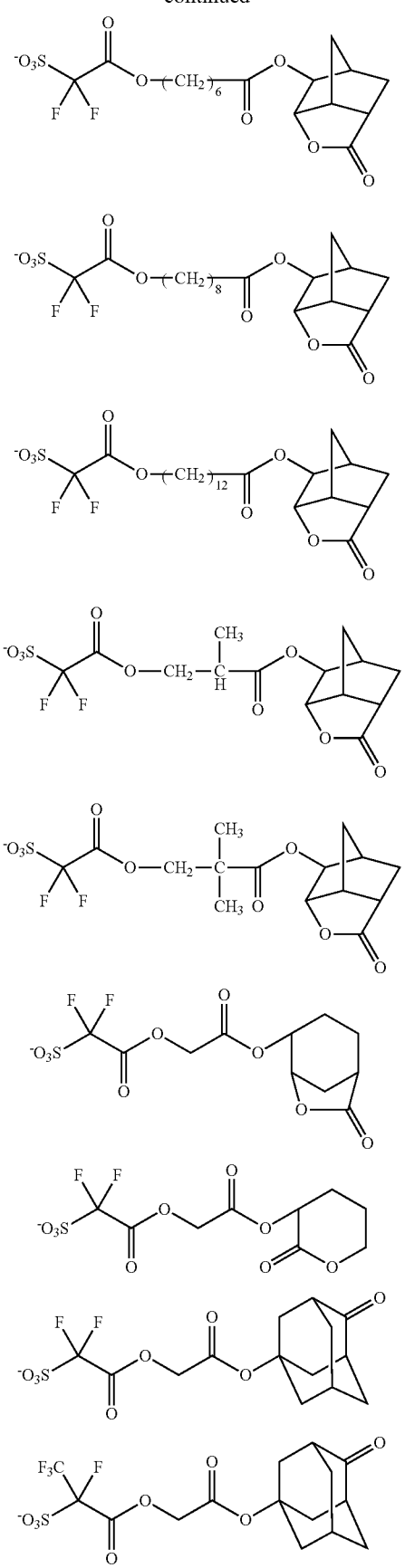

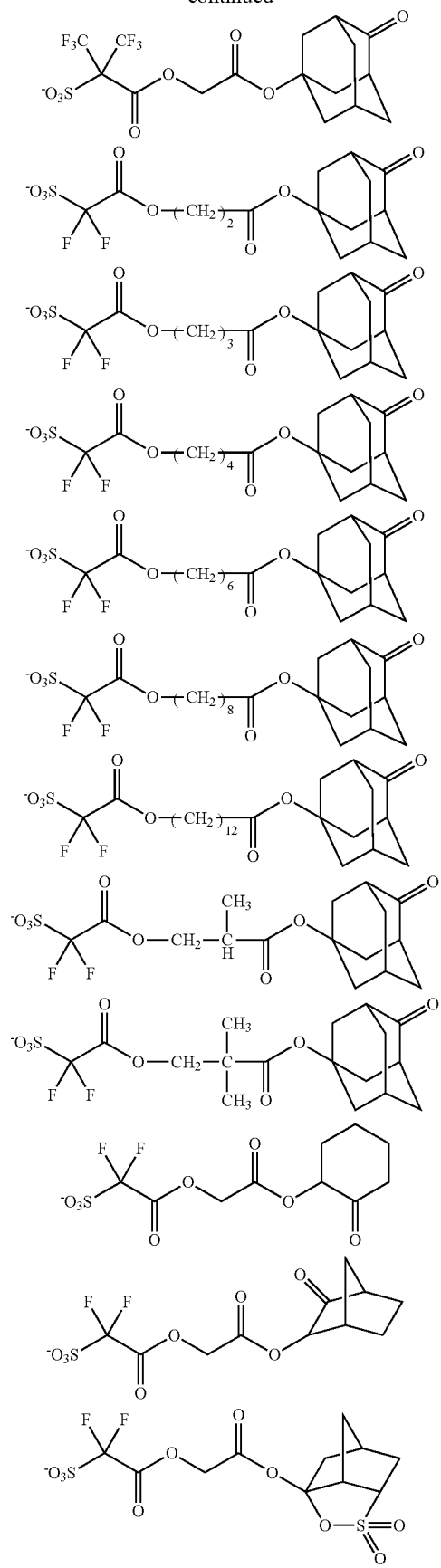
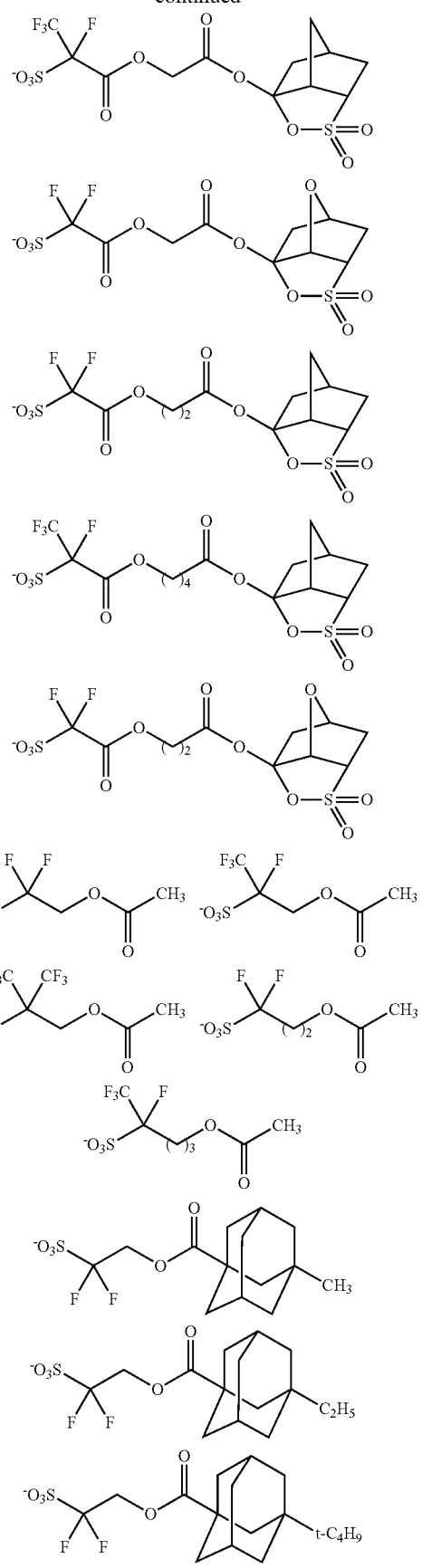

101
-continued
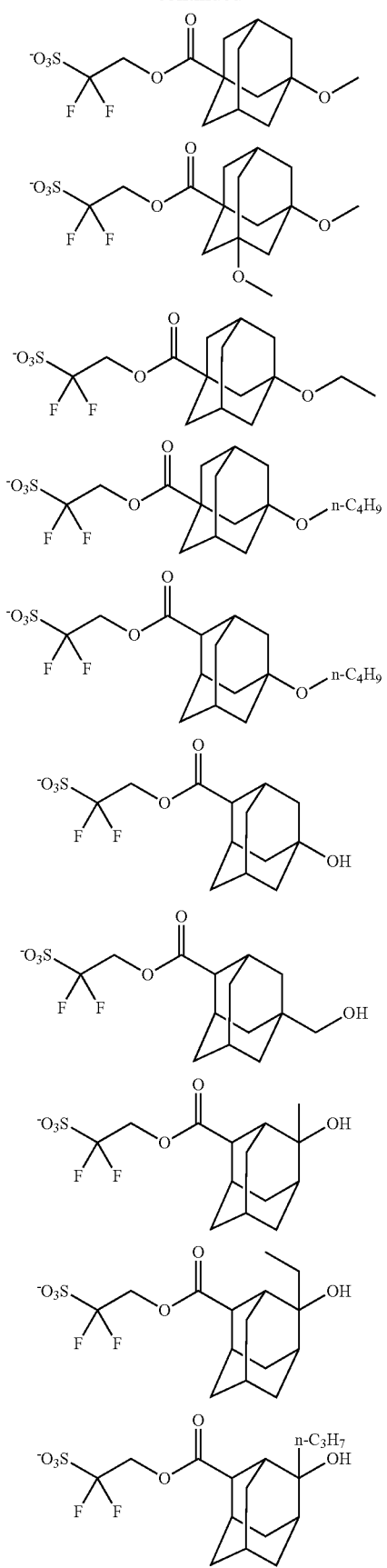
102
-continued
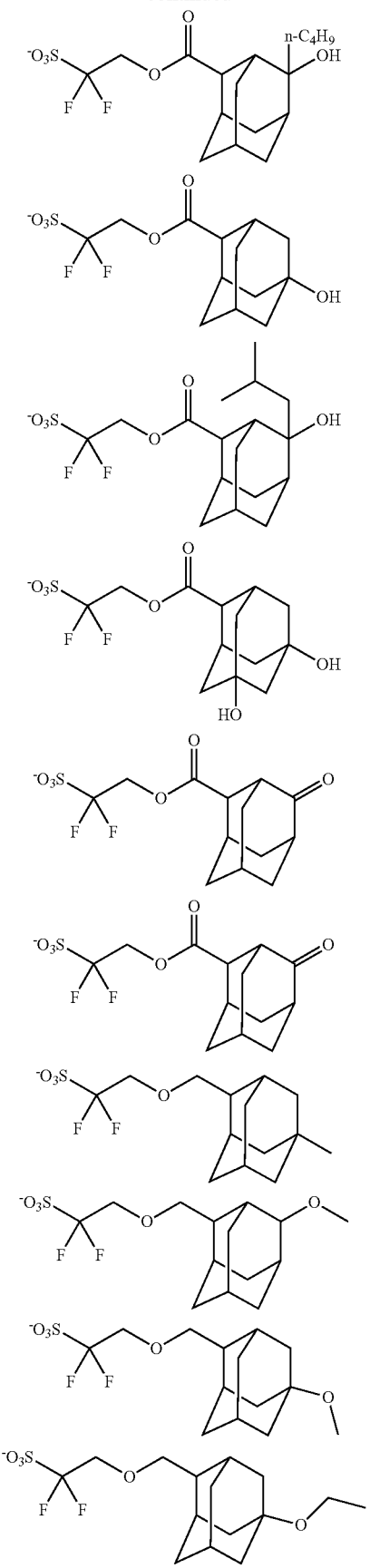

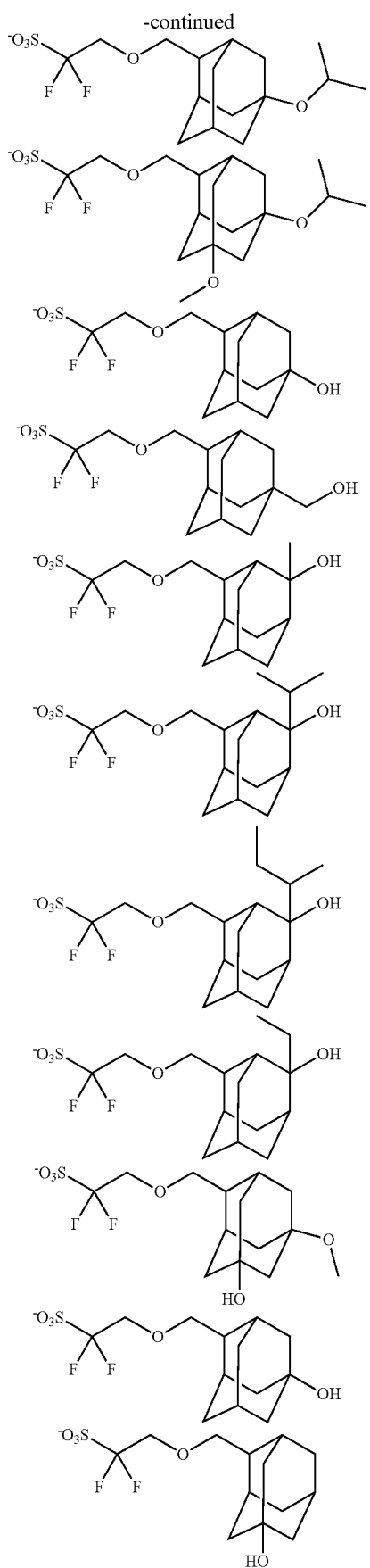
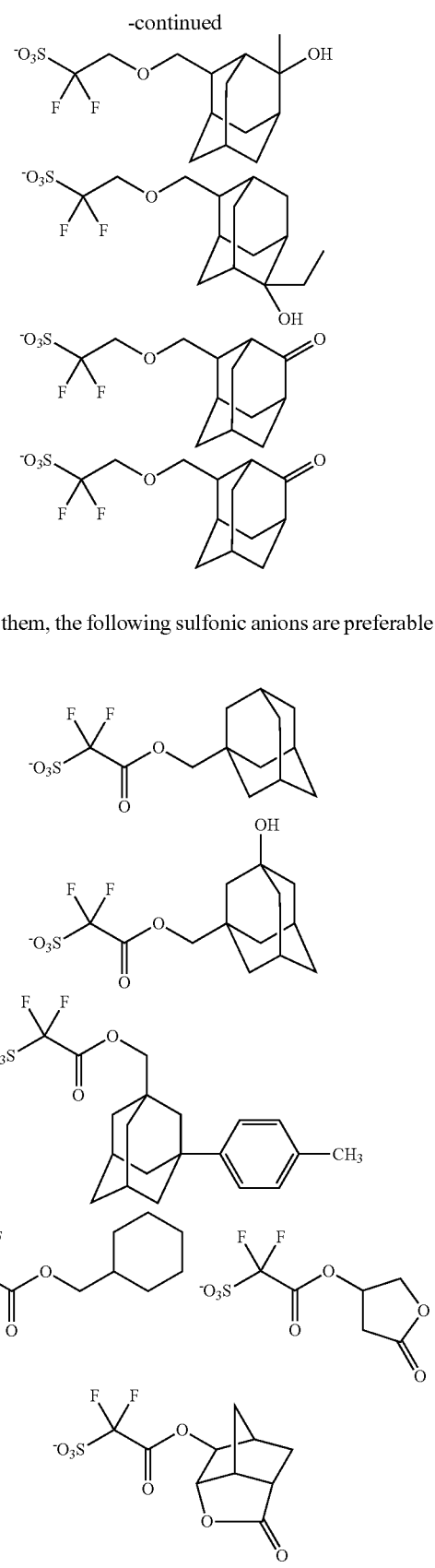
Among them, the following sulfonic anions are preferable.
Examples of the cation part represented by $Z^+$ include an onium cation such as a sulfonium cation, an iodonium cation, an ammonium cation, a benzothiazolium cation and a phosphonium cation, and a sulfonium cation and an iodonium cation are preferable, and an arylsulfonium cation is more preferable.

Preferable examples of the cation part represented by $Z^+$ include the cations represented by the formulae (b2-1) to (b2-4):

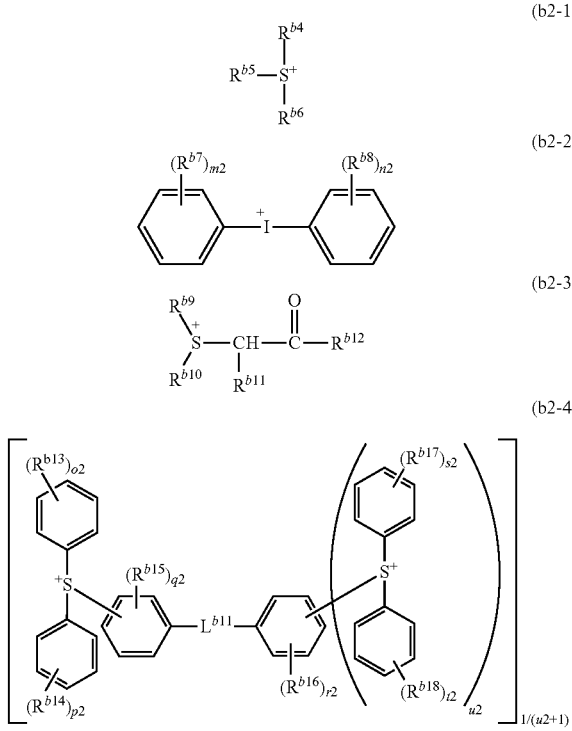

wherein $R^{b4}$, $R^{b5}$ and $R^{b6}$ each independently represent a C1-C30 aliphatic hydrocarbon group which can have one or more substituents selected from the group consisting of a hydroxyl group, a C1-C12 alkoxy group and a C6-C18 aromatic hydrocarbon group, a C3-C18 saturated cyclic hydrocarbon group which can have one or more substituents selected from the group consisting of a halogen atom, a C2-C4 acyl group and a glycidyloxy group, or a C6-C18 aromatic hydrocarbon group which can have one or more substituents selected from the group consisting of a halogen atom, a hydroxyl group, a C1-C18 aliphatic hydrocarbon group, a C3-C18 saturated cyclic hydrocarbon group or a C1-C12 alkoxy group, $R^{b7}$ and $R^{b8}$ are independently in each occurrence a hydroxyl group, a C1-C12 aliphatic hydrocarbon group or a C1-C12 alkoxy group, m2 and n2 independently represents an integer of 0 to 5, $R^{b9}$ and $R^{b10}$ each independently represent a C1-C18 aliphatic hydrocarbon group or a C3-C18 saturated cyclic hydrocarbon group, or $R^{b9}$ and $R^{b10}$ are bonded to form a C2-C11 divalent acyclic hydrocarbon group which forms a ring together with the adjacent $S^+$, and one or more —$CH_2$— in the divalent acyclic hydrocarbon group may be replaced by —CO—, —O— or —S—,
and
$R^{b11}$ represents a hydrogen atom, a C1-C18 aliphatic hydrocarbon group, a C3-C18 saturated cyclic hydrocarbon group or a C6-C18 aromatic hydrocarbon group, $R^{b12}$ represents a C1-C12 aliphatic hydrocarbon group, a C3-C18 saturated cyclic hydrocarbon group or a C6-C18 aromatic hydrocarbon group and the aromatic hydrocarbon group can have one or more substituents selected from the group consisting of a C1-C12 aliphatic hydrocarbon group, a C1-C12 alkoxy group, a C3-C18 saturated cyclic hydrocarbon group and an C2-C13 acyloxy group, or $R^{b11}$ and $R^{b12}$ are bonded each other to form a C1-C10 divalent acyclic hydrocarbon group which forms a 2-oxocycloalkyl group together with the adjacent —CHCO—, and one or more —$CH_2$— in the divalent acyclic hydrocarbon group may be replaced by —CO—, —O— or —S—, and $R^{b13}$, $R^{b14}$, $R^{b15}$, $R^{b16}$, $R^{b17}$ and $R^{b18}$ each independently represent a hydroxyl group, a C1-C12 aliphatic hydrocarbon group or a C1-C12 alkoxy group, $L^{b11}$ represents —S— or —O— and o2, p2, s2 and t2 each independently represents an integer of 0 to 5, q2 and r2 each independently represents an integer of 0 to 4, and u2 represents 0 or 1.

The aliphatic hydrocarbon group represented by $R^{b9}$ to $R^{b11}$ has preferably 1 to 12 carbon atoms. The saturated cyclic hydrocarbon group represented by $R^{b9}$ to $R^{b11}$ has preferably 3 to 18 carbon atoms and more preferably 4 to 12 carbon atoms.

Examples of the aliphatic hydrocarbon group and the aromatic hydrocarbon group include the same as described above. Preferable examples of the aliphatic hydrocarbon group include a methyl group, an ethyl group, a propyl group, an isopropyl group, a butyl group, a sec-butyl group, a tert-butyl group, a pentyl group, a hexyl group, an octyl group and a 2-ethylhexyl group. Preferable examples of the saturated cyclic hydrocarbon group include a cyclopropyl group, a cyclobutyl group, a cyclopentyl group, a cyclohexyl group, a cycloheptyl group, a cyclodecyl group, a 2-alkyl-a-adamantyl group, a 1-(1-adamantyl)-1-alkyl group and an isobornyl group. Preferable examples of the aromatic group include a phenyl group, a 4-methylphenyl group, a 4-ethylphenyl group, a 4-tert-butylphenyl group, a 4-cyclohexylphenyl group, a 4-methoxyphenyl group, a biphenyl group and a naphthyl group. Examples of the aliphatic hydrocarbon group having an aromatic hydrocarbon group include a benzyl group. Examples of the alkoxy group include a methoxy group, an ethoxy group, a propoxy group, an isopropoxy group, a butoxy group, a sec-butoxy group, a tert-butoxy group, a pentyloxy group, a hexyloxy group, a heptyloxy group, an octyloxy group, a 2-ethylhexyloxy group, a nonyloxy group, a decyloxy group, an undecyloxy group and a dodecyloxy group.

Examples of the C3-C12 divalent acyclic hydrocarbon group formed by bonding $R^{b9}$ and $R^{b10}$ include a trimethylene group, a tetramethylene group and a pentamethylene group. Examples of the ring group formed together with the adjacent $S^+$ and the divalent acyclic hydrocarbon group include a thiolan-1-ium ring (tetrahydrothiphenium ring), a thian-1-ium ring and a 1,4-oxathian-4-ium ring. A C3-C7 divalent acyclic hydrocarbon group is preferable.

Examples of the C1-C10 divalent acyclic hydrocarbon group formed by bonding $R^{b11}$ and $R^{b12}$ include a methylene group, an ethylene group, a trimethylene group, a tetramethylene group and a pentamethylene group and examples of the ring group include the followings.

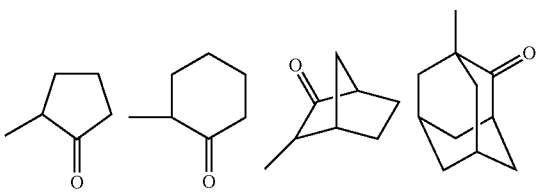

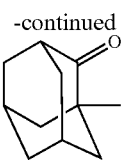

Among the above-mentioned cations, preferred is the cation represented by the formula (b2-1), and more preferred is the cation represented by the formula (b2-1-1), and especially preferred is a triphenylsulfonium cation.

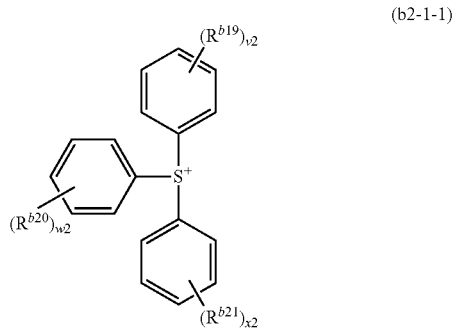
(b2-1-1)

wherein $R^{b19}$, $R^{b20}$ and $R^{b21}$ are independently in each occurrence a hydroxyl group, a C1-C18 aliphatic hydrocarbon group, a C3-C18 saturated cyclic hydrocarbon group or a C1-C12 alkoxy group, and one or more hydrogen atoms in the aliphatic hydrocarbon group can be replaced by a hydroxyl group, a C1-C12 alkoxy group or a C6-C18 aromatic hydrocarbon group, one or more hydrogen atoms of the saturated cyclic hydrocarbon group can be replaced by a halogen atom, a C2-C4 acyl group or a glycidyloxy group, and v2, w2 and x2 independently each represent an integer of 0 to 5. The aliphatic hydrocarbon group preferably has 1 to 12 carbon atoms, and the saturated cyclic hydrocarbon group preferably has 4 to 18 carbon atoms, and it is preferred that v2, w2 and x2 independently each represent 0 or 1. It is preferred that $R^{b19}$, $R^{b20}$ and $R^{b21}$ are independently halogen atom (preferably a chlorine atom), a hydroxyl group, a C1-C12 alkyl group or a C1-C12 alkoxy group.

Examples of the cation represented by the formula (b2-1) include the followings.

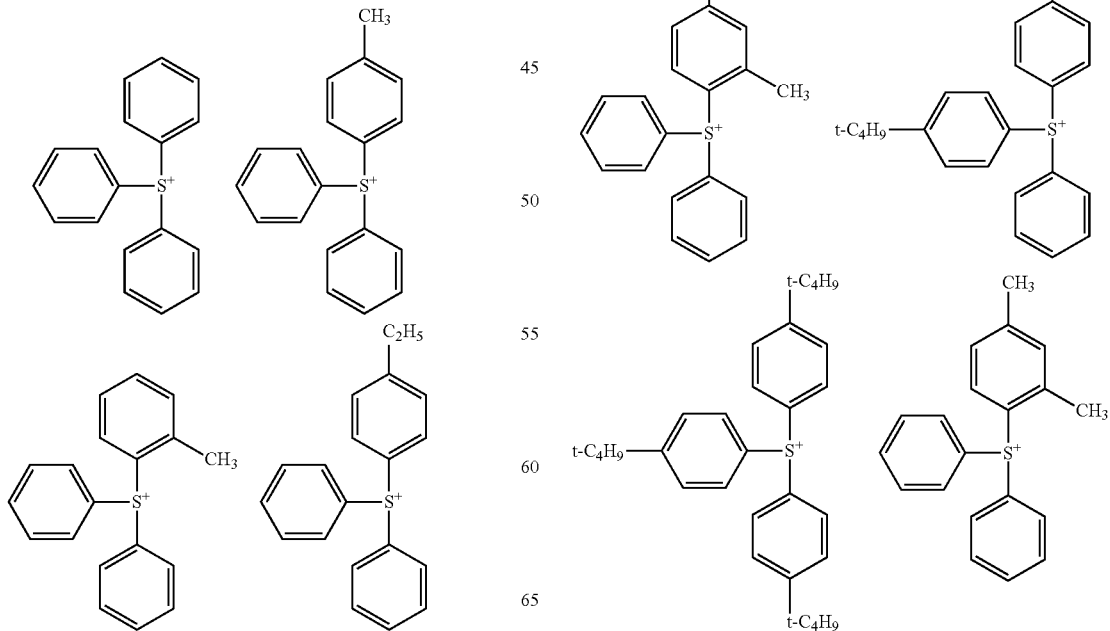

-continued
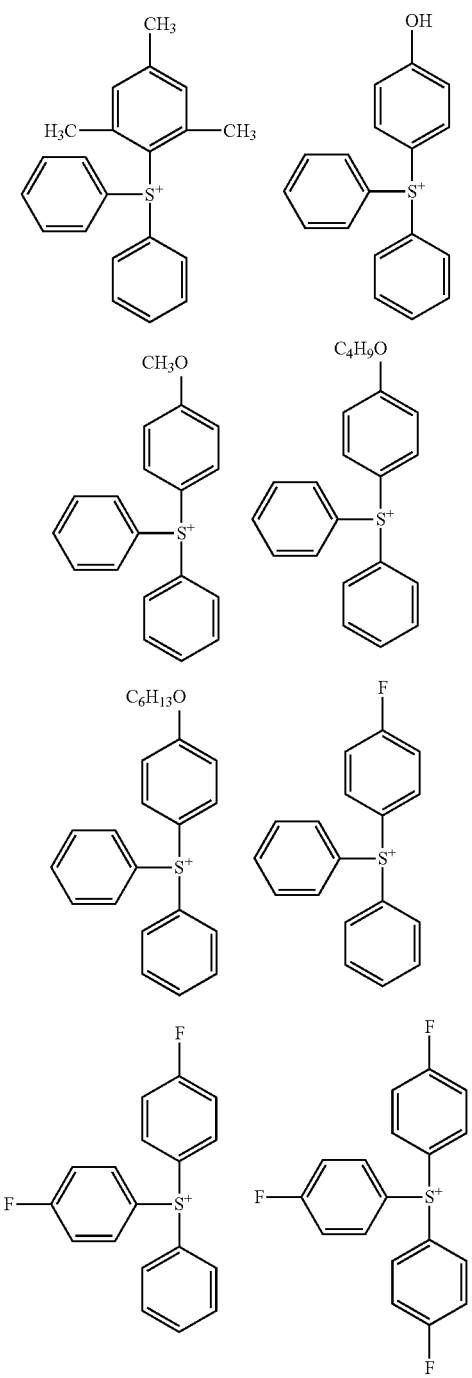
Examples of the cation represented by the formula (b2-2) include the followings.
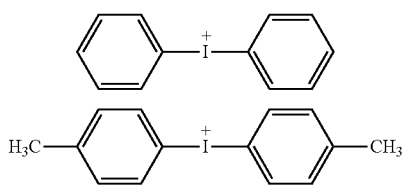
-continued
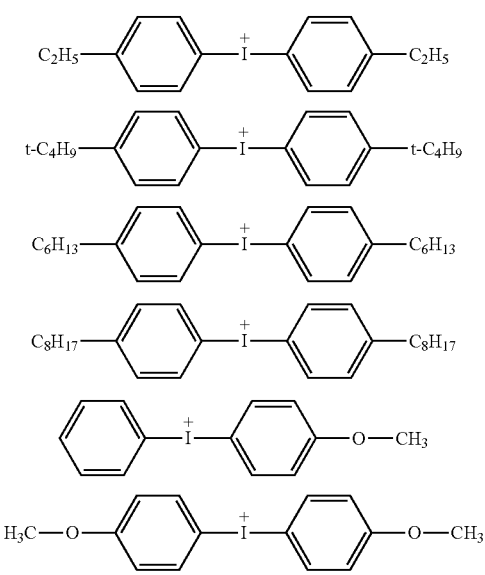
Examples of the cation represented by the formula (b2-3) include the followings.
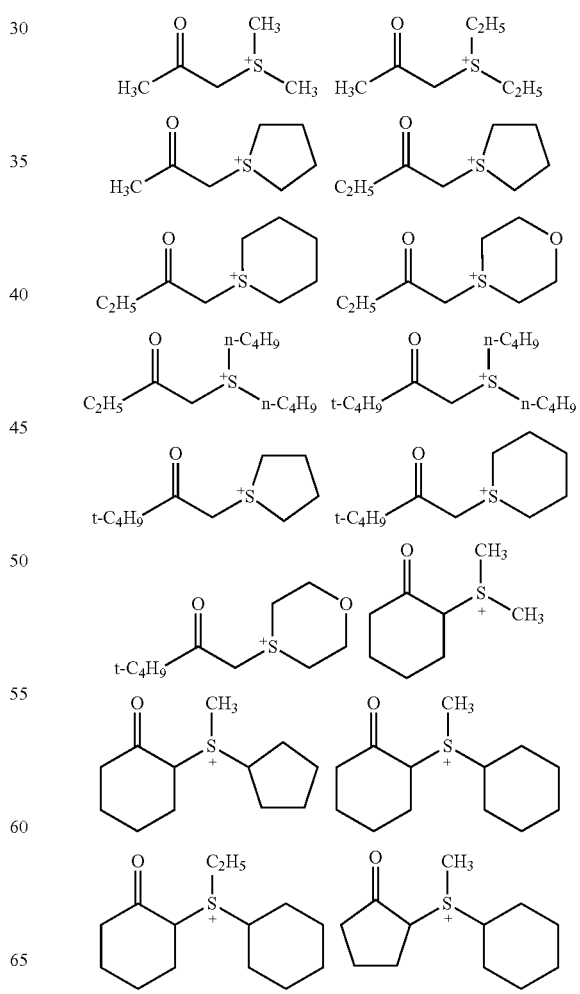

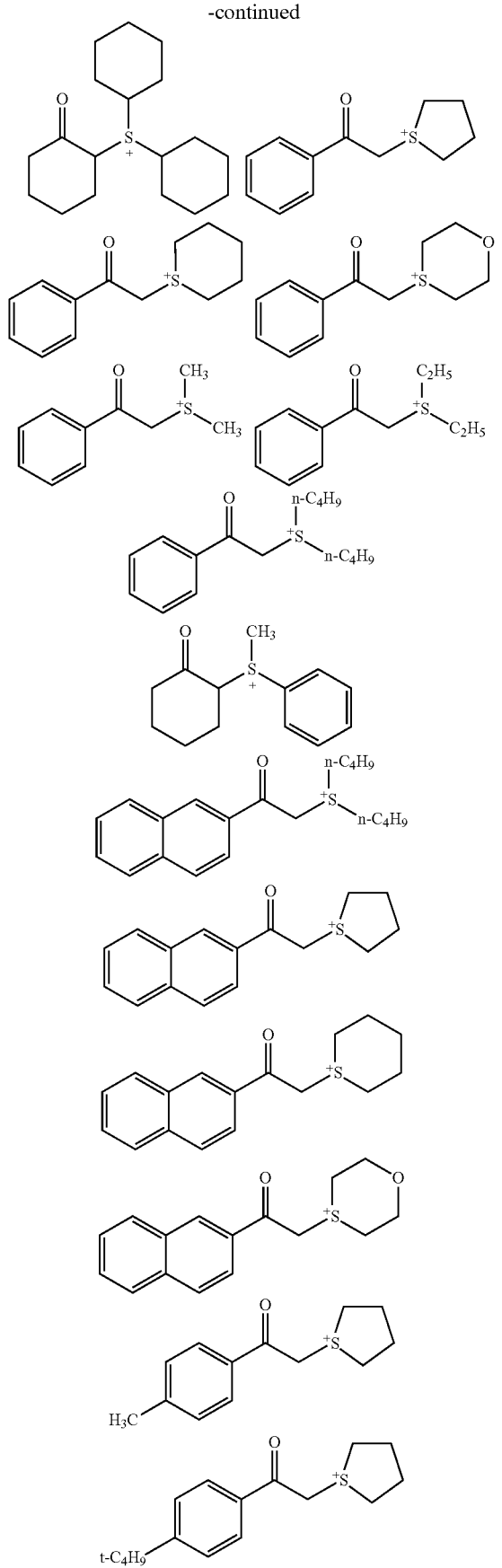
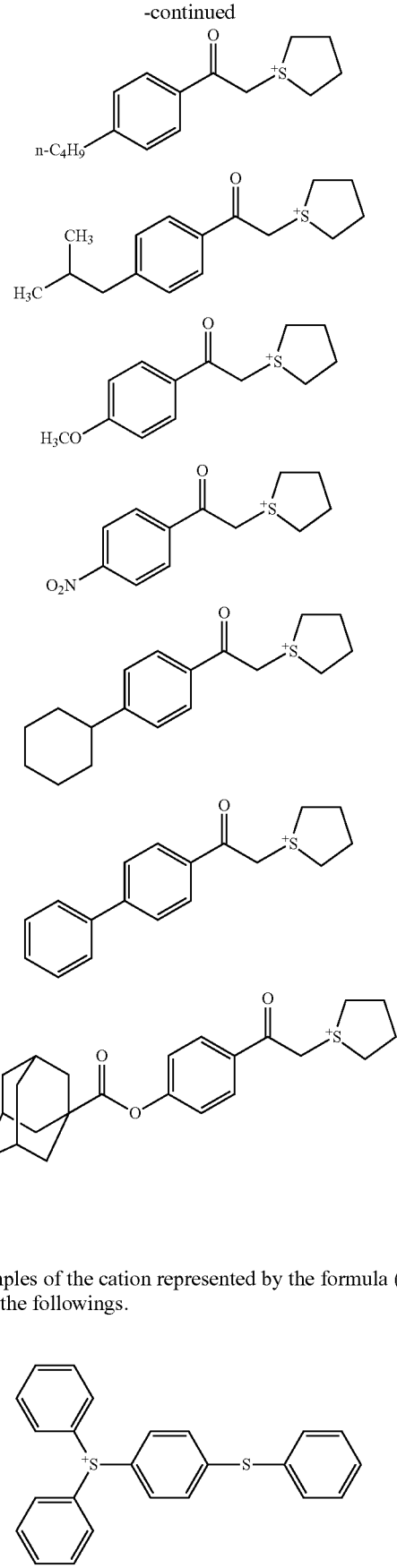
Examples of the cation represented by the formula (b2-4) include the followings.
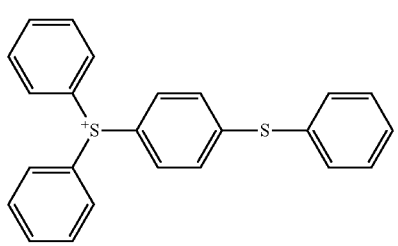

113
-continued
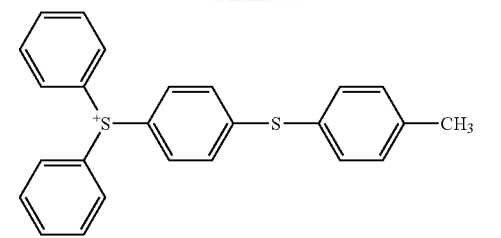
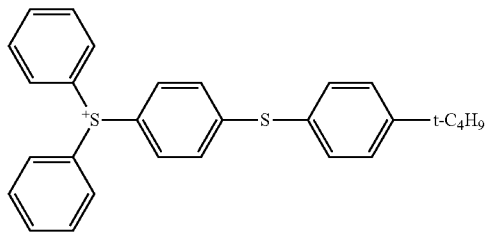
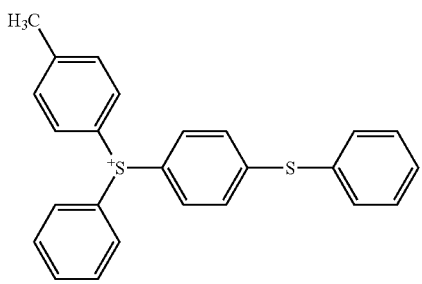
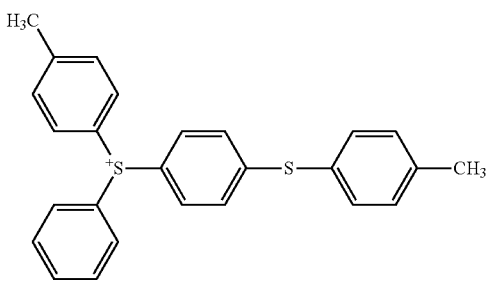
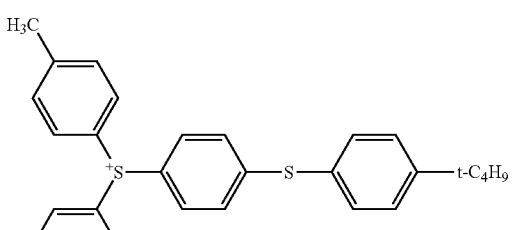
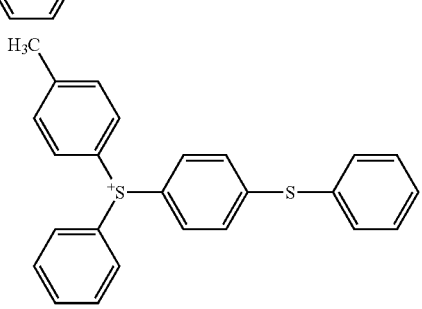
114
-continued
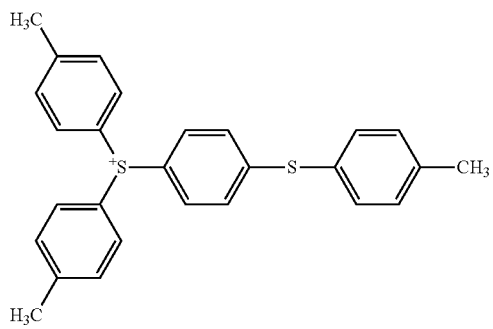
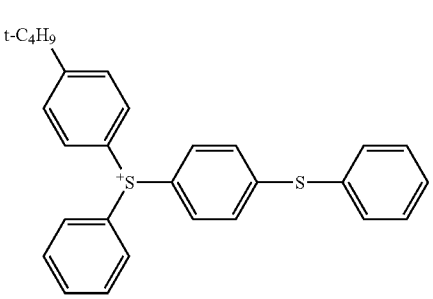
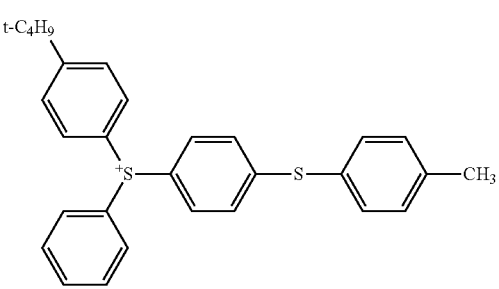
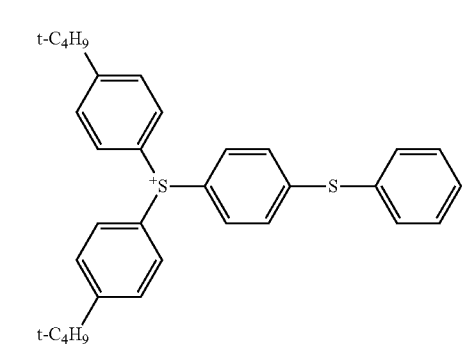
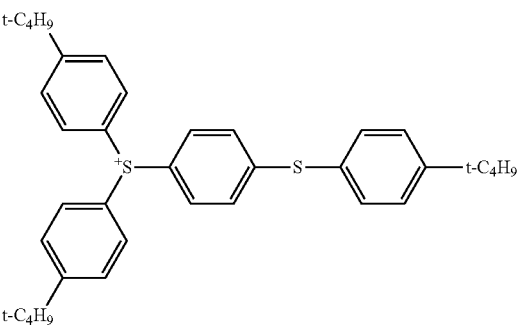

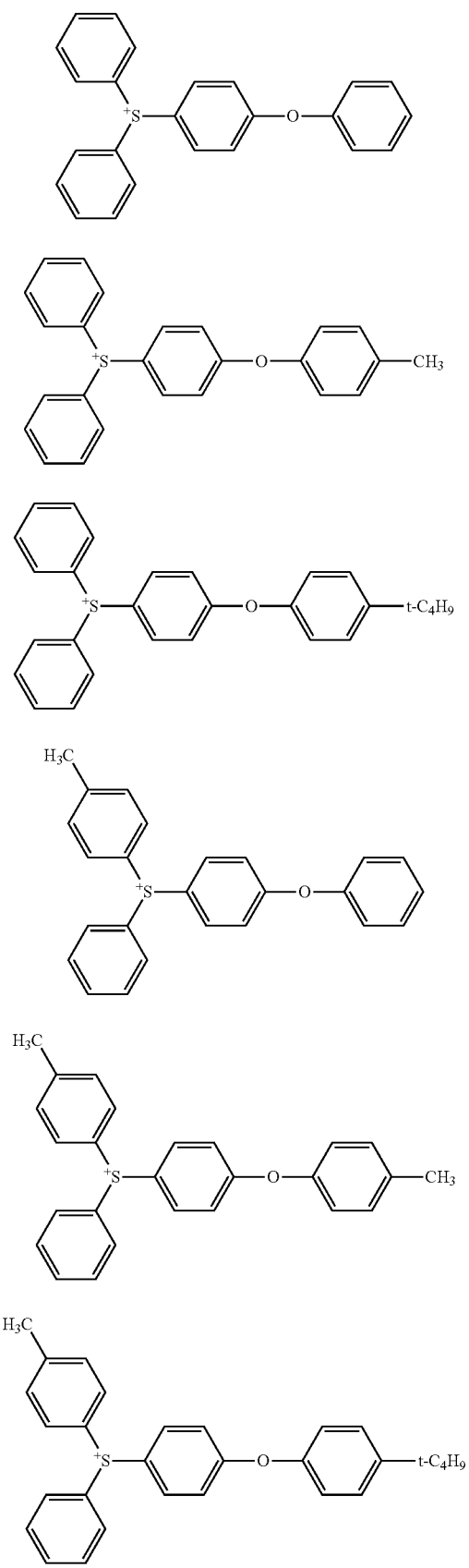

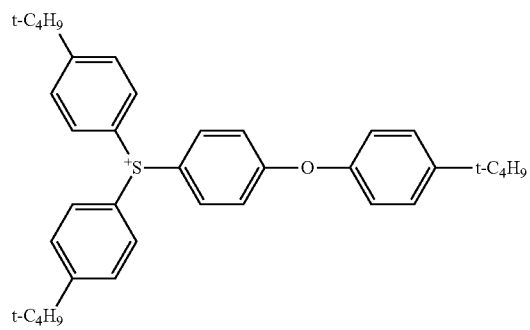
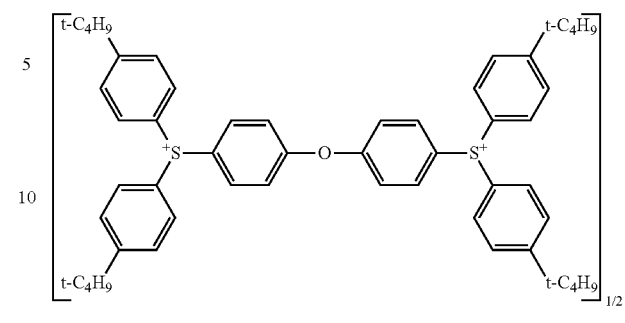
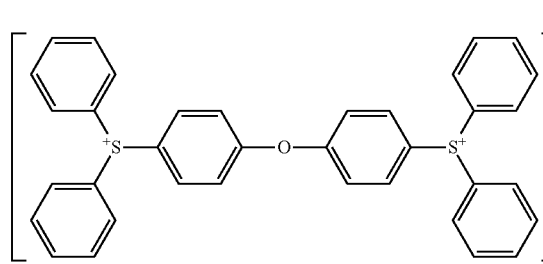
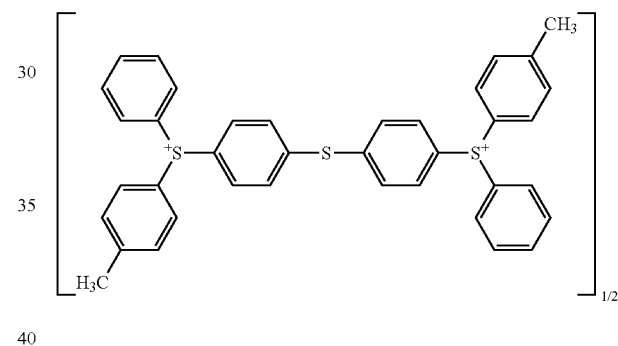
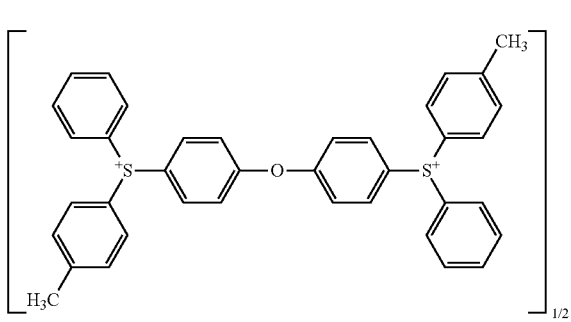
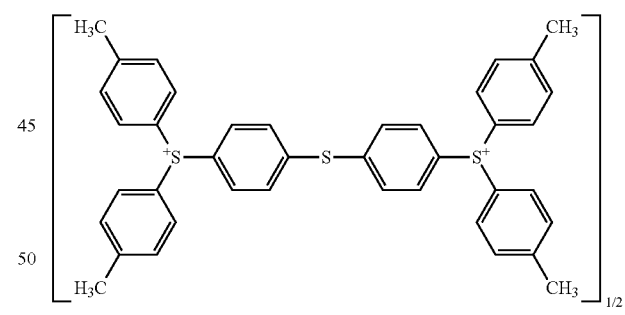
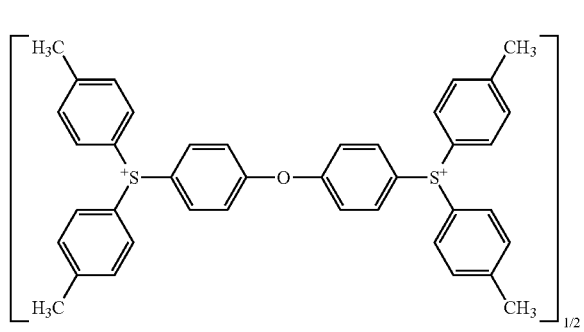
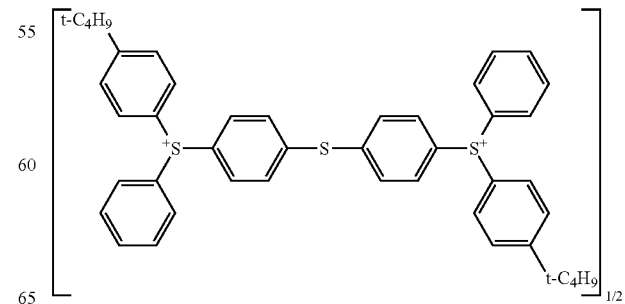
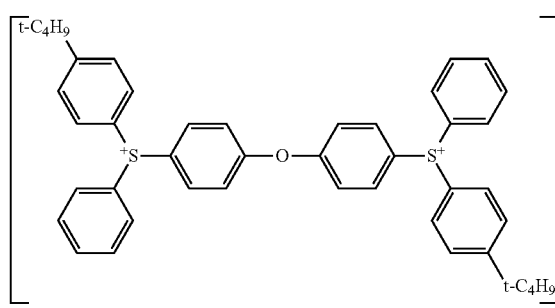

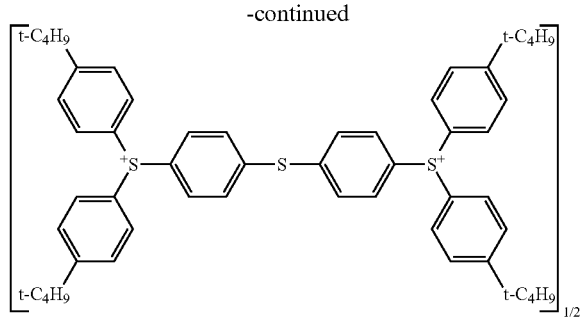

Examples of the salt represented by the formula (B1) include a salt wherein the anion part is any one of the above-mentioned anion part and the cation part is any one of the above-mentioned cation part. Preferable examples of the salt include a combination of any one of anions represented by the formulae (b1-1-1) to (b1-1-9) and the cation represented by the formulae (b2-1-1), and a combination of any one of anions represented by the formulae (b1-1-3) to (b1-1-5) and the cation represented by the formulae (b2-3).

The salt represented by the formulae (B1-1) to (B1-17) are preferable, and the salt represented by the formulae (B1-1), (B1-2), (B1-6), (B1-11), (B1-12), (B1-13) and (B1-14) are more preferable.

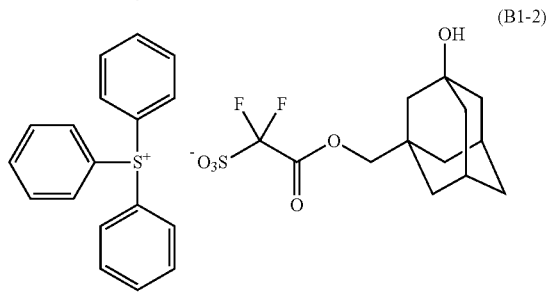

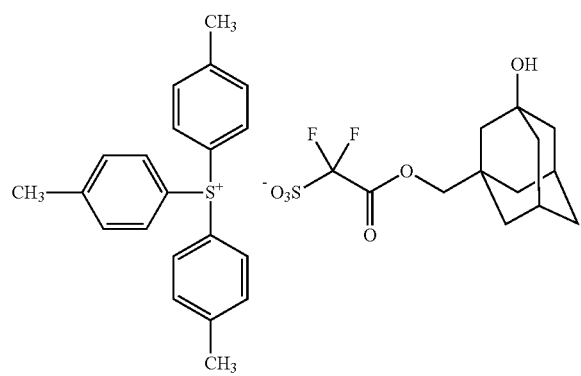

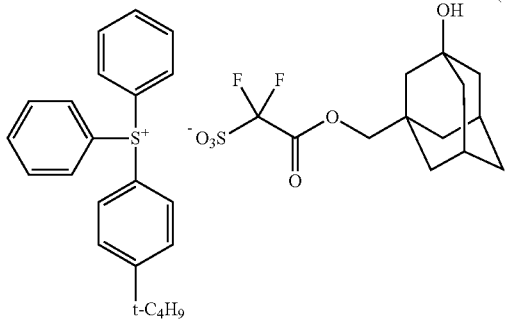

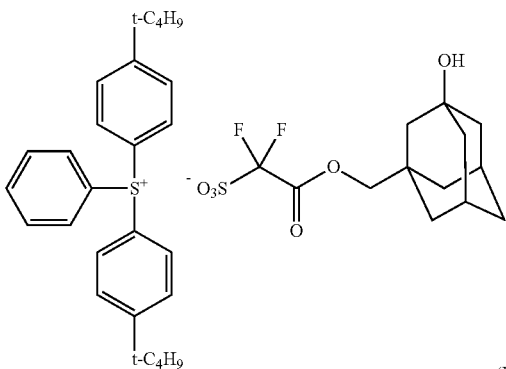

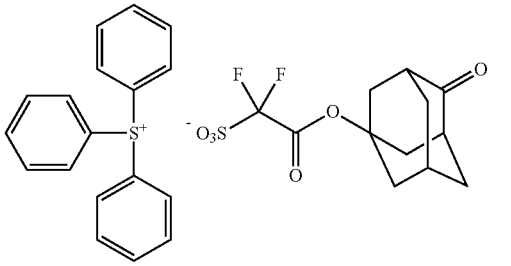

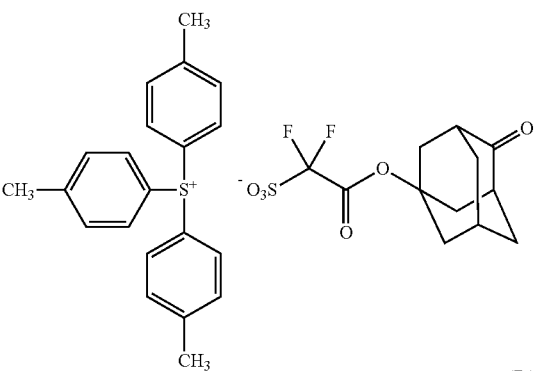

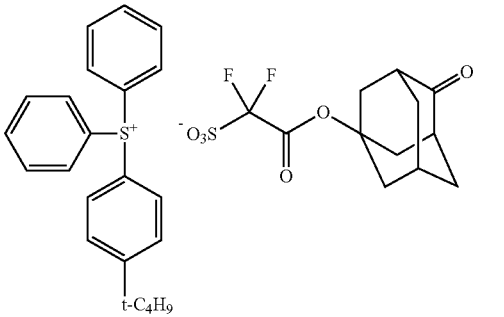

-continued (B1-9)
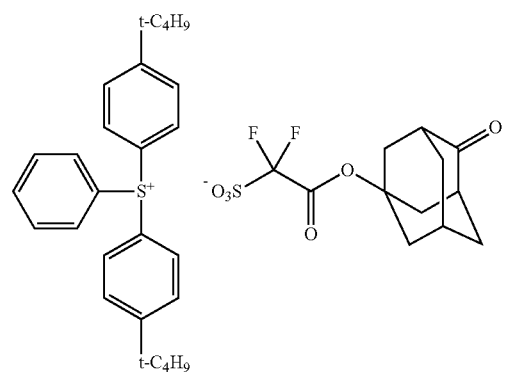

(B1-10)
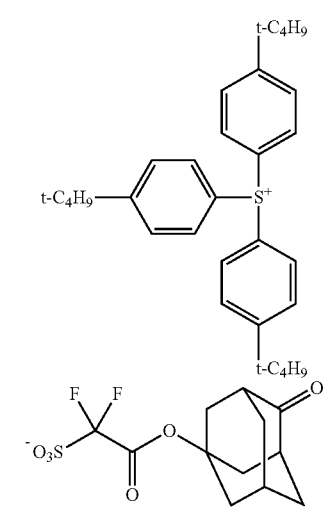

(B1-11)
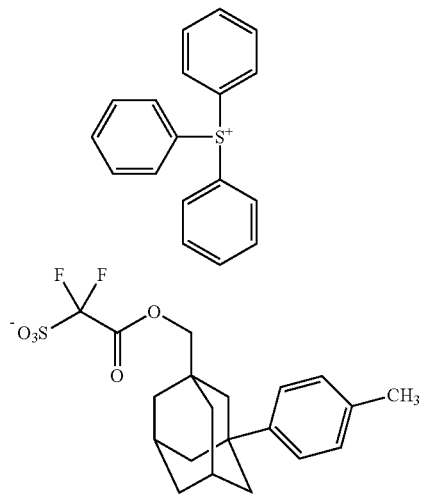

(B1-12)
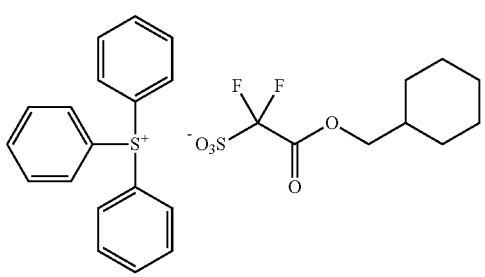

-continued (B1-13)
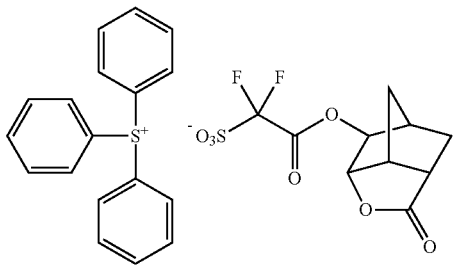

(B1-14)
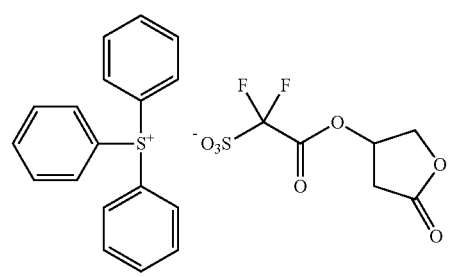

(B1-15)
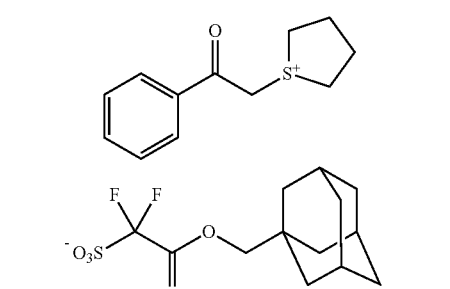

(B1-16)
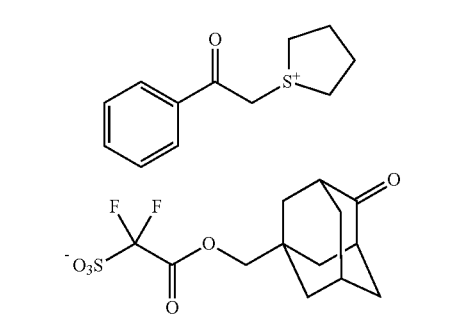

(B1-17)
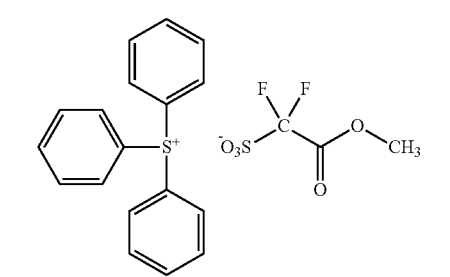

Two or more kinds of the acid generator can be used in combination.

The content of the acid generator is preferably 1 part by weight or more and more preferably 3 parts by weight or more per 100 parts by weight of the resin. The content of the acid generator is preferably 30 parts by weight or less and more preferably 25 parts by weight or less per 100 parts by weight of the resin.

The photoresist composition of the present invention can contain a basic compound other than Compound (I) as a quencher.

The basic compound is preferably a basic nitrogen-containing organic compound, and examples thereof include an amine compound such as an aliphatic amine and an aromatic amine and an ammonium salt. Examples of the aliphatic amine include a primary amine, a secondary amine and a tertiary amine. Examples of the aromatic amine include an aromatic amine in which aromatic ring has one or more amino groups such as aniline and a heteroaromatic amine such as pyridine. Preferable examples thereof include an aromatic amine represented by the formula (C2):

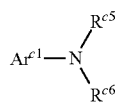
(C2)

wherein $Ar^{c1}$ represents an aromatic hydrocarbon group, and $R^{c5}$ and $R^{c6}$ each independently represent a hydrogen atom, an aliphatic hydrocarbon group, a saturated cyclic hydrocarbon group or an aromatic hydrocarbon group, and the aliphatic hydrocarbon group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group.

The aliphatic hydrocarbon group is preferably an alkyl group and the saturated cyclic hydrocarbon group is preferably a cycloalkyl group. The aliphatic hydrocarbon group preferably has 1 to 6 carbon atoms. The saturated cyclic hydrocarbon group preferably has 5 to 10 carbon atoms. The aromatic hydrocarbon group preferably has 6 to 10 carbon atoms.

As the aromatic amine represented by the formula (C2), an amine represented by the formula (C2-1):

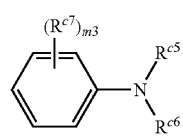
(C2-1)

wherein $R^{c5}$ and $R^{c6}$ are the same as defined above, and $R^{c7}$ is independently in each occurrence an aliphatic hydrocarbon group, an alkoxy group, a saturated cyclic hydrocarbon group or an aromatic hydrocarbon group, and the aliphatic hydrocarbon group, the alkoxy group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group, and m3 represents an integer of 0 to 3, is preferable. The aliphatic hydrocarbon group is preferably an alkyl group and the saturated cyclic hydrocarbon group is preferably a cycloalkyl group. The aliphatic hydrocarbon group preferably has 1 to 6 carbon atoms.

The saturated cyclic hydrocarbon group preferably has 5 to 10 carbon atoms. The aromatic hydrocarbon group preferably has 6 to 10 carbon atoms. The alkoxy group preferably has 1 to 6 carbon atoms.

Examples of the aromatic amine represented by the formula (C2) include 1-naphthylamine, 2-naphthylamine, aniline, diisopropylaniline, 2-methylaniline, 3-methylaniline, 4-methylaniline, 4-nitroaniline, N-methylaniline, N,N-dimethylaniline, and diphenylamine, and among them, preferred is diisopropylaniline and more preferred is 2,6-diisopropylaniline.

Other examples of the basic compound include amines represented by the formulae (C3) to (C11):

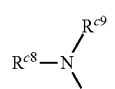
(C3)

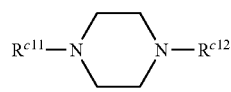
(C4)

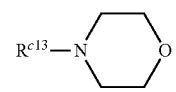
(C5)

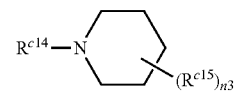
(C6)

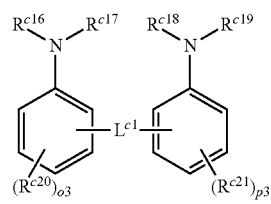
(C7)

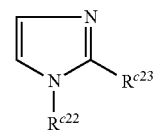
(C8)

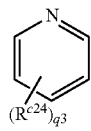
(C9)

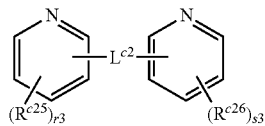
(C10)

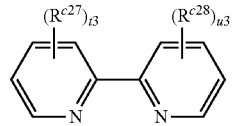
(C11)

wherein $R^{c8}$, $R^{c20}$, $R^{c21}$, and $R^{c23}$ to $R^{c28}$ each independently represent an aliphatic hydrocarbon group, an alkoxy group, a saturated cyclic hydrocarbon group or an aromatic hydrocarbon group, and the aliphatic hydrocarbon group, the alkoxy group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group,
$R^{c9}$, $R^{c10}$, $R^{c11}$ to $R^{c14}$, $R^{c16}$ to $R^{c19}$, and $R^{c22}$ each independently represents a hydrogen atom, an aliphatic hydrocarbon group, a saturated cyclic hydrocarbon group or an aromatic hydrocarbon group, and the aliphatic hydrocarbon group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group,
$R^{c15}$ is independently in each occurrence an aliphatic hydrocarbon group, a saturated cyclic hydrocarbon group or an alkanoyl group, $L^{c1}$ and $L^{c2}$ each independently represents a divalent aliphatic hydrocarbon group, —CO—, —C(=NH)—, —C(=$NR^{c3}$)—, —S—, —S—S— or a combination thereof and $R^{c3}$ represents a C1-C4 alkyl group, O3 to u3 each independently represents an integer of 0 to 3 and n3 represents an integer of 0 to 8.

The aliphatic hydrocarbon group has preferably 1 to 6 carbon atoms, and the saturated cyclic hydrocarbon group has preferably 3 to 6 carbon atoms, and the alkanoyl group has preferably 2 to 6 carbon atoms, and the divalent aliphatic hydrocarbon group has preferably 1 to 6 carbon atoms. The divalent aliphatic hydrocarbon group is preferably an alkylene group.

Examples of the amine represented by the formula (C3) include hexylamine, heptylamine, octylamine, nonylamine, decylamine, dibutylamine, dipentylamine, dihexylamine, diheptylamine, dioctylamine, dinonylamine, didecylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethydipentylamine, ethyldihexylamine, ethydiheptylamine, ethyldioctylamine, ethyldinonylamine, ethyldidecylamine, dicyclohexylmethylamine, tris[2-(2-methoxyethoxy)ethyl]amine, triisopropanolamine, ethylenediamine, tetramethylenediamine, hexamethylenediamine, 4,4'-diamino-1,2-diphenylethane, 4,4'-diamino-3,3'-dimethyldiphenylmethane and 4,4'-diamino-3,3'-diethyldiphenylmethane.

Examples of the amine represented by the formula (C4) include piperazine. Examples of the amine represented by the formula (C5) include morpholine. Examples of the amine represented by the formula (C6) include piperidine and hindered amine compounds having a piperidine skeleton as disclosed in JP 11-52575 A. Examples of the amine represented by the formula (C7) include 2,2'-methylenebisaniline. Examples of the amine represented by the formula (C8) include imidazole and 4-methylimidazole. Examples of the amine represented by the formula (C9) include pyridine and 4-methylpyridine. Examples of the amine represented by the formula (C10) include di-2-pyridyl ketone, 1,2-di(2-pyridyl)ethane, 1,2-di(4-pyridyl)ethane, 1,3-di(4-pyridyl)propane, 1,2-bis(2-pyridyl)ethene, 1,2-bis(4-pyridyl)ethene, 1,2-di(4-pyridyloxy)ethane, 4,4'-dipyridyl sulfide, 4,4'-dipyridyl disulfide, 2,2'-dipyridylamine and 2,2'-dipicolylamine. Examples of the amine represented by the formula (C11) include bipyridine.

When the nitrogen-containing basic compound other than Compound (I) is used, the present photoresist composition preferably includes 0.01 to 1% by weight of the nitrogen-containing basic compound based on sum of solid component.

The photoresist composition of the present invention usually contains one or more solvents. Examples of the solvent include a glycol ether ester such as ethyl cellosolve acetate, methyl cellosolve acetate and propylene glycol monomethyl ether acetate; a glycol ether such as propylene glycol monomethyl ether; an acyclic ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone.

The amount of the solvent is usually 90% by weight or more, preferably 92% by weight or more preferably 94% by weight or more based on total amount of the photoresist composition of the present invention. The amount of the solvent is usually 99.9% by weight or less and preferably 99% by weight or less based on total amount of the photoresist composition of the present invention.

The photoresist composition of the present invention can contain, if necessary, a small amount of various additives such as a sensitizer, a dissolution inhibitor, other polymers, a surfactant, a stabilizer and a dye as long as the effect of the present invention is not prevented.

The photoresist composition of the present invention is useful for a chemically amplified photoresist composition.

A photoresist pattern can be produced by the following steps (1) to (5):
(1) a step of applying the photoresist composition of the present invention on a substrate,
(2) a step of forming a photoresist film by conducting drying,
(3) a step of exposing the photoresist film to radiation,
(4) a step of baking the exposed photoresist film, and
(5) a step of developing the baked photoresist film with an alkaline developer, thereby forming a photoresist pattern.

The applying of the photoresist composition on a substrate is usually conducted using a conventional apparatus such as spin coater. The photoresist composition is preferably filtrated with filter having 0.2 μm of a pore size before applying. Examples of the substrate include a silicon wafer or a quartz wafer on which a sensor, a circuit, a transistor or the like is formed.

The formation of the photoresist film is usually conducted using a heating apparatus such as hot plate or a decompressor, and the heating temperature is usually 50 to 200° C., and the operation pressure is usually 1 to $1.0*10^5$ Pa.

The photoresist film obtained is exposed to radiation using an exposure system. The exposure is usually conducted through a mask having a pattern corresponding to the desired photoresist pattern. Examples of the exposure source include a light source radiating laser light in a UV-region such as a KrF excimer laser (wavelength: 248 nm), an ArF excimer laser (wavelength: 193 nm) and a $F_2$ laser (wavelength: 157 nm), and a light source radiating harmonic laser light in a far UV region or a vacuum UV region by wavelength conversion of laser light from a solid laser light source (such as YAG or semiconductor laser).

The temperature of baking of the exposed photoresist film is usually 50 to 200° C., and preferably 70 to 150° C.

The development of the baked photoresist film is usually carried out using a development apparatus. The alkaline developer used may be any one of various alkaline aqueous solution used in the art. Generally, an aqueous solution of tetramethylammonium hydroxide or (2-hydroxyethyl)trimethylammoniumhydroxide (commonly known as "choline") is often used. After development, the photoresist pattern formed is preferably washed with ultrapure water, and the remained water on the photoresist pattern and the substrate is preferably removed.

The photoresist composition of the present invention provides a photoresist pattern showing good Mask Error Enhancement Factor (MEEF), and therefore, the photoresist composition of the present invention is suitable for ArF excimer laser lithography, KrF excimer laser lithography, ArF immersion lithography, EUV (extreme ultraviolet) lithography, EUV immersion lithography and EB (electron beam) lithography. Further, the photoresist composition of the present invention can especially be used for ArF immersion lithography, EUV lithography and EB lithography.

Examples

The present invention will be described more specifically by Examples, which are not construed to limit the scope of the present invention.

The "%" and "part(s)" used to represent the content of any component and the amount of any material used in the following examples and comparative examples are on a weight basis unless otherwise specifically noted. The weight-average molecular weight of any material used in the following examples is a value found by gel permeation chromatography [HLC-8120GPC Type, Column (Three Columns with guard column): TSKgel Multipore HXL-M, manufactured by TOSOH CORPORATION, Solvent: tetrahydrofuran, Flow rate: 1.0 mL/min., Detector: RI detector, Column temperature: 40° C., Injection volume: 100 μL] using standard polystyrene, manufactured by TOSOH CORPORATION, as a standard reference material. Structures of compounds were determined by NMR (EX-270 Type, manufactured by JEOL LTD.) and mass spectrometry (Liquid Chromatography: 1100 Type, manufactured by AGILENT TECHNOLOGIES LTD. , Mass Spectrometry: LC/MSD Type or LC/MSD TOF Type, manufactured by AGILENT TECHNOLOGIES LTD.).

Synthesis Example 1

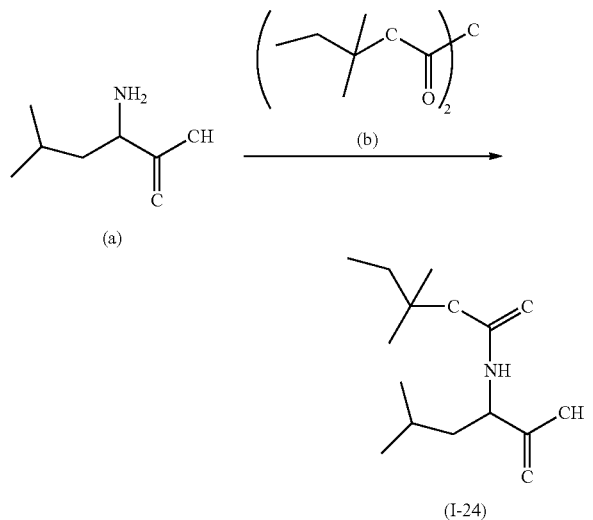

To a solution prepared by mixing 12.0 parts of the compound represented by the formula (a) available from Sigma-Aldrich Co., 36 parts of 1,4-dioxane and 36 parts of ion-exchanged water, 30 parts of triethylamine and 22.5 parts of a compound represented by the formula (b) available from Tokyo Chemical Industry Co., Ltd., were added, and the resultant mixture was stirred at room temperature over night. The obtained mixture was extracted with heptane, and an organic layer was removed. The obtained aqueous layer was mixed with 216 parts of 5% hydrochloric acid followed by conducting extraction with ethyl acetate. The obtained organic layer was dried over anhydrous magnesium sulfate and then, filtrated.

The obtained filtrate was concentrated under reduced pressure to obtain 23.1 parts of the compound represented by the formula (I-24).

$^1$H-NMR (dimethylsulfoxide-$d_6$): δ (ppm) 12.52-11.99 (1H, brm), 6.88 (1H, m), 3.93-3.78 (1H, d, J=8.2 Hz), 1.74-1.18 (11H, m), 0.86-0.66 (9H, m)

Synthesis Example 2

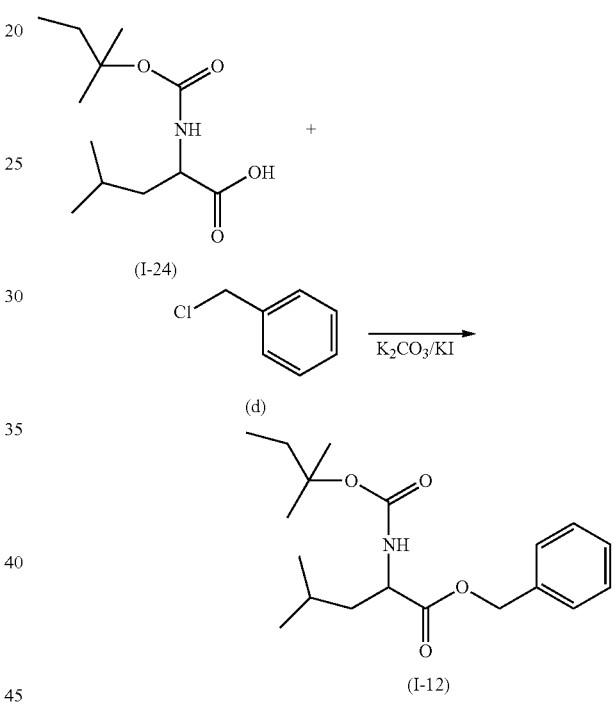

To a solution prepared by mixing 4.0 parts of the compound represented by the formula (I-24) with 25 parts of N,N-dimethylformamide, 1.33 parts of potassium carbonate and 0.40 part of potassium iodide were added, and the resultant mixture was stirred at 40° C. for 1 hour. To the mixture, 1.85 parts of the compound represented by the formula (d) was added, and the resultant mixture was stirred at 40° C. for 2 hours. The obtained mixture was cooled down to room temperature, and then, 75 parts of ion-exchanged water was added thereto. The resultant mixture was extracted with 150 parts of ethyl acetate. The obtained organic layer was washed five times with water and then, concentrated under reduced pressure to obtain 5.4 parts of the compound represented by the formula (I-12).

$^1$H-NMR (dimethylsulfoxide-$d_6$): δ (ppm) 7.44-7.20 (5H, m), 5.18-5.01 (2H, m), 4.08-3.86 (1H, m), 1.78-1.20 (11H, m), 0.91-0.67 (9H, m)

MS (ESI(+) Spectrum): [M+Na]$^+$=358.2 ($C_{19}H_{29}NO_4$=335.2)

Synthesis Example 3

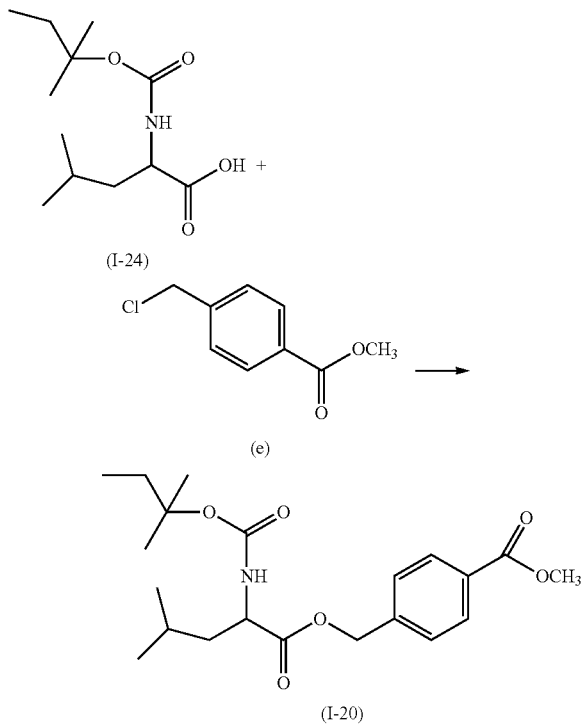

(I-24)

(e)

(I-20)

To a solution prepared by mixing 4.0 parts of the compound represented by the formula (I-24) with 25 parts of N,N-dimethylformamide, 1.33 parts of potassium carbonate and 0.40 part of potassium iodide were added, and the resultant was stirred at 40° C. for 1 hour. To the obtained mixture, 2.70 parts of the compound represented by the formula (e) available from Tokyo Chemical Industry Co., Ltd. was added. The obtained mixture was stirred at 40° C. for 2 hours. The obtained reaction mixture was cooled down to room temperature, and 75 parts of ion-exchanged water was added thereto. The resultant mixture was extracted with 150 parts of ethyl acetate. The obtained organic layer was washed five times with water and then, was concentrated under reduced pressure to obtain 4.4 parts of the compound represented by the formula (I-20).

MS (ESI(+) Spectrum): $[M+Na]^+=416.2$ ($C_{21}H_{31}NO_6=393.2$)

Synthesis Example 4

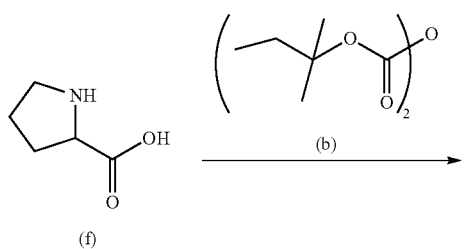

(f)

(b)

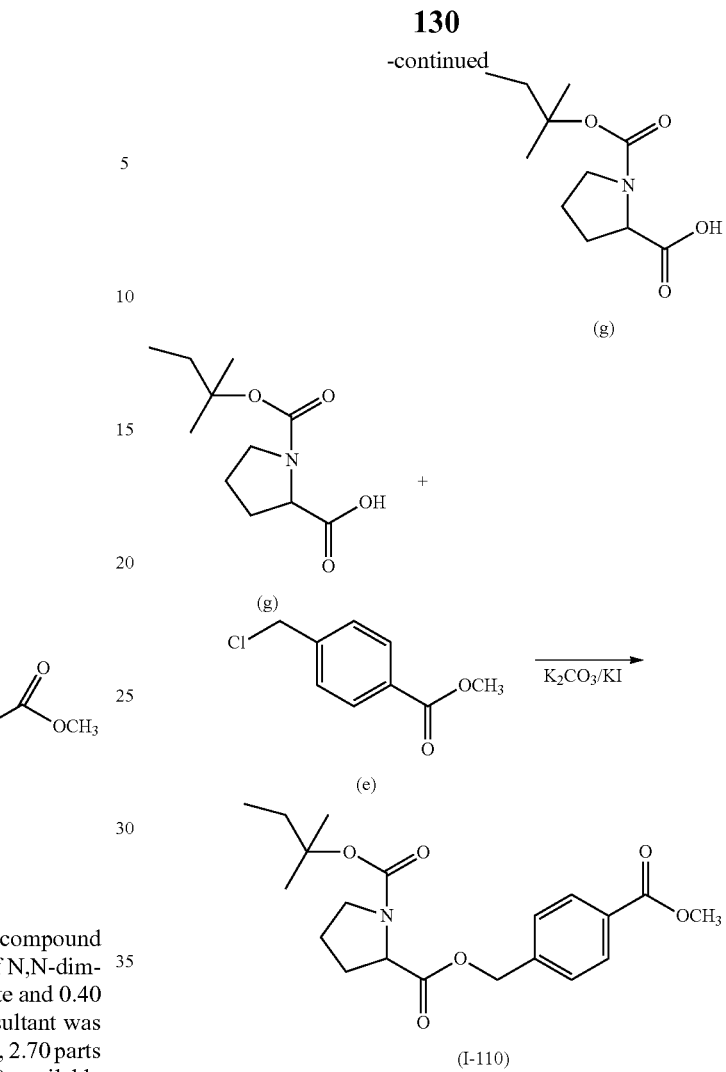

(g)

(g)

(e)

(I-110)

To a solution prepared by mixing 15.8 parts of the compound represented by the formula (f) available from Sigma-Aldrich Co., 47.4 parts of 1,4-dioxane and 47.4 parts of ion-exchanged water, 20.5 parts of triethylamine and 37.1 parts of a compound represented by the formula (b) available from Tokyo Chemical Industry Co., Ltd., were added, and the resultant mixture was stirred at room temperature over night. The obtained mixture was extracted with heptane, and an organic layer was removed. The obtained aqueous layer was mixed with 221 parts of 5% hydrochloric acid followed by conducting extraction with ethyl acetate. The obtained organic layer was dried over anhydrous magnesium sulfate and then, filtrated.

The obtained filtrate was concentrated under reduced pressure to obtain 28.5 parts of the compound represented by the formula (g).

To a solution prepared by mixing 6.8 parts of the compound represented by the formula (g) with 25 parts of N,N-dimethylformamide, 2.47 parts of potassium carbonate and 0.74 part of potassium iodide were added, and the resultant mixture was stirred at 40° C. for 1 hour. To the mixture, 5.00 parts of the compound represented by the formula (e) was added, and the resultant mixture was stirred at 40° C. for 2 hours. The obtained mixture was cooled down to room temperature, and then, 75 parts of ion-exchanged water was added thereto. The resultant mixture was extracted with 120 parts of ethyl acetate. The obtained organic layer was washed five times with water and then, concentrated under reduced pressure to obtain 8.9 parts of the compound represented by the formula (I-110).

$^1$H-NMR (dimethylsulfoxide-$d_6$): δ (ppm) 8.00-7.89 (2H, m), 7.55-7.43 (2H, m), 5.30-5.11 (2H, m), 4.30-4.17 (1H, m), 3.84 (3H, s), 3.42-3.22 (2H, m), 2.33-2.10 (1H, m), 1.95-1.47 (5H, m), 1.37-1.21 (6H, m), 0.85-0.65 (3H, m)

In Resin Synthesis Example 1, the following monomers were used.

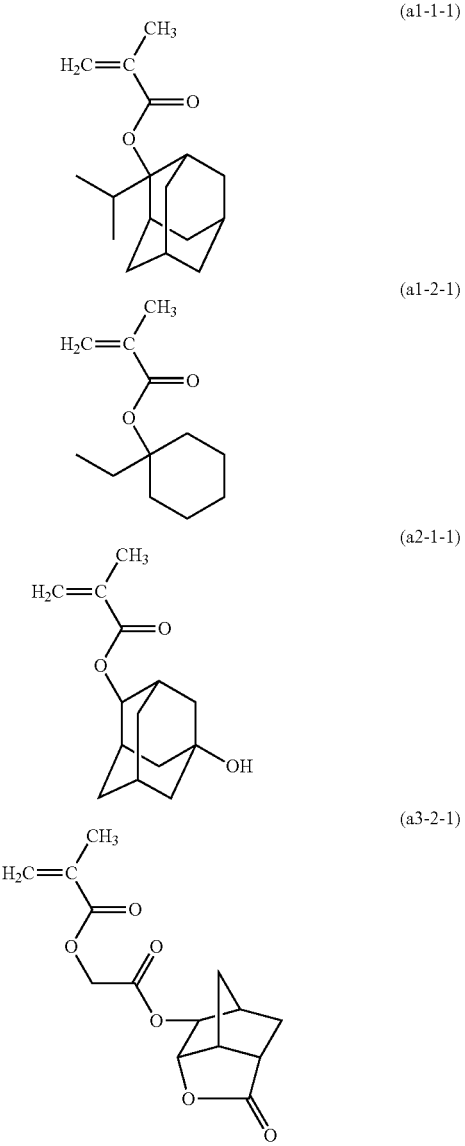

Resin Synthesis Example 1

To a four-necked flask equipped with a thermometer and a reflux condenser, 72.77 parts of 1,4-dioxane was added, and a nitrogen gas was blown into it for 30 minutes. After heating it up to 75° C. under nitrogen, a solution prepared by mixing 76.30 parts of monomer represented by the formula (a1-1-1), 11.42 parts of monomer represented by the formula (a1-2-1), 11.74 parts of monomer represented by the formula (a2-1-1), 52.16 parts of monomer represented by the formula (a3-2-1), 0.96 parts of 2,2'-azobisisobutyronitrile, 4.33 parts of 2,2'-azobis(2,4-dimethylvaleronitrile) and 109.16 parts of 1,4-dioxane was added dropwise thereto over 2 hour at 75° C. The resultant mixture was stirred for 5 hours at 75° C. After cooling the reaction mixture down to room temperature, the reaction mixture was diluted with 212.26 parts of 1,4-dioxane and the resultant solution was poured into a mixture of 536 parts of methanol and 394 parts of water to cause precipitation. The precipitate was isolated and mixed with 985 parts of methanol. The resultant mixture was stirred followed by filtrating to obtain the precipitate. The operation wherein the precipitate was mixed with 985 parts of methanol and the resultant mixture was stirred followed by filtrating to obtain the precipitate was repeated three times. The obtained precipitate was dried under reduced pressure to obtain 112 parts of a resin having a weight-average molecular weight (Mw) of 7,400 and a dispersion degree (Mw/Mn) of 1.83 in a yield of 74%. This resin had the structural units derived from monomers represented by the formulae (a1-1-1), (a1-2-1), (a2-1-1) and (a3-2-1). This is called as Resin A1. The ratio of the structural units derived from monomers represented by the formulae (a1-1-1), (a1-2-1), (a2-1-1) and (a3-2-1) ((a1-1-1)/(a1-2-1)/(a2-1-1)/(a3-2-1)) was 40/10/10/40. This ratio is molar ratio of the structural units derived from monomers represented by the formulae (a1-1-1), (a1-2-1), (a2-1-1) and (a3-2-1) and it was calculated based on the amount of the unreacted monomers in the reaction mixture, which was measured by liquid chromatography analysis using LC 2010HT, manufactured by Shimadzu Corporation.

Examples 1 to 4 and Reference Examples 1 to 2

Resin

Resin A1
<Acid Generator>
B1:

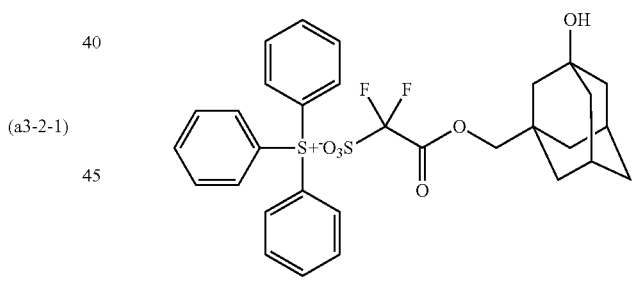

<Quencher>
I-12: compound represented by the formula (I-12)
I-20: compound represented by the formula (I-20)
I-24: compound represented by the formula (I-24)
I-110: compound represented by the formula (I-110)
Q1: 2,6-diisopropylaniline
Q2:

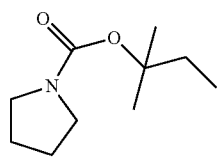

<Solvent>

| S1: propylene glycol monomethyl ether acetate | 250 parts |
|---|---|
| propylene glycol monomethyl ether | 20 parts |
| 2-heptanone | 10 parts |
| γ-butyrolactone | 3 parts |

The following components were mixed and dissolved, further, filtrated through a fluorine resin filter having pore diameter of 0.2 μm, to prepare photoresist compositions.
Resin (kind and amount are described in Table 3)
Acid generator (kind and amount are described in Table 3)
Quencher (kind and amount are described in Table 3)
Solvent S1

TABLE 3

| Ex. No. | Resin (kind/amount (part)) | Acid generator (kind/amount (part)) | Quencher (kind/amount (part)) | PB (° C.) | PEB (° C.) |
|---|---|---|---|---|---|
| Ex. 1 | A1/10 | B1/0.95 | I-12/0.030 | 95 | 85 |
| Ex. 2 | A1/10 | B1/0.95 | I-20/0.035 | 95 | 85 |
| Ex. 3 | A1/10 | B1/0.95 | I-24/0.022 | 95 | 85 |
| Ex. 4 | A1/10 | B1/0.95 | I-110/0.034 | 95 | 85 |
| Ref. Ex. 1 | A1/10 | B1/0.95 | Q1/0.012 | 95 | 85 |
| Ref. Ex. 2 | A1/10 | B1/0.95 | Q2/0.017 | 95 | 85 |

Silicon wafers were each coated with "ARC-29SR", which is an organic anti-reflective coating composition available from Nissan Chemical Industries, Ltd., and then baked under the conditions: 205° C., 60 seconds, to form a 930 Å-thick organic anti-reflective coating. Each of the resist liquids prepared as above was spin-coated over the anti-reflective coating so that the thickness of the resulting film became 100 nm after drying. The silicon wafers thus coated with the respective resist liquids were each prebaked on a direct hotplate at a temperature shown in column of "PB" of Table 3 for 60 seconds. Using an ArF excimer stepper ("XT:1900Gi" manufactured by ASML, NA=1.35, ¾ Annular, σ OUTER=0.9, σ INNER=0.675), each wafer thus formed with the respective resist film was subjected to contact hole pattern exposure using photomasks for forming a hole pattern having pitch of 100 nm and hole diameter of 68 to 72 nm with 1 nm increments in between.

After the exposure, each wafer was subjected to post-exposure baking on a hotplate at a temperature shown in column of "PEB" of Table 3 for 60 seconds and then to paddle development for 60 seconds with an aqueous solution of 2.38 wt % tetramethylammonium hydroxide.

Each of hole patterns developed on the organic anti-reflective coating substrate after the development was observed with a scanning electron microscope, the results of which are shown in Tables 4.

Effective Sensitivity (ES): It was expressed as the amount of exposure that hole diameter of the hole pattern became 70 nm after exposure using a photomask for forming a hole pattern having pitch of 100 nm and hole diameter of 70 nm and development.

Mask Error Enhancement Factor (MEEF): Hole diameters of each hole patterns exposed at ES using photomasks for forming a hole pattern having pitch of 100 nm and hole diameter of 68 to 72 nm with 1 nm increments in between and developed were measured. A graph wherein the hole diameter of used photomask is a vertical axis and the hole diameter of the obtained hole patterns is a horizontal axis was made and the straight line was drawn. MEEF was expressed as the value of the slope of the straight line. The closer the value of the slope is to 1, the better MEEF is.

TABLE 4

| Ex. No. | MEEF |
|---|---|
| Ex. 1 | 2.49 |
| Ex. 2 | 2.89 |
| Ex. 3 | 2.62 |
| Ex. 4 | 2.80 |
| Ref. Ex. 1 | 3.42 |
| Ref. Ex. 2 | 3.20 |

The photoresist composition of the present invention provides a good resist pattern having good Mask Error Enhancement Factor.

What is claimed is:
1. A photoresist composition comprising a resin, a salt represented by the formula (B1):

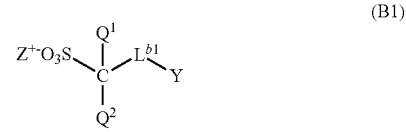

wherein $Q^1$ and $Q^2$ each independently represent a fluorine atom or a C1-C6 perfluoroalkyl group,
$L^{b1}$ represents a single bond or a C1-C17 divalent saturated hydrocarbon group in which one or more methylene groups can be replaced by —O— or —CO—,
Y represents a C1-C18 aliphatic hydrocarbon group which can have one or more substituents, or a C3-C18 saturated cyclic hydrocarbon group which can have one or more substituents, and one or more methylene groups in the aliphatic hydrocarbon group and the saturated cyclic hydrocarbon group can be replaced by —O—, —CO— or —SO$_2$—, and $Z^+$ represents an organic cation,
and a compound represented by the formula (I):

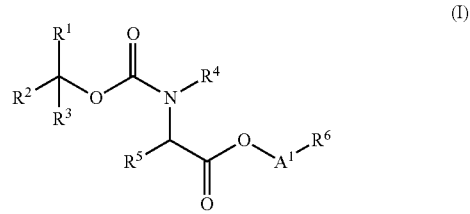

wherein $R^1$ represents a C2-C12 alkyl group which can have one or more hydroxyl groups or a C7-C12 aralkyl group which can have one or more hydroxyl groups, and one or more —CH$_2$— in the alkyl and aralkyl groups can be replaced by —O— or —CO—,
$R^2$ and $R^3$ each independently represent a hydrogen atom or a C1-C12 alkyl group which can have one or more hydroxyl groups, and one or more —CH$_2$— in the alkyl group can be replaced by —O— or —CO—, and $R^1$ and $R^2$ can be bonded each other to form a C3-C36 ring together with the carbon atom to which $R^1$ and $R^2$ are bonded, and the ring can have one or more hydroxyl groups and one or more —CH$_2$— in the ring can be replaced by —O— or —CO—, $R^4$ and $R^5$ each independently represent a hydrogen atom, a C1-C6 alkyl group, a C3-C12 saturated cyclic hydrocarbon group, a C6-C12 aromatic hydrocarbon group or a C5-C9 heteroaromatic group, and $R^4$ and $R^5$ can be bonded each other to form a C5-C6 heterocycle together with —CH—N— to which $R^4$ and $R^5$ are bonded, and the alkyl group can have one or more substituents selected from the group consisting of —OH, —SH, —NH$_2$, a C3-C12 saturated cyclic hydrocarbon group, a C6-C12 aromatic hydrocarbon group and a C5-C9 heteroaromatic group, and one or more —CH$_2$— in the alkyl group can be replaced by —O—, —S—, —CO—, —C(=NH) or —NH—, and the saturated cyclic hydrocarbon group, the aromatic hydrocarbon group and the heteroaromatic group can have one or more substituents selected from the group consisting of —OH, —CO—R$^7$, —O—CO—R$^7$ and —CO—O—R$^7$ in which R$^7$ represents a C1-C6 alkyl group, $R^6$ represents a C3-C12 saturated cyclic hydrocarbon group, a C6-C12 aromatic hydrocarbon group or a C5-C9 heteroaromatic group, and $A^1$ represents a single bond or a C1-C2 alkylene group in which one methylene group can be replaced by an oxygen atom.

2. The photoresist composition according to claim 1, wherein $R^1$ is an ethyl group and $R^2$ and $R^3$ are methyl groups in the formula (I).

3. The photoresist composition according to claim 1, wherein $R^4$ is a hydrogen atom in the formula (I).

4. The photoresist composition according to claim 1, wherein the resin has an acid-labile group and is insoluble or poorly soluble in an aqueous alkali solution but becomes soluble in an aqueous alkali solution by the action of an acid.

5. A process for producing a photoresist pattern comprising the following steps (1) to (5):

(1) a step of applying the photoresist composition according to claim 1 on a substrate, (2) a step of forming a photoresist film by conducting drying, (3) a step of exposing the photoresist film to radiation, (4) a step of baking the exposed photoresist film, and (5) a step of developing the baked photoresist film with an alkaline developer, thereby forming a photoresist pattern.

* * * * *